US012589237B2

(12) United States Patent
Wenning et al.

(10) Patent No.: US 12,589,237 B2
(45) Date of Patent: Mar. 31, 2026

(54) MECHANICAL CIRCULATORY SUPPORT SYSTEM WITH GUIDEWIRE AID

(71) Applicant: Kardion GmbH, Stuttgart (DE)

(72) Inventors: Leon Wenning, Stuttgart (DE); Inga Schellenberg, Stuttgart (DE); Johannes Bette, Balingen (DE); Armin Schuelke, Aidlingen (DE); David Minzenmay, Stuttgart (DE); Marvin Mitze, Stuttgart (DE); Hardy Baumbach, Stuttgart (DE); Ingo Stotz, Ditzingen (DE); Mario Heintze, Dresden (DE); Thomas Friedrich, Dresden (DE); Evelin Matthes, Dresden (DE); Hans Christof, Unterensingen (DE)

(73) Assignee: Kardion GmbH, Stuttgart (DE)

( * ) Notice: Subject to any disclaimer, the term of this patent is extended or adjusted under 35 U.S.C. 154(b) by 911 days.

(21) Appl. No.: 17/455,658

(22) Filed: Nov. 18, 2021

(65) Prior Publication Data

US 2022/0161018 A1 May 26, 2022

Related U.S. Application Data

(60) Provisional application No. 63/229,436, filed on Aug. 4, 2021, provisional application No. 63/224,326, filed
(Continued)

(51) Int. Cl.
| | |
|---|---|
| *A61M 60/237* | (2021.01) |
| *A61M 25/09* | (2006.01) |
| *A61M 60/148* | (2021.01) |

(52) U.S. Cl.
CPC .... *A61M 60/237* (2021.01); *A61M 25/09041* (2013.01); *A61M 60/148* (2021.01);
(Continued)

(58) Field of Classification Search
CPC .. A61M 60/13; A61M 60/148; A61M 60/857; A61M 60/216; A61M 60/237;
(Continued)

(56) References Cited

U.S. PATENT DOCUMENTS

| | | | |
|---|---|---|---|
| 2,254,698 | A | 9/1941 | Hansen, Jr. |
| 2,310,923 | A | 2/1943 | Bean |

(Continued)

FOREIGN PATENT DOCUMENTS

| | | |
|---|---|---|
| AU | 7993698 | 2/1999 |
| AU | 2002308409 | 12/2005 |

(Continued)

OTHER PUBLICATIONS

Invitation to Pay Additional Fees received in PCT Application No. PCT/US2021/072499, dated Mar. 21, 2022 in 11 pages.
(Continued)

*Primary Examiner* — Jon Eric C Morales
(74) *Attorney, Agent, or Firm* — Knobbe, Martens, Olson & Bear, LLP

(57) ABSTRACT

Disclosed is a mechanical circulatory support system for transcatheter delivery to the heart, having a removable guidewire aid to assist with inserting the guidewire along a path that avoids a rotating impeller. The system may comprise a catheter shaft and a circulatory support device carried by the shaft. The device may comprise a tubular housing, an impeller and the guidewire aid. The guidewire aid may include a removable guidewire guide tube. The guide tube may enter a first guidewire port of the tubular housing, exit the tubular housing via a second guidewire port on a side wall of the tubular housing on a distal side of the impeller, enter a third guidewire port on a proximal side of the impeller, and extend proximally through the catheter shaft.

16 Claims, 27 Drawing Sheets

Related U.S. Application Data on Jul. 21, 2021, provisional application No. 63/116,616, filed on Nov. 20, 2020, provisional application No. 63/116,686, filed on Nov. 20, 2020.

(52) U.S. Cl.
 CPC ............. *A61M 2025/09083* (2013.01); *A61M 2025/09175* (2013.01); *A61M 2210/125* (2013.01)

(58) Field of Classification Search
 CPC .............. A61M 60/414; A61M 60/419; A61M 60/422; A61M 60/829; A61M 60/865; A61M 2025/0024; A61M 2025/0177; A61M 2025/018; A61M 2025/09083; A61M 2025/09175; A61M 2205/0216; A61M 2210/125; A61M 25/09; A61M 25/09041; A61M 60/126; A61M 60/221; A61M 60/416; A61M 60/585; A61M 60/806; A61M 60/824; A61M 60/825; A61M 60/827; A61M 60/861; A61B 17/320758; A61B 2017/00477; A61B 2017/00831; A61B 2017/00836; A61L 29/02; F16C 1/06; F16C 1/28; F16C 2316/10
 See application file for complete search history.

(56) References Cited

U.S. PATENT DOCUMENTS

| | | | |
|---|---|---|---|
| 3,085,407 A | 4/1963 | Tomlinson |
| 3,505,987 A | 4/1970 | Heilman |
| 3,568,659 A | 3/1971 | Kamegis |
| 3,614,181 A | 10/1971 | Meeks |
| 3,747,998 A | 7/1973 | Klein et al. |
| 3,807,813 A | 4/1974 | Milligan |
| 3,995,617 A | 12/1976 | Watkins et al. |
| 4,115,040 A | 9/1978 | Knorr |
| 4,245,622 A | 1/1981 | Hutchins, IV |
| 4,471,252 A | 9/1984 | West |
| 4,522,194 A | 6/1985 | Normann |
| 4,625,712 A | 12/1986 | Wampler |
| 4,643,641 A | 2/1987 | Clausen et al. |
| 4,753,221 A | 6/1988 | Kensey et al. |
| 4,779,614 A | 10/1988 | Moise |
| 4,785,795 A | 11/1988 | Singh et al. |
| 4,802,650 A | 2/1989 | Stricker |
| 4,817,586 A | 4/1989 | Wampler |
| 4,846,152 A | 7/1989 | Wampler et al. |
| 4,888,011 A | 12/1989 | Kung et al. |
| 4,889,131 A | 12/1989 | Salem et al. |
| 4,895,557 A | 1/1990 | Moise et al. |
| 4,896,754 A | 1/1990 | Carlson et al. |
| 4,902,272 A | 2/1990 | Milder et al. |
| 4,908,012 A | 3/1990 | Moise et al. |
| 4,919,647 A | 4/1990 | Nash |
| 4,921,479 A | 5/1990 | Grayzel |
| 4,927,407 A | 5/1990 | Dorman |
| 4,943,275 A | 7/1990 | Stricker |
| 4,944,722 A | 7/1990 | Carriker et al. |
| 4,968,300 A | 11/1990 | Moutafis et al. |
| 4,971,768 A | 11/1990 | Ealba |
| 4,985,014 A | 1/1991 | Orejola |
| 5,044,897 A | 9/1991 | Dorman |
| 5,061,256 A | 10/1991 | Wampler |
| 5,084,064 A | 1/1992 | Barak et al. |
| 5,089,016 A | 2/1992 | Millner et al. |
| 5,090,957 A | 2/1992 | Moutafis et al. |
| 5,112,292 A | 5/1992 | Hwang et al. |
| 5,112,349 A | 5/1992 | Summers et al. |
| 5,116,305 A | 5/1992 | Milder et al. |
| 5,195,877 A | 3/1993 | Kletschka |
| 5,290,227 A | 3/1994 | Pasque |

| | | | |
|---|---|---|---|
| 5,297,940 A | 3/1994 | Buse |
| 5,313,765 A | 5/1994 | Martin |
| 5,322,509 A | 6/1994 | Rickerd |
| 5,330,460 A | 7/1994 | Moss et al. |
| 5,344,443 A | 9/1994 | Palma et al. |
| 5,354,271 A | 10/1994 | Voda |
| 5,376,114 A | 12/1994 | Jarvik |
| 5,399,145 A | 3/1995 | Ito et al. |
| 5,405,383 A | 4/1995 | Barr |
| 5,409,463 A | 4/1995 | Thomas et al. |
| 5,443,503 A | 8/1995 | Yamane |
| 5,456,715 A | 10/1995 | Liotta |
| 5,527,159 A | 6/1996 | Bozeman, Jr. et al. |
| 5,599,173 A | 2/1997 | Chen et al. |
| 5,613,935 A | 3/1997 | Jarvik |
| 5,647,127 A | 7/1997 | Miyata et al. |
| 5,695,471 A | 12/1997 | Wampler |
| 5,702,430 A | 12/1997 | Larson, Jr. et al. |
| 5,720,771 A | 2/1998 | Snell |
| 5,746,709 A | 5/1998 | Rom et al. |
| 5,749,855 A | 5/1998 | Reitan |
| 5,752,937 A | 5/1998 | Otten et al. |
| 5,752,976 A | 5/1998 | Duffin et al. |
| 5,766,207 A | 6/1998 | Potter et al. |
| 5,831,365 A | 11/1998 | Keim et al. |
| 5,888,241 A | 3/1999 | Jarvik |
| 5,888,242 A | 3/1999 | Antaki et al. |
| 5,904,646 A | 5/1999 | Jarvik |
| 5,911,685 A | 6/1999 | Siess et al. |
| 5,921,913 A | 7/1999 | Siess |
| 5,928,132 A | 7/1999 | Leschinsky |
| 5,964,694 A | 10/1999 | Siess et al. |
| 6,001,056 A | 12/1999 | Jassawalla et al. |
| 6,007,478 A | 12/1999 | Siess et al. |
| 6,018,208 A | 1/2000 | Maher et al. |
| 6,050,975 A | 4/2000 | Poirier |
| 6,071,093 A | 6/2000 | Hart |
| 6,116,862 A | 9/2000 | Rau et al. |
| 6,123,659 A | 9/2000 | le Blanc et al. |
| 6,135,710 A | 10/2000 | Araki et al. |
| 6,149,405 A | 11/2000 | Abe et al. |
| 6,152,909 A | 11/2000 | Bagaoisan |
| 6,155,969 A | 12/2000 | Schima et al. |
| 6,158,984 A | 12/2000 | Cao et al. |
| 6,159,198 A | 12/2000 | Gardeski et al. |
| 6,161,838 A | 12/2000 | Balsells |
| 6,176,848 B1 | 1/2001 | Rau et al. |
| 6,186,665 B1 | 2/2001 | Maher et al. |
| 6,210,318 B1 | 4/2001 | Lederman |
| 6,217,541 B1 | 4/2001 | Yu |
| 6,220,832 B1 | 4/2001 | Schob |
| 6,227,820 B1 | 5/2001 | Jarvik |
| 6,245,007 B1 | 6/2001 | Bedingham et al. |
| 6,254,359 B1 | 7/2001 | Aber |
| 6,264,205 B1 | 7/2001 | Balsells |
| 6,264,601 B1 | 7/2001 | Jassawalla et al. |
| 6,264,645 B1 | 7/2001 | Jonkman |
| 6,293,752 B1 | 9/2001 | Clague et al. |
| 6,351,048 B1 | 2/2002 | Schob et al. |
| 6,361,292 B1 | 3/2002 | Chang et al. |
| 6,432,136 B1 | 8/2002 | Weiss et al. |
| 6,445,956 B1 | 9/2002 | Laird et al. |
| 6,447,266 B2 | 9/2002 | Antaki et al. |
| 6,450,948 B1 | 9/2002 | Matsuura et al. |
| 6,497,681 B1 | 12/2002 | Brenner |
| 6,527,698 B1 | 3/2003 | Kung et al. |
| 6,530,876 B1 | 3/2003 | Spence |
| 6,533,716 B1 | 3/2003 | Schmitz-Rode et al. |
| 6,540,658 B1 | 4/2003 | Fasciano et al. |
| 6,544,216 B1 | 4/2003 | Sammler et al. |
| 6,544,247 B1 | 4/2003 | Gardeski et al. |
| 6,579,257 B1 | 6/2003 | Elgas et al. |
| 6,592,620 B1 | 7/2003 | Lancisi et al. |
| 6,595,743 B1 | 7/2003 | Kazatchkov et al. |
| 6,607,368 B1 | 8/2003 | Ross et al. |
| 6,623,475 B1 | 9/2003 | Siess |
| 6,719,791 B1 | 4/2004 | Nüsser et al. |
| 6,743,239 B1 | 6/2004 | Kuehn |
| 6,794,789 B2 | 9/2004 | Siess et al. |

(56) References Cited

U.S. PATENT DOCUMENTS

| | | | |
|---|---|---|---|
| 6,841,910 B2 | 1/2005 | Gery |
| 6,879,126 B2 | 4/2005 | Paden et al. |
| 6,912,423 B2 | 6/2005 | Ley et al. |
| 6,942,611 B2 | 9/2005 | Siess |
| 6,949,066 B2 | 9/2005 | Bearnson et al. |
| 6,969,345 B2 | 11/2005 | Jassawalla et al. |
| 7,011,620 B1 | 3/2006 | Siess |
| 7,014,620 B2 | 3/2006 | Kim |
| 7,022,100 B1 | 4/2006 | Aboul-Hosn et al. |
| 7,027,875 B2 | 4/2006 | Siess et al. |
| 7,070,398 B2 | 7/2006 | Olsen et al. |
| 7,070,555 B2 | 7/2006 | Siess |
| 7,083,588 B1 | 8/2006 | Shmulewitz et al. |
| 7,144,364 B2 | 12/2006 | Barbut et al. |
| 7,160,243 B2 | 1/2007 | Medvedev |
| 7,166,088 B2 | 1/2007 | Heuser |
| 7,238,151 B2 | 7/2007 | Frazier |
| 7,241,257 B1 | 7/2007 | Ainsworth et al. |
| 7,250,041 B2 | 7/2007 | Chiu et al. |
| 7,264,606 B2 | 9/2007 | Jarvik et al. |
| 7,357,794 B2 | 4/2008 | Makower et al. |
| 7,393,181 B2 | 7/2008 | McBride et al. |
| 7,419,486 B2 | 9/2008 | Kampa |
| 7,462,019 B1 | 12/2008 | Allarie et al. |
| 7,479,102 B2 | 1/2009 | Jarvik |
| 7,502,648 B2 | 3/2009 | Okubo et al. |
| 7,621,894 B2 | 11/2009 | Leeflang et al. |
| 7,722,568 B2 | 5/2010 | Lenker et al. |
| 7,736,296 B2 | 6/2010 | Siess et al. |
| 7,744,571 B2 | 6/2010 | Fisher et al. |
| 7,762,941 B2 | 7/2010 | Jarvik |
| 7,798,952 B2 | 9/2010 | Tansley et al. |
| 7,824,375 B2 | 11/2010 | Hastings, Jr. et al. |
| 7,841,976 B2 | 11/2010 | McBride et al. |
| 7,850,593 B2 | 12/2010 | Vincent et al. |
| 7,878,967 B1 | 2/2011 | Khanal |
| 7,914,436 B1 | 3/2011 | Kung |
| 7,934,909 B2 | 5/2011 | Nuesser et al. |
| 7,951,119 B2 | 5/2011 | Leeflang et al. |
| 7,959,551 B2 | 6/2011 | Jarvik |
| 7,963,905 B2 | 6/2011 | Salmonsen et al. |
| 7,998,190 B2 | 8/2011 | Gharib et al. |
| 8,012,079 B2 | 9/2011 | Delgado, III |
| 8,025,647 B2 | 9/2011 | Siess et al. |
| 8,043,263 B2 | 10/2011 | Helgeson et al. |
| 8,075,472 B2 | 12/2011 | Zilbershlag et al. |
| 8,088,059 B2 | 1/2012 | Jarvik |
| 8,088,154 B2 | 1/2012 | Hoffman et al. |
| 8,114,008 B2 | 2/2012 | Hidaka et al. |
| 8,123,669 B2 | 2/2012 | Siess et al. |
| RE43,299 E | 4/2012 | Siess |
| 8,152,845 B2 | 4/2012 | Bourque |
| 8,157,719 B1 | 4/2012 | Ainsworth et al. |
| 8,177,703 B2 | 5/2012 | Smith et al. |
| 8,216,122 B2 | 7/2012 | Kung |
| 8,231,519 B2 | 7/2012 | Reichenbach et al. |
| 8,262,619 B2 | 9/2012 | Chebator et al. |
| 8,292,908 B2 | 10/2012 | Nieman et al. |
| 8,343,028 B2 | 1/2013 | Gregoric et al. |
| 8,371,997 B2 | 2/2013 | Shifflette |
| 8,376,926 B2 | 2/2013 | Benkowsi et al. |
| 8,382,695 B1 | 2/2013 | Patel |
| 8,382,830 B2 | 2/2013 | Maher et al. |
| 8,388,565 B2 | 3/2013 | Shifflette |
| 8,419,609 B2 | 4/2013 | Shambaugh, Jr. et al. |
| 8,449,443 B2 | 5/2013 | Rodefeld et al. |
| 8,475,431 B2 | 7/2013 | Howat |
| 8,480,555 B2 | 7/2013 | Kung |
| 8,480,627 B2 | 7/2013 | Christiansen |
| 8,485,961 B2 | 7/2013 | Campbell et al. |
| 8,512,012 B2 | 8/2013 | Akdis et al. |
| 8,535,211 B2 | 9/2013 | Campbell et al. |
| 8,545,380 B2 | 10/2013 | Farnan et al. |
| 8,562,508 B2 | 10/2013 | Dague et al. |
| 8,579,966 B2 | 11/2013 | Seguin et al. |
| 8,585,572 B2 | 11/2013 | Mehmanesh |
| 8,591,393 B2 | 11/2013 | Walters et al. |
| 8,591,538 B2 | 11/2013 | Gellman |
| 8,591,539 B2 | 11/2013 | Gellman |
| 8,597,170 B2 | 12/2013 | Walters et al. |
| 8,613,777 B2 | 12/2013 | Siess et al. |
| 8,617,239 B2 | 12/2013 | Reitan |
| 8,622,949 B2 | 1/2014 | Zafirelis et al. |
| 8,641,594 B2 | 2/2014 | LaRose et al. |
| 8,657,875 B2 | 2/2014 | Kung et al. |
| 8,684,362 B2 | 4/2014 | Balsells et al. |
| 8,684,904 B2 | 4/2014 | Campbell et al. |
| 8,690,749 B1 | 4/2014 | Nunez |
| 8,721,517 B2 | 5/2014 | Zeng et al. |
| 8,727,959 B2 | 5/2014 | Reitan et al. |
| 8,728,055 B2 | 5/2014 | Stehr et al. |
| 8,731,664 B2 | 5/2014 | Foster et al. |
| 8,734,331 B2 | 5/2014 | Evans et al. |
| 8,814,776 B2 | 8/2014 | Hastie et al. |
| 8,814,933 B2 | 8/2014 | Siess |
| 8,849,398 B2 | 9/2014 | Evans |
| 8,852,173 B2 | 10/2014 | Sigg et al. |
| 8,864,642 B2 | 10/2014 | Scheckel |
| 8,864,643 B2 | 10/2014 | Reichenbach et al. |
| 8,864,644 B2 | 10/2014 | Yomtov |
| 8,882,477 B2 | 11/2014 | Fritz, IV et al. |
| 8,888,728 B2 | 11/2014 | Aboul-Hosn et al. |
| 8,894,387 B2 | 11/2014 | White |
| 8,897,873 B2 | 11/2014 | Schima et al. |
| 8,900,060 B2 | 12/2014 | Liebing |
| 8,900,115 B2 | 12/2014 | Bolling et al. |
| 8,926,564 B2 | 1/2015 | King et al. |
| 8,932,246 B2 | 1/2015 | Ferrari |
| 8,992,406 B2 | 3/2015 | Corbett |
| 8,992,407 B2 | 3/2015 | Smith et al. |
| 9,028,216 B2 | 5/2015 | Schumacher et al. |
| 9,028,392 B2 | 5/2015 | Shifflette |
| 9,033,863 B2 | 5/2015 | Jarvik |
| 9,091,271 B2 | 7/2015 | Bourque |
| 9,138,518 B2 | 9/2015 | Campbell et al. |
| 9,144,638 B2 | 9/2015 | Zimmermann et al. |
| 9,144,669 B2 | 9/2015 | Wieselthaler |
| 9,149,606 B2 | 10/2015 | Beissel et al. |
| 9,162,017 B2 | 10/2015 | Evans et al. |
| 9,168,060 B2 | 10/2015 | Voss |
| 9,192,705 B2 | 11/2015 | Yanai et al. |
| 9,199,020 B2 | 12/2015 | Siess |
| 9,265,870 B2 | 2/2016 | Reichenbach et al. |
| 9,297,735 B2 | 3/2016 | Graichen et al. |
| 9,308,305 B2 | 4/2016 | Chen et al. |
| 9,314,556 B2 | 4/2016 | Tuseth |
| 9,327,067 B2 | 5/2016 | Zeng et al. |
| 9,327,068 B2 | 5/2016 | Aboul-Hosn et al. |
| 9,345,824 B2 | 5/2016 | Mohl et al. |
| 9,364,592 B2 | 6/2016 | McBride |
| 9,370,613 B2 | 6/2016 | Hsu et al. |
| 9,371,826 B2 | 6/2016 | Yanai et al. |
| 9,381,286 B2 | 7/2016 | Spence et al. |
| 9,402,942 B2 | 8/2016 | Hastie et al. |
| 9,421,311 B2 | 8/2016 | Tanner et al. |
| 9,433,713 B2 | 9/2016 | Corbett et al. |
| 9,440,013 B2 | 9/2016 | Dowling et al. |
| 9,452,249 B2 | 9/2016 | Kearsley et al. |
| 9,474,840 B2 | 10/2016 | Siess |
| 9,486,566 B2 | 11/2016 | Siess |
| 9,492,601 B2 | 11/2016 | Casas et al. |
| 9,510,813 B2 | 12/2016 | Levy et al. |
| 9,533,084 B2 | 1/2017 | Siess et al. |
| 9,539,094 B2 | 1/2017 | Dale et al. |
| 9,539,378 B2 | 1/2017 | Tuseth |
| 9,545,468 B2 | 1/2017 | Aboul-Hosn et al. |
| 9,550,017 B2 | 1/2017 | Spanier et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,561,313 B2 | 2/2017 | Taskin |
| 9,561,314 B2 | 2/2017 | Aboul-Hosn et al. |
| 9,569,985 B2 | 2/2017 | Alkhatib et al. |
| 9,579,433 B2 | 2/2017 | LaRose et al. |

(56) References Cited

U.S. PATENT DOCUMENTS

| | | | |
|---|---|---|---|
| 9,585,991 B2 | 3/2017 | Spence |
| 9,592,397 B2 | 3/2017 | Hansen et al. |
| 9,597,063 B2 | 3/2017 | Voss et al. |
| 9,616,157 B2 | 4/2017 | Akdis |
| 9,616,159 B2 | 4/2017 | Anderson et al. |
| 9,623,162 B2 | 4/2017 | Graham et al. |
| 9,623,163 B1 | 4/2017 | Fischi |
| 9,636,442 B2 | 5/2017 | Karmon et al. |
| 9,656,011 B2 | 5/2017 | Graham et al. |
| 9,669,144 B2 | 6/2017 | Spanier et al. |
| 9,675,738 B2 | 6/2017 | Tanner et al. |
| 9,675,739 B2 | 6/2017 | Tanner et al. |
| 9,675,740 B2 | 6/2017 | Zeng et al. |
| 9,682,180 B2 | 6/2017 | Hoarau et al. |
| 9,717,833 B2 | 8/2017 | McBride et al. |
| 9,724,083 B2 | 8/2017 | Quadri et al. |
| 9,731,058 B2 | 8/2017 | Siebenhaar et al. |
| 9,744,279 B2 | 8/2017 | Tamez et al. |
| 9,750,861 B2 | 9/2017 | Hastie et al. |
| 9,759,222 B2 | 9/2017 | Zimmermann et al. |
| 9,769,912 B2 | 9/2017 | Helm et al. |
| 9,770,543 B2 | 9/2017 | Tanner et al. |
| 9,782,905 B2 | 10/2017 | Drake et al. |
| 9,789,238 B2 | 10/2017 | Aboul-Hosn et al. |
| 9,801,990 B2 | 10/2017 | Lynch |
| 9,807,860 B2 | 10/2017 | Helm et al. |
| 9,814,813 B2 | 11/2017 | Corbett |
| 9,814,814 B2 | 11/2017 | Corbett et al. |
| 9,821,100 B2 | 11/2017 | Corbett et al. |
| 9,821,101 B2 | 11/2017 | Andrus et al. |
| 9,821,146 B2 | 11/2017 | Tao et al. |
| 9,827,356 B2 | 11/2017 | Muller et al. |
| 9,833,550 B2 | 12/2017 | Siess |
| 9,849,223 B2 | 12/2017 | LaRose |
| 9,872,948 B2 | 1/2018 | Siess |
| 9,878,087 B2 | 1/2018 | Richardson et al. |
| 9,907,890 B2 | 3/2018 | Muller |
| 9,919,087 B2 | 3/2018 | Pfeffer et al. |
| 9,950,101 B2 | 4/2018 | Smith et al. |
| 9,968,719 B2 | 5/2018 | Colella |
| 9,974,893 B2 | 5/2018 | Toellner |
| 9,974,938 B2 | 5/2018 | Pepin et al. |
| 9,999,714 B2 | 6/2018 | Spanier et al. |
| 10,010,412 B2 | 7/2018 | Taft |
| 10,029,037 B2 | 7/2018 | Muller et al. |
| 10,080,871 B2 | 9/2018 | Schumacher et al. |
| 10,123,875 B2 | 11/2018 | Wildhirt et al. |
| 10,124,102 B2 | 11/2018 | Bulent et al. |
| 10,130,742 B2 | 11/2018 | Tuseth |
| 10,149,932 B2 | 12/2018 | McBride et al. |
| 10,179,197 B2 | 1/2019 | Kaiser et al. |
| 10,183,104 B2 | 1/2019 | Anderson et al. |
| 10,201,645 B2 | 2/2019 | Muller |
| 10,207,037 B2 | 2/2019 | Corbett et al. |
| 10,207,038 B2 | 2/2019 | Neumann |
| 10,220,129 B2 | 3/2019 | Ayre et al. |
| 10,232,099 B2 | 3/2019 | Peters et al. |
| 10,238,782 B2 | 3/2019 | Barry |
| 10,238,783 B2 | 3/2019 | Aboul-Hosn et al. |
| 10,251,986 B2 | 4/2019 | Larose et al. |
| 10,258,771 B2 | 4/2019 | Beissel et al. |
| 10,279,093 B2 | 5/2019 | Reichenbach et al. |
| 10,293,090 B2 | 5/2019 | Bonde et al. |
| 10,300,185 B2 | 5/2019 | Aboul-Hosn et al. |
| 10,300,249 B2 | 5/2019 | Tao et al. |
| 10,322,217 B2 | 6/2019 | Spence |
| 10,342,906 B2 | 7/2019 | D'Ambrosio et al. |
| 10,350,384 B2 | 7/2019 | Farnan et al. |
| 10,357,598 B2 | 7/2019 | Aboul-Hosn et al. |
| 10,361,617 B2 | 7/2019 | Mueller et al. |
| 10,371,150 B2 | 8/2019 | Wu et al. |
| 10,376,162 B2 | 8/2019 | Edelman et al. |
| 10,420,869 B2 | 9/2019 | Cornen |
| 10,434,232 B2 | 10/2019 | Wu et al. |
| 10,441,771 B2 | 10/2019 | Bickhart et al. |
| 10,449,275 B2 | 10/2019 | Corbett |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,542 B2 | 11/2019 | Jahangir |
| 10,493,191 B2 | 12/2019 | Whisenant et al. |
| 10,500,323 B2 | 12/2019 | Heuring et al. |
| 10,512,537 B2 | 12/2019 | Corbett et al. |
| 10,525,178 B2 | 1/2020 | Zeng |
| 10,537,431 B2 | 1/2020 | Zhou et al. |
| 10,537,670 B2 | 1/2020 | Tuseth et al. |
| 10,537,672 B2 | 1/2020 | Tuseth et al. |
| 10,557,475 B2 | 2/2020 | Roehn |
| 10,561,771 B2 | 2/2020 | Heilman et al. |
| 10,561,772 B2 | 2/2020 | Schumacher |
| 10,576,191 B2 | 3/2020 | LaRose |
| 10,576,192 B2 | 3/2020 | Muller et al. |
| 10,576,258 B2 | 3/2020 | Fantuzzi et al. |
| 10,584,589 B2 | 3/2020 | Schumacher et al. |
| 10,589,012 B2 | 3/2020 | Toellner et al. |
| 10,589,013 B2 | 3/2020 | Bourque |
| 10,610,626 B2 | 4/2020 | Spanier et al. |
| 10,617,808 B2 | 4/2020 | Hastie et al. |
| 10,632,241 B2 | 4/2020 | Schenck et al. |
| 10,660,998 B2 | 5/2020 | Hodges |
| 10,662,967 B2 | 5/2020 | Scheckel |
| 10,668,195 B2 | 6/2020 | Flores |
| 10,669,855 B2 | 6/2020 | Toellner et al. |
| 10,709,828 B2 | 7/2020 | Toellner et al. |
| 10,722,631 B2 | 7/2020 | Salahieh et al. |
| 10,737,008 B2 | 8/2020 | Corbett et al. |
| 10,737,086 B2 | 8/2020 | Agrawal et al. |
| 10,773,002 B2 | 9/2020 | Siess et al. |
| 10,780,208 B2 | 9/2020 | Siess et al. |
| 10,806,904 B2 | 10/2020 | Jelle et al. |
| 10,814,053 B2 | 10/2020 | Throckmorton et al. |
| 10,857,273 B2 | 12/2020 | Hodges et al. |
| 10,857,274 B2 | 12/2020 | Alexander et al. |
| 10,864,015 B2 | 12/2020 | Von Segesser |
| 10,864,308 B2 | 12/2020 | Muller et al. |
| 10,881,836 B2 | 1/2021 | Schumacher et al. |
| 10,881,845 B2 | 1/2021 | Siess et al. |
| 10,894,143 B2 | 1/2021 | Yokoyama |
| 10,898,625 B2 | 1/2021 | Toellner |
| 10,953,205 B2 | 3/2021 | Korkuch |
| 10,959,878 B2 | 3/2021 | Wolfertz et al. |
| 10,967,152 B2 | 4/2021 | Korkuch |
| 11,007,350 B2 | 5/2021 | Tao et al. |
| 11,027,114 B2 | 6/2021 | D'Ambrosio et al. |
| 11,033,729 B2 | 6/2021 | Scheckel et al. |
| 11,045,624 B2 | 6/2021 | Oiwa |
| 11,045,634 B2 | 6/2021 | Korkuch et al. |
| 11,045,638 B2 | 6/2021 | Keenan et al. |
| 11,058,851 B2 | 7/2021 | Farnan |
| 11,058,863 B2 | 7/2021 | Demou |
| 11,058,865 B2 | 7/2021 | Fitzgerald et al. |
| 11,065,417 B2 | 7/2021 | Inukai et al. |
| 11,065,434 B2 | 7/2021 | Egler et al. |
| 11,076,884 B2 | 8/2021 | Anderson et al. |
| 11,090,465 B2 | 8/2021 | Weber et al. |
| 11,092,158 B2 | 8/2021 | Siess et al. |
| 11,096,568 B2 | 8/2021 | Harrah et al. |
| 11,097,092 B2 | 8/2021 | Siess et al. |
| 11,103,689 B2 | 8/2021 | Siess et al. |
| 11,103,690 B2 | 8/2021 | Epple |
| 11,107,626 B2 | 8/2021 | Siess et al. |
| 11,116,959 B2 | 9/2021 | Alexander et al. |
| 11,123,538 B2 | 9/2021 | Epple et al. |
| 11,123,539 B2 | 9/2021 | Pfeffer et al. |
| 11,123,541 B2 | 9/2021 | Corbett et al. |
| 11,129,959 B2 | 9/2021 | Hart et al. |
| 11,129,969 B2 | 9/2021 | Pederson, Jr. et al. |
| 11,129,978 B2 | 9/2021 | Pfeffer et al. |
| 11,141,579 B2 | 10/2021 | Steingräber |
| 11,160,970 B2 | 11/2021 | Muller et al. |
| 11,167,124 B2 | 11/2021 | Pfeffer et al. |
| 11,173,295 B2 | 11/2021 | Mack et al. |
| 11,173,297 B2 | 11/2021 | Muller |
| 11,179,557 B2 | 11/2021 | Georges et al. |

(56) References Cited

U.S. PATENT DOCUMENTS

| | | | |
|---|---|---|---|
| 11,185,678 B2 | 11/2021 | Smith et al. |
| 11,185,680 B2 | 11/2021 | Tuval et al. |
| 11,191,927 B2 | 12/2021 | McLaughlin et al. |
| 11,191,944 B2 | 12/2021 | Tuval et al. |
| 11,197,690 B2 | 12/2021 | Fantuzzi et al. |
| 11,197,989 B2 | 12/2021 | Arslan et al. |
| 11,202,901 B2 | 12/2021 | Barry |
| 11,219,755 B2 | 1/2022 | Siess et al. |
| 11,219,756 B2 | 1/2022 | Tanner et al. |
| 11,229,786 B2 | 1/2022 | Zeng et al. |
| 11,235,138 B2 | 2/2022 | Gross-Hardt et al. |
| 11,235,140 B2 | 2/2022 | Siess et al. |
| 11,241,312 B2 | 2/2022 | Simonin |
| 11,241,568 B2 | 2/2022 | Keenan et al. |
| 11,241,569 B2 | 2/2022 | Delgado, III |
| 11,253,693 B2 | 2/2022 | Pfeffer et al. |
| 11,260,212 B2 | 3/2022 | Tuval et al. |
| 11,260,213 B2 | 3/2022 | Zeng et al. |
| 11,260,215 B2 | 3/2022 | Scheckel et al. |
| 11,266,502 B1 | 3/2022 | Wallace |
| 11,273,300 B2 | 3/2022 | Schafir |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,285,309 B2 | 3/2022 | Tuval et al. |
| 11,291,800 B2 | 4/2022 | Yokota |
| 11,291,805 B2 | 4/2022 | Ouchi et al. |
| 11,291,821 B2 | 4/2022 | Agrawal et al. |
| 11,291,824 B2 | 4/2022 | Schwammenthal et al. |
| 11,291,825 B2 | 4/2022 | Tuval et al. |
| 11,291,826 B2 | 4/2022 | Tuval et al. |
| 11,291,855 B2 | 4/2022 | Wiesener |
| 11,298,519 B2 | 4/2022 | Josephy et al. |
| 11,298,520 B2 | 4/2022 | Schwammenthal et al. |
| 11,298,521 B2 | 4/2022 | Schwammenthal et al. |
| 11,298,523 B2 | 4/2022 | Tuval et al. |
| 11,298,524 B2 | 4/2022 | El Katerji et al. |
| 11,298,525 B2 | 4/2022 | Jahangir |
| 11,304,747 B2 | 4/2022 | Simani et al. |
| 11,304,755 B2 | 4/2022 | Cao et al. |
| 11,305,103 B2 | 4/2022 | Larose et al. |
| 11,305,105 B2 | 4/2022 | Corbett et al. |
| 11,311,311 B2 | 4/2022 | Sperry et al. |
| 11,311,711 B2 | 4/2022 | Casas et al. |
| 11,311,712 B2 | 4/2022 | Zeng et al. |
| 11,313,228 B2 | 4/2022 | Schumacher et al. |
| D951,435 S | 5/2022 | Motomura et al. |
| 11,318,284 B2 | 5/2022 | Ishida et al. |
| 11,318,285 B2 | 5/2022 | Ishida |
| 11,318,290 B2 | 5/2022 | Kleinhaus |
| 11,318,295 B2 | 5/2022 | Reyes et al. |
| 11,324,920 B2 | 5/2022 | Inukai et al. |
| 11,324,940 B2 | 5/2022 | Earles et al. |
| 11,324,941 B2 | 5/2022 | Xu et al. |
| 11,331,082 B2 | 5/2022 | Itoh et al. |
| 11,331,450 B2 | 5/2022 | Sakaguchi |
| 11,331,451 B2 | 5/2022 | Yamashita et al. |
| 11,331,465 B2 | 5/2022 | Epple |
| 11,331,466 B2 | 5/2022 | Keen et al. |
| 11,331,467 B2 | 5/2022 | King et al. |
| 11,331,470 B2 | 5/2022 | Muller et al. |
| 11,338,124 B2 | 5/2022 | Pfeffer et al. |
| 11,338,125 B2 | 5/2022 | Liu et al. |
| 11,344,716 B2 | 5/2022 | Taskin |
| 11,344,717 B2 | 5/2022 | Kallenbach et al. |
| 11,351,356 B2 | 6/2022 | Mohl |
| 11,351,357 B2 | 6/2022 | Mohl |
| 11,351,359 B2 | 6/2022 | Clifton et al. |
| 11,357,967 B2 | 6/2022 | Zeng et al. |
| 11,364,363 B2 | 6/2022 | Fantuzzi et al. |
| 11,364,373 B2 | 6/2022 | Corbett et al. |
| 11,368,081 B2 | 6/2022 | Vogt et al. |
| 11,369,413 B2 | 6/2022 | Murphy |
| 11,369,785 B2 | 6/2022 | Callaway et al. |
| 11,369,786 B2 | 6/2022 | Menon et al. |
| 11,376,415 B2 | 7/2022 | Mohl |
| 11,377,512 B2 | 7/2022 | Kuramoto et al. |
| 11,389,633 B2 | 7/2022 | Rohl et al. |
| 11,389,639 B2 | 7/2022 | Casas |
| 11,389,641 B2 | 7/2022 | Nguyen et al. |
| 11,400,261 B2 | 8/2022 | Mathews et al. |
| 11,406,395 B2 | 8/2022 | Wada et al. |
| 11,406,522 B2 | 8/2022 | Folan et al. |
| 11,406,798 B2 | 8/2022 | Kambara |
| 11,406,799 B2 | 8/2022 | McEvaddy et al. |
| 11,413,443 B2 | 8/2022 | Hodges et al. |
| 11,413,446 B2 | 8/2022 | Siess et al. |
| 11,415,150 B2 | 8/2022 | Richert et al. |
| 11,419,721 B2 | 8/2022 | Poppe et al. |
| 11,419,743 B2 | 8/2022 | Poppe et al. |
| 11,421,701 B2 | 8/2022 | Schumacher et al. |
| 11,426,562 B2 | 8/2022 | Fantuzzi |
| 11,428,236 B2 | 8/2022 | McBride et al. |
| 11,433,168 B2 | 9/2022 | Wu et al. |
| 11,434,921 B2 | 9/2022 | McBride et al. |
| 11,434,922 B2 | 9/2022 | Roehn |
| 11,439,791 B2 | 9/2022 | Ishida |
| 11,446,044 B2 | 9/2022 | Bonnette et al. |
| 11,446,414 B2 | 9/2022 | Oiwa |
| 11,446,481 B2 | 9/2022 | Wolman et al. |
| 11,446,482 B2 | 9/2022 | Kirchhoff et al. |
| 11,452,575 B2 | 9/2022 | Morey et al. |
| 11,452,859 B2 | 9/2022 | Earles et al. |
| 11,458,285 B2 | 10/2022 | Graham et al. |
| 11,460,030 B2 | 10/2022 | Shambaugh et al. |
| 11,471,026 B2 | 10/2022 | Piskun et al. |
| 11,471,662 B2 | 10/2022 | Akkerman et al. |
| 11,471,663 B2 | 10/2022 | Tuval et al. |
| 11,471,665 B2 | 10/2022 | Clifton et al. |
| 11,478,627 B2 | 10/2022 | Siess et al. |
| 11,478,628 B2 | 10/2022 | Muller et al. |
| 11,478,629 B2 | 10/2022 | Harjes et al. |
| 11,484,698 B2 | 11/2022 | Radman |
| 11,484,699 B2 | 11/2022 | Tuval et al. |
| 11,486,400 B2 | 11/2022 | Schumacher |
| 11,491,320 B2 | 11/2022 | Siess |
| 11,491,322 B2 | 11/2022 | Muller et al. |
| 11,497,889 B2 | 11/2022 | Mixter et al. |
| 11,497,894 B2 | 11/2022 | Korkuch et al. |
| 11,497,896 B2 | 11/2022 | Tanner et al. |
| 11,497,906 B2 | 11/2022 | Grace et al. |
| 11,503,993 B2 | 11/2022 | Chu et al. |
| 11,504,102 B2 | 11/2022 | Stanton et al. |
| 11,511,083 B2 | 11/2022 | Wada |
| 11,511,084 B2 | 11/2022 | Chu |
| 11,511,098 B2 | 11/2022 | Agrawal et al. |
| 11,511,101 B2 | 11/2022 | Hastie et al. |
| 11,511,103 B2 | 11/2022 | Salahieh et al. |
| 11,511,104 B2 | 11/2022 | Dur et al. |
| 11,517,191 B2 | 12/2022 | Oskin |
| 11,517,720 B2 | 12/2022 | Korkuch et al. |
| 11,517,726 B2 | 12/2022 | Siess et al. |
| 11,517,736 B2 | 12/2022 | Earles et al. |
| 11,517,737 B2 | 12/2022 | Struthers et al. |
| 11,517,738 B2 | 12/2022 | Wisniewski |
| 11,517,739 B2 | 12/2022 | Toellner |
| 11,517,740 B2 | 12/2022 | Agarwa et al. |
| 11,523,905 B2 | 12/2022 | Griswold et al. |
| 11,524,137 B2 | 12/2022 | Jahangir |
| 11,524,153 B2 | 12/2022 | Alexander et al. |
| 11,524,165 B2 | 12/2022 | Tan et al. |
| 11,529,062 B2 | 12/2022 | Moyer et al. |
| 11,529,510 B2 | 12/2022 | Leven |
| 11,534,596 B2 | 12/2022 | Schafir et al. |
| 11,540,857 B2 | 1/2023 | Olson et al. |
| 11,564,710 B2 | 1/2023 | Fitterer et al. |
| 11,565,093 B2 | 1/2023 | Kirt et al. |
| 11,565,103 B2 | 1/2023 | Farago et al. |
| 11,569,015 B2 | 1/2023 | Mourran et al. |
| 11,572,879 B2 | 2/2023 | Mohl |
| 11,577,067 B2 | 2/2023 | Breidall et al. |
| 11,577,068 B2 | 2/2023 | Spence et al. |
| 11,583,659 B2 | 2/2023 | Pfeffer et al. |
| 11,583,670 B2 | 2/2023 | Pfeifer et al. |

(56) References Cited

U.S. PATENT DOCUMENTS

| | | | |
|---|---|---|---|
| 11,583,671 | B2 | 2/2023 | Nguyen et al. |
| 11,583,672 | B2 | 2/2023 | Weber et al. |
| 11,590,336 | B2 | 2/2023 | Harjes et al. |
| 11,590,337 | B2 | 2/2023 | Granegger et al. |
| 11,590,338 | B2 | 2/2023 | Barry |
| 11,592,028 | B2 | 2/2023 | Schumacher et al. |
| 11,596,727 | B2 | 3/2023 | Siess et al. |
| 11,602,448 | B2 | 3/2023 | Nygaard et al. |
| 11,602,627 | B2 | 3/2023 | Leonhardt |
| 11,617,876 | B2 | 4/2023 | Scheckel et al. |
| 11,628,280 | B2 | 4/2023 | Schumacher et al. |
| 11,628,293 | B2 | 4/2023 | Gandhi et al. |
| 11,632,015 | B2 | 4/2023 | Sconzert et al. |
| 11,633,574 | B2 | 4/2023 | Watanabe |
| 11,633,586 | B2 | 4/2023 | Tanner et al. |
| 11,638,813 | B2 | 5/2023 | West |
| 11,639,722 | B2 | 5/2023 | Medvedev et al. |
| 11,642,511 | B2 | 5/2023 | Delgado, III |
| 11,648,387 | B2 | 5/2023 | Schwammenthal et al. |
| 11,648,388 | B2 | 5/2023 | Siess et al. |
| 11,648,389 | B2 | 5/2023 | Wang et al. |
| 11,648,390 | B2 | 5/2023 | Spanier et al. |
| 11,648,391 | B2 | 5/2023 | Schwammenthal et al. |
| 11,648,392 | B2 | 5/2023 | Tuval et al. |
| 11,648,393 | B2 | 5/2023 | Taskin et al. |
| 11,654,273 | B2 | 5/2023 | Granegger et al. |
| 11,654,275 | B2 | 5/2023 | Brandt |
| 11,654,276 | B2 | 5/2023 | Fitzgerald et al. |
| 11,660,434 | B2 | 5/2023 | Korkuch et al. |
| 11,660,441 | B2 | 5/2023 | Fitzgerald et al. |
| 11,666,747 | B2 | 6/2023 | Tuval et al. |
| 11,666,748 | B2 | 6/2023 | Kronstedt et al. |
| 11,668,321 | B2 | 6/2023 | Richert et al. |
| 11,674,517 | B2 | 6/2023 | Mohl |
| 11,679,234 | B2 | 6/2023 | King et al. |
| 11,679,249 | B2 | 6/2023 | Scheckel et al. |
| 11,679,250 | B2 | 6/2023 | Alexander et al. |
| 11,684,275 | B2 | 6/2023 | Tuval et al. |
| 11,684,769 | B2 | 6/2023 | Harjes et al. |
| 11,690,521 | B2 | 7/2023 | Tuval et al. |
| 11,690,606 | B2 | 7/2023 | Muller et al. |
| 11,690,979 | B2 | 7/2023 | Voss et al. |
| 11,690,996 | B2 | 7/2023 | Siess et al. |
| 11,690,997 | B2 | 7/2023 | Georges et al. |
| 11,697,002 | B2 | 7/2023 | Korkuch |
| 11,697,016 | B2 | 7/2023 | Epple |
| 11,701,510 | B2 | 7/2023 | Demou |
| 11,702,938 | B2 | 7/2023 | Schumacher et al. |
| 11,703,064 | B2 | 7/2023 | Bredenbreuker et al. |
| 11,708,833 | B2 | 7/2023 | McBride et al. |
| 11,730,939 | B2 | 8/2023 | Siess et al. |
| 11,730,942 | B2 | 8/2023 | Fantuzzi et al. |
| D998,799 | S | 9/2023 | Okamura et al. |
| 11,744,567 | B2 | 9/2023 | Deuel et al. |
| 11,744,638 | B2 | 9/2023 | Davies et al. |
| 11,744,987 | B2 | 9/2023 | Siess et al. |
| 11,745,005 | B2 | 9/2023 | Delgado, III |
| 11,746,906 | B1 | 9/2023 | Balta et al. |
| 11,751,751 | B2 | 9/2023 | Calabrese et al. |
| 11,751,753 | B2 | 9/2023 | Levasseur et al. |
| 11,752,308 | B2 | 9/2023 | Tao et al. |
| 11,752,322 | B2 | 9/2023 | Aboulhosn et al. |
| 11,752,323 | B2 | 9/2023 | Edwards et al. |
| 11,754,075 | B2 | 9/2023 | Schuelke et al. |
| 11,754,077 | B1 | 9/2023 | Mohl |
| 11,759,610 | B2 | 9/2023 | Calabrese et al. |
| 11,759,612 | B2 | 9/2023 | Tanner et al. |
| 11,759,622 | B2 | 9/2023 | Siess et al. |
| 11,766,264 | B2 | 9/2023 | Phan et al. |
| 11,766,555 | B2 | 9/2023 | Matthes et al. |
| 11,771,444 | B2 | 10/2023 | Crawford et al. |
| 11,771,884 | B2 | 10/2023 | Siess et al. |
| 11,771,885 | B2 | 10/2023 | Liu et al. |
| 11,779,194 | B2 | 10/2023 | Wilder et al. |
| 11,779,234 | B2 | 10/2023 | Harjes et al. |
| 11,779,338 | B2 | 10/2023 | Gordon et al. |
| 11,779,361 | B2 | 10/2023 | Kugler et al. |
| 11,779,729 | B2 | 10/2023 | Guimaraes et al. |
| 11,779,743 | B2 | 10/2023 | Agrawal et al. |
| 11,779,751 | B2 | 10/2023 | Earles et al. |
| 11,781,551 | B2 | 10/2023 | Yanai et al. |
| 11,786,109 | B2 | 10/2023 | Golden et al. |
| 11,786,386 | B2 | 10/2023 | Brady et al. |
| 11,786,700 | B2 | 10/2023 | Pfeffer et al. |
| 11,786,701 | B2 | 10/2023 | Maki et al. |
| 11,786,720 | B2 | 10/2023 | Muller |
| 11,793,530 | B2 | 10/2023 | Chu et al. |
| 11,793,977 | B2 | 10/2023 | Korkuch et al. |
| 11,793,994 | B2 | 10/2023 | Josephy et al. |
| 11,804,767 | B2 | 10/2023 | Vogt et al. |
| 11,806,046 | B2 | 11/2023 | Fantuzzi et al. |
| 11,806,116 | B2 | 11/2023 | Tuval et al. |
| 11,806,117 | B2 | 11/2023 | Tuval et al. |
| 11,806,258 | B2 | 11/2023 | Hingston et al. |
| 11,806,517 | B2 | 11/2023 | Petersen |
| 11,806,518 | B2 | 11/2023 | Michelena et al. |
| 11,812,944 | B2 | 11/2023 | Wales et al. |
| 11,812,951 | B2 | 11/2023 | Mitelberg et al. |
| 11,812,952 | B2 | 11/2023 | Abbott et al. |
| 11,813,183 | B2 | 11/2023 | Christakis et al. |
| 11,813,443 | B2 | 11/2023 | Hanson et al. |
| 11,813,444 | B2 | 11/2023 | Siess et al. |
| 11,813,445 | B2 | 11/2023 | Alexander et al. |
| 11,819,678 | B2 | 11/2023 | Siess et al. |
| 11,826,127 | B2 | 11/2023 | Casas |
| 11,826,517 | B2 | 11/2023 | Fuller et al. |
| 11,832,793 | B2 | 12/2023 | McWeeney et al. |
| 11,832,868 | B2 | 12/2023 | Smail et al. |
| 11,833,278 | B2 | 12/2023 | Siess et al. |
| 11,833,314 | B2 | 12/2023 | Corbett et al. |
| 11,833,316 | B2 | 12/2023 | Hayakawa et al. |
| 11,833,342 | B2 | 12/2023 | Tanner et al. |
| 11,839,754 | B2 | 12/2023 | Tuval et al. |
| 11,844,592 | B2 | 12/2023 | Tuval et al. |
| 11,844,909 | B2 | 12/2023 | Tassoni et al. |
| 11,844,940 | B2 | 12/2023 | D'Ambrosio et al. |
| 11,850,373 | B2 | 12/2023 | Golden et al. |
| 11,850,412 | B2 | 12/2023 | Grauwinkel et al. |
| 11,850,413 | B2 | 12/2023 | Zeng et al. |
| 11,850,414 | B2 | 12/2023 | Schenck et al. |
| 11,850,415 | B2 | 12/2023 | Schwammenthal et al. |
| 11,857,159 | B2 | 1/2024 | Saenz Villalobos et al. |
| 11,857,161 | B2 | 1/2024 | Nguyen et al. |
| 11,857,197 | B2 | 1/2024 | Alexander et al. |
| 11,857,740 | B2 | 1/2024 | Chu |
| 11,857,743 | B2 | 1/2024 | Fantuzzi et al. |
| 11,857,777 | B2 | 1/2024 | Earles et al. |
| 11,864,746 | B2 | 1/2024 | Melilli et al. |
| 11,865,238 | B2 | 1/2024 | Siess et al. |
| 11,865,275 | B2 | 1/2024 | O'Carrol et al. |
| 11,871,962 | B2 | 1/2024 | Tehrani et al. |
| 11,872,384 | B2 | 1/2024 | Cotter |
| 11,877,753 | B2 | 1/2024 | Connolly et al. |
| 11,878,131 | B2 | 1/2024 | Pedersen et al. |
| 11,883,005 | B2 | 1/2024 | Golden et al. |
| 11,883,062 | B2 | 1/2024 | Rawson |
| 11,883,207 | B2 | 1/2024 | El Katerji et al. |
| 11,883,274 | B2 | 1/2024 | Schwammenthal et al. |
| 11,883,310 | B2 | 1/2024 | Nolan et al. |
| 11,883,641 | B2 | 1/2024 | Dur et al. |
| D1,015,536 | S | 2/2024 | Walsh |
| 11,890,085 | B2 | 2/2024 | Duval et al. |
| 11,890,212 | B2 | 2/2024 | Gilmartin et al. |
| 11,890,428 | B2 | 2/2024 | Ito |
| 11,890,435 | B2 | 2/2024 | Takagi |
| 11,896,474 | B2 | 2/2024 | Hynes et al. |
| 11,896,482 | B2 | 2/2024 | Delaloye et al. |
| 11,896,814 | B2 | 2/2024 | Shambaugh, Jr. |
| 11,898,642 | B2 | 2/2024 | Stanton et al. |
| 11,903,589 | B2 | 2/2024 | Stahman et al. |
| 11,903,600 | B2 | 2/2024 | Chu et al. |
| 11,903,831 | B2 | 2/2024 | Shuey et al. |
| 11,903,857 | B2 | 2/2024 | Folan |
| 11,904,104 | B2 | 2/2024 | Jahangir |

(56) References Cited

U.S. PATENT DOCUMENTS

| | | | |
|---|---|---|---|
| 11,911,072 B2 | 2/2024 | Fantuzzi et al. |
| 11,911,305 B2 | 2/2024 | Smith et al. |
| 11,911,579 B2 | 2/2024 | Tanner et al. |
| 11,918,186 B2 | 3/2024 | Chu et al. |
| 11,918,187 B2 | 3/2024 | Cahill et al. |
| 11,918,202 B2 | 3/2024 | Deuel et al. |
| 11,918,219 B2 | 3/2024 | Smith et al. |
| 11,918,470 B2 | 3/2024 | Jarral et al. |
| 11,918,496 B2 | 3/2024 | Folan |
| 11,918,726 B2 | 3/2024 | Siess et al. |
| 11,918,752 B2 | 3/2024 | Tassoni et al. |
| 11,918,764 B2 | 3/2024 | Soltis et al. |
| 11,918,780 B2 | 3/2024 | Jagelski et al. |
| 11,918,800 B2 | 3/2024 | Muller et al. |
| 11,925,315 B2 | 3/2024 | Chu et al. |
| 11,925,356 B2 | 3/2024 | Anderson et al. |
| 11,925,383 B2 | 3/2024 | Tada et al. |
| 11,925,386 B2 | 3/2024 | Favreau |
| 11,925,570 B2 | 3/2024 | Lydecker et al. |
| 11,925,794 B2 | 3/2024 | Malkin et al. |
| 11,925,795 B2 | 3/2024 | Muller et al. |
| 11,925,796 B2 | 3/2024 | Tanner et al. |
| 11,925,797 B2 | 3/2024 | Tanner et al. |
| 11,930,996 B2 | 3/2024 | Dresher |
| 11,930,997 B2 | 3/2024 | Melito et al. |
| 11,931,003 B2 | 3/2024 | Congdon et al. |
| 11,931,058 B2 | 3/2024 | Spangler et al. |
| 11,931,068 B2 | 3/2024 | Fitterer et al. |
| 11,931,073 B2 | 3/2024 | Walsh et al. |
| 11,931,098 B2 | 3/2024 | Moriyama |
| 11,931,278 B2 | 3/2024 | Wood et al. |
| 11,931,528 B2 | 3/2024 | Rohl et al. |
| 11,931,530 B2 | 3/2024 | Campbell et al. |
| 11,937,774 B2 | 3/2024 | Wood et al. |
| 11,937,871 B2 | 3/2024 | Crawford et al. |
| 11,938,047 B2 | 3/2024 | Christakis et al. |
| 11,938,285 B2 | 3/2024 | Lau et al. |
| 11,938,311 B2 | 3/2024 | Corbett et al. |
| 11,944,805 B2 | 4/2024 | Stotz |
| 11,957,892 B2 | 4/2024 | Siess et al. |
| D1,028,246 S | 5/2024 | Delorenzo |
| 11,980,385 B2 | 5/2024 | Haselman |
| 11,986,602 B2 | 5/2024 | Corbett |
| 11,986,604 B2 | 5/2024 | Siess |
| 12,005,248 B2 | 6/2024 | Vogt et al. |
| 12,011,583 B2 | 6/2024 | Wang |
| 12,017,058 B2 | 6/2024 | Kerkhoffs et al. |
| 12,017,076 B2 | 6/2024 | Tan et al. |
| 12,023,476 B2 | 7/2024 | Tuval et al. |
| 12,023,477 B2 | 7/2024 | Siess |
| 12,053,624 B2 | 8/2024 | Alexander et al. |
| 12,059,559 B2 | 8/2024 | Muller et al. |
| 12,064,120 B2 | 8/2024 | Hajjar et al. |
| 12,064,611 B2 | 8/2024 | D'Ambrosio et al. |
| 12,064,614 B2 | 8/2024 | Agah et al. |
| 12,064,615 B2 | 8/2024 | Stotz et al. |
| 12,064,616 B2 | 8/2024 | Spanier et al. |
| 12,076,497 B2 | 9/2024 | Fantuzzi et al. |
| 12,076,544 B2 | 9/2024 | Siess et al. |
| 12,076,549 B2 | 9/2024 | Stotz et al. |
| 12,076,550 B2 | 9/2024 | Edwards et al. |
| 12,090,310 B2 | 9/2024 | Alexander et al. |
| 12,090,314 B2 | 9/2024 | Tuval et al. |
| 12,092,114 B2 | 9/2024 | Siess |
| 12,097,016 B2 | 9/2024 | Goldvasser |
| 12,102,815 B2 | 10/2024 | Dhaliwal et al. |
| 12,104,600 B2 | 10/2024 | Mohl |
| 12,107,474 B2 | 10/2024 | Vollmer |
| 12,117,007 B1 | 10/2024 | Mohl |
| 12,121,681 B2 | 10/2024 | Korkuch |
| 12,121,713 B2 | 10/2024 | Calomeni et al. |
| 12,133,976 B2 | 11/2024 | Malone et al. |
| 12,138,438 B2 | 11/2024 | Alexander et al. |
| 12,144,936 B2 | 11/2024 | Tao et al. |
| 12,144,976 B2 | 11/2024 | Baumbach et al. |
| 12,151,092 B2 | 11/2024 | Alexander et al. |
| 12,161,854 B2 | 12/2024 | Earles et al. |
| 12,161,855 B2 | 12/2024 | Hastie et al. |
| 12,161,857 B2 | 12/2024 | Saul et al. |
| 12,171,993 B2 | 12/2024 | Higgins et al. |
| 12,186,517 B2 | 1/2025 | Modlish et al. |
| 12,194,287 B2 | 1/2025 | Kassel et al. |
| 12,196,210 B2 | 1/2025 | Siess et al. |
| 12,201,823 B2 | 1/2025 | Baumbach et al. |
| 12,207,906 B2 | 1/2025 | Tuval et al. |
| 12,213,771 B2 | 2/2025 | Curran et al. |
| 12,233,224 B2 | 2/2025 | Korkuch et al. |
| 12,233,251 B2 | 2/2025 | Siess et al. |
| 12,239,799 B2 | 3/2025 | Corbett et al. |
| 12,241,480 B2 | 3/2025 | Corbett et al. |
| 12,263,330 B2 | 4/2025 | D'Ambrosio et al. |
| 12,263,333 B2 | 4/2025 | Stotz et al. |
| 12,263,334 B2 | 4/2025 | Corbett et al. |
| 12,268,860 B1 | 4/2025 | Fishman et al. |
| 12,268,861 B2 | 4/2025 | D'Ambrosio et al. |
| 12,290,673 B2 | 5/2025 | Jahangir |
| 12,290,676 B2 | 5/2025 | Farago et al. |
| 12,296,134 B2 | 5/2025 | Siess et al. |
| 12,303,678 B2 | 5/2025 | Kerkhoffs et al. |
| 12,303,680 B2 | 5/2025 | Siess et al. |
| 12,318,551 B2 | 6/2025 | Jahangir |
| 12,318,560 B2 | 6/2025 | O'Carrol et al. |
| 12,329,958 B2 | 6/2025 | Siess et al. |
| 12,337,163 B2 | 6/2025 | Radman |
| 12,343,516 B2 | 7/2025 | Cook |
| 12,343,518 B2 | 7/2025 | Tuval et al. |
| 12,343,519 B2 | 7/2025 | Siess et al. |
| 12,357,801 B2 | 7/2025 | Korkuch et al. |
| 12,364,799 B2 | 7/2025 | Siess et al. |
| 12,364,850 B2 | 7/2025 | Siess et al. |
| 12,364,854 B2 | 7/2025 | Wang |
| 12,369,944 B2 | 7/2025 | Fantuzzi et al. |
| 12,370,357 B2 | 7/2025 | Corbett et al. |
| D1,090,825 S | 8/2025 | Loughlin et al. |
| D1,090,829 S | 8/2025 | Loughlin et al. |
| 12,383,704 B2 | 8/2025 | Ship et al. |
| 12,383,724 B2 | 8/2025 | Kirchoff et al. |
| 12,383,727 B2 | 8/2025 | Kassel et al. |
| 12,390,633 B2 | 8/2025 | Stotz et al. |
| 12,397,146 B2 | 8/2025 | Hart et al. |
| D1,092,716 S | 9/2025 | Bernazani |
| 12,402,910 B2 | 9/2025 | Korkuch |
| 12,403,287 B2 | 9/2025 | Tao et al. |
| 12,403,296 B2 | 9/2025 | Baumbach et al. |
| 12,409,299 B2 | 9/2025 | Fantuzzi et al. |
| 12,409,311 B2 | 9/2025 | Jahangir et al. |
| 12,415,056 B2 | 9/2025 | Siess et al. |
| 12,420,076 B2 | 9/2025 | Spanier et al. |
| 12,420,079 B2 | 9/2025 | Das et al. |
| 12,434,060 B2 | 10/2025 | Tan et al. |
| 12,440,663 B2 | 10/2025 | Tuval et al. |
| 12,440,665 B2 | 10/2025 | Tuval et al. |
| 12,447,309 B2 | 10/2025 | Siess et al. |
| 12,447,316 B2 | 10/2025 | Voss et al. |
| 12,447,327 B2 | 10/2025 | Stotz |
| 12,453,847 B2 | 10/2025 | Scheffler et al. |
| 12,453,848 B2 | 10/2025 | Tuval et al. |
| 12,453,849 B2 | 10/2025 | Vancamp et al. |
| D1,101,157 S | 11/2025 | Qi et al. |
| 12,458,792 B2 | 11/2025 | Zarins |
| 12,465,744 B2 | 11/2025 | Schuelke et al. |
| 2001/0009645 A1 | 7/2001 | Noda |
| 2001/0041934 A1 | 11/2001 | Yamazaki et al. |
| 2002/0052638 A1 | 5/2002 | Zadno-Azizi |
| 2002/0076322 A1 | 6/2002 | Maeda et al. |
| 2002/0077600 A1 | 6/2002 | Sirimanne |
| 2002/0082585 A1 | 6/2002 | Carroll et al. |
| 2002/0107482 A1 | 8/2002 | Rocamora et al. |
| 2002/0147495 A1 | 10/2002 | Petroff |
| 2002/0153664 A1 | 10/2002 | Schroeder |
| 2003/0032941 A1 | 2/2003 | Boyle et al. |
| 2003/0060685 A1 | 3/2003 | Houser |
| 2003/0091450 A1 | 5/2003 | Davis et al. |
| 2003/0100816 A1 | 5/2003 | Siess |

(56)                    References Cited

U.S. PATENT DOCUMENTS

| | | |
|---|---|---|
| 2003/0111800 A1 | 6/2003 | Kreutzer |
| 2003/0139643 A1 | 7/2003 | Smith et al. |
| 2003/0191357 A1 | 10/2003 | Frazier |
| 2003/0199727 A1 | 10/2003 | Burke |
| 2004/0034411 A1 | 2/2004 | Quijano |
| 2004/0044266 A1 | 3/2004 | Siess et al. |
| 2004/0102674 A1 | 5/2004 | Zadini et al. |
| 2004/0115038 A1 | 6/2004 | Nuesser et al. |
| 2004/0167376 A1 | 8/2004 | Peters et al. |
| 2004/0234391 A1 | 11/2004 | Izraelev |
| 2004/0241019 A1 | 12/2004 | Goldowsky |
| 2004/0260346 A1 | 12/2004 | Overall et al. |
| 2005/0006083 A1 | 1/2005 | Chen et al. |
| 2005/0008509 A1 | 1/2005 | Chang |
| 2005/0019167 A1 | 1/2005 | Nusser et al. |
| 2005/0085683 A1 | 4/2005 | Bolling et al. |
| 2005/0182435 A1 | 8/2005 | Andrews et al. |
| 2005/0220636 A1 | 10/2005 | Henein et al. |
| 2005/0254976 A1 | 11/2005 | Carrier et al. |
| 2005/0272975 A1 | 12/2005 | McWeeney |
| 2006/0030809 A1 | 2/2006 | Barzilay et al. |
| 2006/0062672 A1 | 3/2006 | McBride et al. |
| 2006/0155158 A1 | 7/2006 | Aboul-Hosn |
| 2006/0224110 A1 | 10/2006 | Scott et al. |
| 2006/0276682 A1 | 12/2006 | Bolling et al. |
| 2007/0004959 A1 | 1/2007 | Carrier et al. |
| 2007/0142696 A1 | 6/2007 | Crosby et al. |
| 2007/0156006 A1 | 7/2007 | Smith et al. |
| 2008/0015517 A1 | 1/2008 | Geistert et al. |
| 2008/0058925 A1 | 3/2008 | Cohen |
| 2008/0086027 A1 | 4/2008 | Siess et al. |
| 2008/0097293 A1 | 4/2008 | Chin et al. |
| 2008/0097386 A1 | 4/2008 | Osypka |
| 2008/0114339 A1 | 5/2008 | McBride et al. |
| 2008/0183136 A1 | 7/2008 | Lenker et al. |
| 2008/0262289 A1 | 10/2008 | Goldowsky |
| 2008/0269822 A1 | 10/2008 | Ljungstrom et al. |
| 2008/0292478 A1 | 11/2008 | Baykut et al. |
| 2008/0306328 A1 | 12/2008 | Ercolani |
| 2009/0004037 A1 | 1/2009 | Ito |
| 2009/0054840 A1 | 2/2009 | Drake et al. |
| 2009/0069886 A1 | 3/2009 | Suri et al. |
| 2009/0112312 A1 | 4/2009 | Larose et al. |
| 2009/0182200 A1 | 7/2009 | Golden |
| 2009/0203957 A1 | 8/2009 | LaRose et al. |
| 2009/0204205 A1 | 8/2009 | Larose et al. |
| 2010/0041939 A1 | 2/2010 | Siess |
| 2010/0082099 A1 | 4/2010 | Vodermayer et al. |
| 2010/0191035 A1 | 7/2010 | Kang et al. |
| 2010/0268017 A1 | 10/2010 | Siess |
| 2010/0298625 A1 | 11/2010 | Reichenbach et al. |
| 2011/0034874 A1 | 2/2011 | Reitan |
| 2011/0124962 A1 | 5/2011 | Gordin |
| 2011/0172505 A1 | 7/2011 | Kim |
| 2011/0184224 A1 | 7/2011 | Garrigue |
| 2011/0230821 A1 | 9/2011 | Babic |
| 2011/0237863 A1 | 9/2011 | Ricci et al. |
| 2011/0238172 A1 | 9/2011 | Akdis |
| 2011/0282274 A1 | 11/2011 | Fulton, III |
| 2012/0029265 A1 | 2/2012 | LaRose |
| 2012/0035645 A1 | 2/2012 | Gross |
| 2012/0088954 A1 | 4/2012 | Foster |
| 2012/0093628 A1 | 4/2012 | Liebing |
| 2012/0134793 A1 | 5/2012 | Wu et al. |
| 2012/0172655 A1 | 7/2012 | Campbell et al. |
| 2012/0178986 A1 | 7/2012 | Campbell et al. |
| 2012/0221021 A1 | 8/2012 | Hoarau et al. |
| 2012/0245404 A1 | 9/2012 | Smith |
| 2012/0247200 A1 | 10/2012 | Ahonen et al. |
| 2012/0283506 A1 | 11/2012 | Meister et al. |
| 2012/0296313 A1 | 11/2012 | Andreacchi et al. |
| 2012/0310036 A1 | 12/2012 | Peters et al. |
| 2013/0053623 A1 | 2/2013 | Evans |
| 2013/0085318 A1 | 4/2013 | Toellner |
| 2013/0209292 A1 | 8/2013 | Baykut et al. |
| 2013/0211324 A1 | 8/2013 | Voss et al. |
| 2013/0281761 A1 | 10/2013 | Kapur |
| 2013/0289376 A1 | 10/2013 | Lang |
| 2013/0303830 A1 | 11/2013 | Zeng et al. |
| 2013/0303831 A1 | 11/2013 | Evans |
| 2013/0303832 A1 | 11/2013 | Wampler |
| 2013/0303970 A1 | 11/2013 | Keenan et al. |
| 2013/0330219 A1 | 12/2013 | LaRose et al. |
| 2014/0005467 A1 | 1/2014 | Farnan et al. |
| 2014/0030122 A1 | 1/2014 | Ozaki |
| 2014/0051908 A1 | 2/2014 | Khanal et al. |
| 2014/0079557 A1 | 3/2014 | LaRose et al. |
| 2014/0107399 A1 | 4/2014 | Spence |
| 2014/0167545 A1 | 6/2014 | Bremner et al. |
| 2014/0180250 A1 | 6/2014 | Belson |
| 2014/0194717 A1 | 7/2014 | Wildhirt et al. |
| 2014/0200389 A1 | 7/2014 | Yanai et al. |
| 2014/0207232 A1 | 7/2014 | Garrigue |
| 2014/0275721 A1 | 9/2014 | Yanai et al. |
| 2014/0330069 A1 | 11/2014 | Hastings et al. |
| 2014/0341726 A1 | 11/2014 | Wu et al. |
| 2014/0368942 A1 | 12/2014 | Harrell |
| 2015/0031936 A1 | 1/2015 | LaRose et al. |
| 2015/0045696 A1 | 2/2015 | Osypka |
| 2015/0051435 A1 | 2/2015 | Siess et al. |
| 2015/0051438 A1 | 2/2015 | Taskin |
| 2015/0066082 A1 | 3/2015 | Moshe |
| 2015/0080743 A1 | 3/2015 | Siess |
| 2015/0090372 A1 | 4/2015 | Branagan et al. |
| 2015/0099923 A1 | 4/2015 | Magovern et al. |
| 2015/0119633 A1 | 4/2015 | Haselby et al. |
| 2015/0141738 A1 | 5/2015 | Toellner et al. |
| 2015/0141842 A1 | 5/2015 | Spanier et al. |
| 2015/0151087 A1 | 6/2015 | Suzuki et al. |
| 2015/0171694 A1 | 6/2015 | Dallas |
| 2015/0190092 A1 | 7/2015 | Mori |
| 2015/0273184 A1 | 10/2015 | Scott et al. |
| 2015/0290372 A1 | 10/2015 | Muller et al. |
| 2015/0290373 A1 | 10/2015 | Rudser et al. |
| 2015/0290432 A1 | 10/2015 | Mathews et al. |
| 2015/0306291 A1 | 10/2015 | Bonde et al. |
| 2015/0343179 A1 | 12/2015 | Schumacher et al. |
| 2015/0359952 A1 | 12/2015 | Andrus et al. |
| 2015/0362017 A1 | 12/2015 | Bell |
| 2015/0365738 A1 | 12/2015 | Purvis et al. |
| 2016/0008531 A1 | 1/2016 | Wang et al. |
| 2016/0030649 A1 | 2/2016 | Zeng |
| 2016/0038663 A1 | 2/2016 | Taskin et al. |
| 2016/0045654 A1 | 2/2016 | Connor |
| 2016/0067395 A1 | 3/2016 | Jimenez et al. |
| 2016/0095744 A1 | 4/2016 | Wolfertz et al. |
| 2016/0101224 A1 | 4/2016 | Akkerman |
| 2016/0144089 A1 | 5/2016 | Woo et al. |
| 2016/0144166 A1 | 5/2016 | Decréet al. |
| 2016/0166747 A1 | 6/2016 | Frazier et al. |
| 2016/0213828 A1 | 7/2016 | Sievers |
| 2016/0223086 A1 | 8/2016 | Balsells et al. |
| 2016/0256620 A1 | 9/2016 | Scheckel et al. |
| 2016/0271309 A1 | 9/2016 | Throckmorton et al. |
| 2016/0279311 A1 | 9/2016 | Cecere et al. |
| 2016/0367739 A1 | 12/2016 | Wiesener et al. |
| 2016/0375187 A1 | 12/2016 | Lee et al. |
| 2017/0021069 A1 | 1/2017 | Hodges |
| 2017/0021074 A1 | 1/2017 | Opfermann et al. |
| 2017/0035952 A1 | 2/2017 | Muller |
| 2017/0043074 A1 | 2/2017 | Siess |
| 2017/0049947 A1 | 2/2017 | Corbett et al. |
| 2017/0065267 A1 | 3/2017 | Fantuzzi et al. |
| 2017/0080136 A1 | 3/2017 | Janeczek et al. |
| 2017/0080199 A1 | 3/2017 | Murphy |
| 2017/0087286 A1 | 3/2017 | Spanier et al. |
| 2017/0087288 A1 | 3/2017 | Groß-Hardt et al. |
| 2017/0128644 A1 | 5/2017 | Foster |
| 2017/0136225 A1 | 5/2017 | Siess et al. |
| 2017/0143938 A1 | 5/2017 | Ogle et al. |
| 2017/0143952 A1 | 5/2017 | Siess et al. |
| 2017/0157309 A1 | 6/2017 | Begg et al. |
| 2017/0209099 A1 | 7/2017 | Caron et al. |
| 2017/0209633 A1 | 7/2017 | Cohen |

(56) References Cited

U.S. PATENT DOCUMENTS

| 2017/0215918 A1 | 8/2017 | Tao et al. |
| 2017/0232169 A1* | 8/2017 | Muller ................ A61M 60/829 |
| | | 600/16 |
| 2017/0232170 A1 | 8/2017 | Jarvik |
| 2017/0232171 A1 | 8/2017 | Roehn et al. |
| 2017/0274128 A1 | 9/2017 | Tamburino et al. |
| 2017/0312492 A1 | 11/2017 | Fantuzzi et al. |
| 2017/0317573 A1 | 11/2017 | Mueller et al. |
| 2017/0333607 A1 | 11/2017 | Zarins |
| 2017/0333608 A1 | 11/2017 | Zeng |
| 2017/0340787 A1 | 11/2017 | Corbett et al. |
| 2017/0340788 A1 | 11/2017 | Korakianitis et al. |
| 2017/0340789 A1 | 11/2017 | Bonde et al. |
| 2017/0343043 A1 | 11/2017 | Walsh et al. |
| 2017/0368245 A1 | 12/2017 | Kantrowitz et al. |
| 2018/0001003 A1 | 1/2018 | Moran et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0050141 A1 | 2/2018 | Corbett et al. |
| 2018/0055979 A1 | 3/2018 | Corbett et al. |
| 2018/0064860 A1 | 3/2018 | Nunez et al. |
| 2018/0093070 A1 | 4/2018 | Cottone |
| 2018/0099076 A1 | 4/2018 | LaRose |
| 2018/0099078 A1 | 4/2018 | Tuseth et al. |
| 2018/0104397 A1 | 4/2018 | Schumacher |
| 2018/0110907 A1 | 4/2018 | Keenan et al. |
| 2018/0133379 A1 | 5/2018 | Farnan et al. |
| 2018/0154058 A1 | 6/2018 | Menon et al. |
| 2018/0169312 A1 | 6/2018 | Barry |
| 2018/0169313 A1 | 6/2018 | Schwammenthal et al. |
| 2018/0200422 A1 | 7/2018 | Nguyen et al. |
| 2018/0207334 A1 | 7/2018 | Siess |
| 2018/0207336 A1 | 7/2018 | Solem |
| 2018/0219452 A1 | 8/2018 | Boisclair |
| 2018/0221551 A1 | 8/2018 | Tanner et al. |
| 2018/0221553 A1 | 8/2018 | Taskin |
| 2018/0228950 A1 | 8/2018 | Janeczek et al. |
| 2018/0228953 A1 | 8/2018 | Siess et al. |
| 2018/0243004 A1 | 8/2018 | von Segesser et al. |
| 2018/0243489 A1 | 8/2018 | Haddadi |
| 2018/0250456 A1 | 9/2018 | Nitzan et al. |
| 2018/0256797 A1 | 9/2018 | Schenck et al. |
| 2018/0280598 A1 | 10/2018 | Curran et al. |
| 2018/0289877 A1 | 10/2018 | Schumacher et al. |
| 2018/0296742 A1 | 10/2018 | Toellner |
| 2018/0303990 A1 | 10/2018 | Siess et al. |
| 2018/0303991 A1 | 10/2018 | Nüsser et al. |
| 2018/0311421 A1 | 11/2018 | Tuseth |
| 2018/0311423 A1 | 11/2018 | Zeng et al. |
| 2018/0318483 A1 | 11/2018 | Dague et al. |
| 2018/0318547 A1 | 11/2018 | Yokoyama |
| 2018/0326131 A1 | 11/2018 | Muller et al. |
| 2018/0326132 A1 | 11/2018 | Maimon et al. |
| 2018/0333059 A1 | 11/2018 | Casas |
| 2018/0335037 A1 | 11/2018 | Shambaugh et al. |
| 2018/0344987 A1 | 12/2018 | Lancette et al. |
| 2018/0345028 A1 | 12/2018 | Aboud et al. |
| 2018/0361042 A1 | 12/2018 | Fitzgerald et al. |
| 2018/0369469 A1 | 12/2018 | Le Duc De Lillers et al. |
| 2019/0001034 A1 | 1/2019 | Taskin et al. |
| 2019/0001103 A1 | 1/2019 | Korkuch |
| 2019/0004037 A1 | 1/2019 | Zhang et al. |
| 2019/0015232 A1 | 1/2019 | Tuseth et al. |
| 2019/0015568 A1 | 1/2019 | Tuseth |
| 2019/0015570 A1 | 1/2019 | Muller |
| 2019/0030228 A1 | 1/2019 | Keenan et al. |
| 2019/0046702 A1 | 2/2019 | Siess et al. |
| 2019/0046703 A1 | 2/2019 | Shambaugh et al. |
| 2019/0054223 A1 | 2/2019 | Frazier et al. |
| 2019/0060539 A1 | 2/2019 | Siess et al. |
| 2019/0060543 A1 | 2/2019 | Khanal et al. |
| 2019/0069898 A1 | 3/2019 | Farnan |
| 2019/0076167 A1 | 3/2019 | Fantuzzi et al. |
| 2019/0083082 A1 | 3/2019 | Tassoni, Jr. et al. |
| 2019/0083690 A1 | 3/2019 | Siess et al. |
| 2019/0099532 A1 | 4/2019 | Er |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0125948 A1 | 5/2019 | Stanfield et al. |
| 2019/0143016 A1 | 5/2019 | Corbett et al. |
| 2019/0143018 A1 | 5/2019 | Salahieh et al. |
| 2019/0154053 A1 | 5/2019 | McBride et al. |
| 2019/0167122 A1 | 6/2019 | Obermiller et al. |
| 2019/0167305 A1 | 6/2019 | Pedersen et al. |
| 2019/0167875 A1 | 6/2019 | Simon et al. |
| 2019/0167878 A1 | 6/2019 | Rowe |
| 2019/0170153 A1 | 6/2019 | Scheckel |
| 2019/0175806 A1 | 6/2019 | Tuval et al. |
| 2019/0184078 A1 | 6/2019 | Zilbershlag et al. |
| 2019/0184080 A1 | 6/2019 | Mohl |
| 2019/0192752 A1 | 6/2019 | Tiller et al. |
| 2019/0199165 A1 | 6/2019 | Carson |
| 2019/0201603 A1 | 7/2019 | Siess et al. |
| 2019/0209755 A1 | 7/2019 | Nix et al. |
| 2019/0209758 A1 | 7/2019 | Tuval et al. |
| 2019/0211836 A1 | 7/2019 | Schumacher et al. |
| 2019/0211846 A1 | 7/2019 | Liebing |
| 2019/0211847 A1 | 7/2019 | Walsh et al. |
| 2019/0223877 A1 | 7/2019 | Nitzen et al. |
| 2019/0224390 A1 | 7/2019 | Barry |
| 2019/0231523 A1 | 8/2019 | Lombardi |
| 2019/0232025 A1 | 8/2019 | Tao et al. |
| 2019/0247627 A1 | 8/2019 | Korkuch et al. |
| 2019/0269840 A1 | 9/2019 | Tuval et al. |
| 2019/0275224 A1 | 9/2019 | Hanson et al. |
| 2019/0282741 A1 | 9/2019 | Franano et al. |
| 2019/0282744 A1 | 9/2019 | D'Ambrosio et al. |
| 2019/0282746 A1 | 9/2019 | Judisch |
| 2019/0290817 A1 | 9/2019 | Guo et al. |
| 2019/0298902 A1 | 10/2019 | Siess et al. |
| 2019/0298974 A1 | 10/2019 | Siess et al. |
| 2019/0316591 A1 | 10/2019 | Toellner |
| 2019/0321527 A1 | 10/2019 | King et al. |
| 2019/0321529 A1 | 10/2019 | Korakianitis et al. |
| 2019/0321531 A1 | 10/2019 | Cambronne et al. |
| 2019/0336664 A1 | 11/2019 | Liebing |
| 2019/0344000 A1 | 11/2019 | Kushwaha et al. |
| 2019/0344001 A1 | 11/2019 | Salahieh et al. |
| 2019/0344052 A1 | 11/2019 | Klepetko |
| 2019/0351117 A1 | 11/2019 | Cambronne et al. |
| 2019/0351119 A1 | 11/2019 | Cambronne et al. |
| 2019/0351120 A1 | 11/2019 | Kushwaha et al. |
| 2019/0358378 A1 | 11/2019 | Schumacher |
| 2019/0358379 A1 | 11/2019 | Wiessler et al. |
| 2019/0358384 A1 | 11/2019 | Epple |
| 2019/0365975 A1 | 12/2019 | Muller et al. |
| 2019/0381226 A1 | 12/2019 | Morozov et al. |
| 2019/0383298 A1 | 12/2019 | Toellner |
| 2020/0000988 A1 | 1/2020 | Epple |
| 2020/0000989 A1 | 1/2020 | Matheis et al. |
| 2020/0016309 A1 | 1/2020 | Kallenbach et al. |
| 2020/0022811 A1 | 1/2020 | Griswold |
| 2020/0023109 A1 | 1/2020 | Epple |
| 2020/0023110 A1 | 1/2020 | Jahangir |
| 2020/0023113 A1 | 1/2020 | Epple et al. |
| 2020/0030507 A1 | 1/2020 | Higgins et al. |
| 2020/0030509 A1 | 1/2020 | Siess et al. |
| 2020/0030510 A1 | 1/2020 | Higgins |
| 2020/0030511 A1 | 1/2020 | Higgins |
| 2020/0030512 A1 | 1/2020 | Higgins et al. |
| 2020/0038567 A1 | 2/2020 | Siess et al. |
| 2020/0038568 A1 | 2/2020 | Higgins et al. |
| 2020/0038571 A1 | 2/2020 | Jahangir |
| 2020/0054857 A1 | 2/2020 | Scheckel |
| 2020/0054861 A1 | 2/2020 | Korkuch et al. |
| 2020/0069857 A1 | 3/2020 | Schwammenthal et al. |
| 2020/0086021 A1 | 3/2020 | Jeevanandam et al. |
| 2020/0088207 A1 | 3/2020 | Schumacher et al. |
| 2020/0094019 A1 | 3/2020 | Siess et al. |
| 2020/0114053 A1 | 4/2020 | Salahieh et al. |
| 2020/0121905 A1 | 4/2020 | Zoll |
| 2020/0129684 A1 | 4/2020 | Pfeffer et al. |

(56) References Cited

U.S. PATENT DOCUMENTS

| | | | |
|---|---|---|---|
| 2020/0139028 A1* | 5/2020 | Scheckel | A61M 60/216 |
| 2020/0139029 A1 | 5/2020 | Scheckel et al. | |
| 2020/0147283 A1 | 5/2020 | Tanner et al. | |
| 2020/0155739 A1 | 5/2020 | Siess et al. | |
| 2020/0164125 A1 | 5/2020 | Muller et al. | |
| 2020/0164126 A1 | 5/2020 | Muller | |
| 2020/0179657 A1 | 6/2020 | Liu | |
| 2020/0261633 A1 | 8/2020 | Spanier | |
| 2020/0345337 A1 | 11/2020 | Muller et al. | |
| 2021/0052793 A1 | 2/2021 | Struthers et al. | |
| 2021/0093836 A1 | 4/2021 | Fantuzzi | |
| 2021/0146116 A1 | 5/2021 | Siess | |
| 2021/0205585 A1 | 7/2021 | Ullmann | |
| 2021/0268264 A1 | 9/2021 | Stotz | |
| 2021/0275791 A1 | 9/2021 | Korkuch et al. | |
| 2021/0290929 A1 | 9/2021 | Stotz | |
| 2021/0290930 A1 | 9/2021 | Kasel | |
| 2021/0290931 A1 | 9/2021 | Baumbach | |
| 2021/0290932 A1 | 9/2021 | Stotz | |
| 2021/0290937 A1 | 9/2021 | Baumbach | |
| 2021/0290939 A1 | 9/2021 | Baumbach | |
| 2021/0313869 A1 | 10/2021 | Strasswiemer et al. | |
| 2021/0316133 A1 | 10/2021 | Kassel et al. | |
| 2021/0322756 A1 | 10/2021 | Vollmer et al. | |
| 2021/0338999 A1 | 11/2021 | Stotz et al. | |
| 2021/0339004 A1 | 11/2021 | Schlebusch et al. | |
| 2021/0346678 A1 | 11/2021 | Baumbach et al. | |
| 2021/0379352 A1 | 12/2021 | Schlebusch et al. | |
| 2021/0379355 A1 | 12/2021 | Schuelke et al. | |
| 2022/0008053 A1 | 1/2022 | Fitzgerald et al. | |
| 2022/0008714 A1 | 1/2022 | Stotz | |
| 2022/0016411 A1 | 1/2022 | Winterwerber | |
| 2022/0072296 A1 | 3/2022 | Mori | |
| 2022/0072297 A1 | 3/2022 | Tuval et al. | |
| 2022/0080178 A1 | 3/2022 | Salahieh et al. | |
| 2022/0080180 A1 | 3/2022 | Siess et al. | |
| 2022/0080182 A1 | 3/2022 | Earles et al. | |
| 2022/0080183 A1 | 3/2022 | Earles et al. | |
| 2022/0080184 A1 | 3/2022 | Clifton et al. | |
| 2022/0080185 A1 | 3/2022 | Clifton et al. | |
| 2022/0096125 A1 | 3/2022 | Fantuzzi et al. | |
| 2022/0105337 A1 | 4/2022 | Salahieh et al. | |
| 2022/0105339 A1 | 4/2022 | Nix et al. | |
| 2022/0126083 A1 | 4/2022 | Grauwinkel et al. | |
| 2022/0161019 A1 | 5/2022 | Mitze et al. | |
| 2022/0161021 A1 | 5/2022 | Mitze et al. | |
| 2022/0241580 A1 | 8/2022 | Stotz et al. | |
| 2022/0249829 A1 | 8/2022 | Edwards et al. | |
| 2022/0323742 A1 | 10/2022 | Grauwinkel et al. | |
| 2022/0339400 A1 | 10/2022 | Fantuzzi et al. | |
| 2023/0001178 A1 | 1/2023 | Corbett et al. | |
| 2023/0063798 A1 | 3/2023 | Edwards et al. | |
| 2023/0079625 A1 | 3/2023 | Theran et al. | |
| 2023/0091199 A1 | 3/2023 | Siess et al. | |
| 2023/0105131 A1 | 4/2023 | Kerkhoffs et al. | |
| 2023/0125439 A1 | 4/2023 | Malone et al. | |
| 2023/0128328 A1 | 4/2023 | Malone et al. | |
| 2023/0130285 A1 | 4/2023 | Malone et al. | |
| 2023/0145482 A1 | 5/2023 | Garrigue | |
| 2023/0149691 A1 | 5/2023 | VanCamp et al. | |
| 2023/0149692 A1 | 5/2023 | Larsen et al. | |
| 2023/0158289 A1 | 5/2023 | Breidall et al. | |
| 2023/0233834 A1 | 7/2023 | Alexander et al. | |
| 2023/0277833 A1 | 9/2023 | Sharma et al. | |
| 2023/0277836 A1 | 9/2023 | Schellenberg et al. | |
| 2023/0293878 A1 | 9/2023 | Christof et al. | |
| 2023/0364411 A1 | 11/2023 | Bette | |
| 2023/0381492 A1 | 11/2023 | Alexander et al. | |
| 2023/0398330 A1 | 12/2023 | Mitze et al. | |
| 2023/0405286 A1 | 12/2023 | Schumacher et al. | |
| 2024/0074828 A1 | 3/2024 | Wenning | |
| 2024/0075277 A1 | 3/2024 | Schellenberg | |
| 2024/0102475 A1 | 3/2024 | Schuelke et al. | |
| 2024/0165392 A1 | 5/2024 | Liu et al. | |
| 2024/0198084 A1 | 6/2024 | Stotz | |
| 2024/0245902 A1 | 7/2024 | Schlebusch et al. | |
| 2024/0269451 A1 | 8/2024 | Siess et al. | |
| 2024/0269459 A1 | 8/2024 | Schellenberg et al. | |
| 2024/0277998 A1 | 8/2024 | Vogt et al. | |
| 2024/0285935 A1 | 8/2024 | Popov et al. | |
| 2024/0335651 A1 | 10/2024 | Mitze et al. | |
| 2024/0399135 A1 | 12/2024 | Stotz et al. | |
| 2025/0032773 A1 | 1/2025 | Baumbach et al. | |
| 2025/0082922 A1 | 3/2025 | Fabiunke et al. | |
| 2025/0121177 A1 | 4/2025 | West | |
| 2025/0134652 A1 | 5/2025 | Maiorano | |
| 2025/0144397 A1 | 5/2025 | Kassel et al. | |
| 2025/0161660 A1 | 5/2025 | Baumbach et al. | |
| 2025/0170388 A1 | 5/2025 | Kerkhoffs et al. | |
| 2025/0339669 A1 | 11/2025 | Stotz et al. | |

FOREIGN PATENT DOCUMENTS

| | | |
|---|---|---|
| AU | 2012261669 | 1/2013 |
| AU | 2013203301 | 5/2013 |
| AU | 2013273663 | 1/2014 |
| BR | PI0904483-3 | 7/2011 |
| CA | 2 026 692 | 4/1992 |
| CA | 2 026 693 | 4/1992 |
| CA | 2 292 432 | 5/1998 |
| CA | 2 664 835 | 2/2008 |
| CA | 2 796 357 | 10/2011 |
| CA | 3 000 581 | 4/2017 |
| CA | 2 947 984 | 11/2022 |
| CN | 1222862 A | 7/1999 |
| CN | 1254598 A | 5/2000 |
| CN | 1376523 A | 10/2002 |
| CN | 2535055 Y | 2/2003 |
| CN | 1118304 C | 8/2003 |
| CN | 2616217 | 5/2004 |
| CN | 1524000 | 8/2004 |
| CN | 1202871 C | 5/2005 |
| CN | 1833736 A | 9/2006 |
| CN | 200977306 | 11/2007 |
| CN | 101112628 | 1/2008 |
| CN | 101128168 | 2/2008 |
| CN | 201150675 | 11/2008 |
| CN | 101677812 | 3/2010 |
| CN | 201437016 | 4/2010 |
| CN | 201618200 | 11/2010 |
| CN | 201658687 | 12/2010 |
| CN | 201710717 | 1/2011 |
| CN | 201894758 | 7/2011 |
| CN | 102438552 | 5/2012 |
| CN | 102475923 | 5/2012 |
| CN | 102545538 | 7/2012 |
| CN | 202314596 | 7/2012 |
| CN | 102743801 | 10/2012 |
| CN | 103143072 | 6/2013 |
| CN | 103845766 | 6/2014 |
| CN | 103861162 | 6/2014 |
| CN | 103915980 | 7/2014 |
| CN | 203809157 | 9/2014 |
| CN | 203842087 | 9/2014 |
| CN | 104208763 | 12/2014 |
| CN | 104208764 | 12/2014 |
| CN | 203971004 | 12/2014 |
| CN | 104274873 | 1/2015 |
| CN | 204106671 | 1/2015 |
| CN | 204219479 | 3/2015 |
| CN | 103877630 | 2/2016 |
| CN | 205215814 | 5/2016 |
| CN | 103977464 | 8/2016 |
| CN | 104162192 | 9/2016 |
| CN | 104888293 | 3/2017 |
| CN | 106512117 | 3/2017 |
| CN | 104225696 | 6/2017 |
| CN | 107019824 | 8/2017 |
| CN | 107080871 | 8/2017 |
| CN | 206443963 | 8/2017 |
| CN | 107206139 | 9/2017 |
| CN | 107281567 | 10/2017 |
| CN | 104707194 | 11/2017 |
| CN | 107412892 | 12/2017 |

(56) References Cited

FOREIGN PATENT DOCUMENTS

| | | |
|---|---|---|
| CN | 107921187 | 4/2018 |
| CN | 105498002 | 6/2018 |
| CN | 106310410 | 7/2018 |
| CN | 207708250 | 8/2018 |
| CN | 106902404 | 8/2019 |
| CN | 110237327 | 9/2019 |
| CN | 209790495 | 12/2019 |
| CN | 110665079 | 1/2020 |
| CN | 210020563 | 2/2020 |
| CN | 111166948 | 5/2020 |
| CN | 111166949 | 5/2020 |
| CN | 112168427 | 1/2021 |
| CN | 113413544 | 9/2021 |
| CN | 215691046 | 2/2022 |
| CN | 215841206 | 2/2022 |
| CN | 114886614 | 8/2022 |
| CN | 217828630 | 11/2022 |
| CN | 115916111 | 4/2023 |
| CN | 218922664 | 4/2023 |
| CN | 116077106 | 5/2023 |
| CN | 116271502 | 6/2023 |
| CN | 116365757 | 6/2023 |
| CN | 219250364 | 6/2023 |
| CN | 116785582 | 9/2023 |
| CN | 116688321 | 10/2023 |
| CN | 116531654 | 11/2023 |
| CN | 116440404 | 3/2024 |
| CN | 117018427 | 3/2024 |
| CN | 117482377 | 4/2024 |
| CN | 117959584 | 5/2024 |
| CN | 118320293 | 7/2024 |
| CN | 118320294 | 7/2024 |
| CN | 113769260 | 9/2024 |
| CN | 118142074 | 9/2024 |
| CN | 118681125 | 9/2024 |
| CN | 118717356 | 10/2024 |
| CN | 118899971 | 11/2024 |
| CN | 119033506 | 11/2024 |
| DE | 1 001 642 | 1/1957 |
| DE | 11 65 144 | 3/1964 |
| DE | 27 07 951 | 9/1977 |
| DE | 26 24 058 | 12/1977 |
| DE | 3 545 214 | 7/1986 |
| DE | 41 05 278 | 8/1992 |
| DE | 195 46 336 | 5/1997 |
| DE | 695 01 834 | 10/1998 |
| DE | 198 54 724 | 5/1999 |
| DE | 198 21 307 | 10/1999 |
| DE | 199 10 872 | 10/1999 |
| DE | 199 56 380 | 11/1999 |
| DE | 100 59 714 | 5/2002 |
| DE | 103 45 694 | 4/2005 |
| DE | 697 31 709 | 4/2005 |
| DE | 101 55 011 | 11/2005 |
| DE | 601 19 592 | 9/2006 |
| DE | 11 2004 001 809 | 11/2006 |
| DE | 20 2005 020 288 | 6/2007 |
| DE | 10 2006 019 206 | 10/2007 |
| DE | 10 2006 036 948 | 2/2008 |
| DE | 10 2008 060 357 | 6/2010 |
| DE | 10 2009 011 726 | 9/2010 |
| DE | 10 2009 039 658 | 3/2011 |
| DE | 10 2009 047 845 | 3/2011 |
| DE | 20 2009 018 416 | 8/2011 |
| DE | 10 2010 041 995 | 4/2012 |
| DE | 11 2009 000 185 | 3/2013 |
| DE | 10 2012 022 456 | 5/2014 |
| DE | 10 2013 007 562 | 11/2014 |
| DE | 20 2013 007 408 | 12/2014 |
| DE | 10 2014 210 299 | 12/2015 |
| DE | 10 2014 212 323 | 12/2015 |
| DE | 11 2014 001 418 | 12/2015 |
| DE | 10 2014 224 151 | 6/2016 |
| DE | 10 2015 216 050 | 2/2017 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2016 122 268 | 5/2018 |
| DE | 10 2017 209 917 | 12/2018 |
| DE | 10 2017 212 193 | 1/2019 |
| DE | 10 2018 207 564 | 11/2019 |
| DE | 10 2018 207 578 | 11/2019 |
| DE | 10 2018 207 585 | 11/2019 |
| DE | 10 2018 207 591 | 11/2019 |
| DE | 10 2018 207 594 | 11/2019 |
| DE | 10 2018 207 611 | 11/2019 |
| DE | 10 2018 207 622 | 11/2019 |
| DE | 10 2018 208 536 | 12/2019 |
| DE | 10 2018 208 537 | 12/2019 |
| DE | 10 2018 208 540 | 12/2019 |
| DE | 10 2018 208 541 | 12/2019 |
| DE | 10 2018 208 550 | 12/2019 |
| DE | 10 2018 208 564 | 12/2019 |
| DE | 10 2018 208 945 | 12/2019 |
| DE | 10 2018 210 076 | 12/2019 |
| DE | 10 2018 207 624 | 1/2020 |
| DE | 10 2018 211 297 | 1/2020 |
| DE | 10 2018 211 327 | 1/2020 |
| DE | 10 2018 211 328 | 1/2020 |
| DE | 10 2018 212 153 | 1/2020 |
| DE | 10 2018 213 350 | 2/2020 |
| DE | 10 2018 220 658 | 6/2020 |
| DE | 10 2020 102 473 | 8/2021 |
| DE | 11 2020 003 063 | 3/2022 |
| DE | 11 2020 004 148 | 6/2022 |
| EP | 0 050 814 | 5/1982 |
| EP | 0 064 212 | 11/1982 |
| EP | 0 411 605 | 2/1991 |
| EP | 0 629 412 | 12/1994 |
| EP | 0 764 448 | 3/1997 |
| EP | 0 855 515 | 7/1998 |
| EP | 0 890 179 | 1/1999 |
| EP | 0 916 359 | 5/1999 |
| EP | 1 013 294 | 6/2000 |
| EP | 0 898 481 | 1/2002 |
| EP | 1 186 873 | 3/2002 |
| EP | 1 105 181 | 2/2004 |
| EP | 1 475 880 | 11/2004 |
| EP | 1 169 072 | 5/2005 |
| EP | 1 176 999 | 7/2005 |
| EP | 1 801 420 | 6/2007 |
| EP | 2 009 233 | 12/2008 |
| EP | 1 660 164 | 4/2009 |
| EP | 2 098 746 | 9/2009 |
| EP | 2 047 872 | 9/2010 |
| EP | 2 039 390 | 11/2010 |
| EP | 2 403 109 | 1/2012 |
| EP | 2 436 417 | 4/2012 |
| EP | 2 187 807 | 6/2012 |
| EP | 2 330 724 | 8/2012 |
| EP | 2 716 242 | 4/2014 |
| EP | 3 326 567 | 10/2014 |
| EP | 1 898 971 | 3/2015 |
| EP | 2 015 821 | 5/2015 |
| EP | 2 519 273 | 8/2015 |
| EP | 2 217 302 | 9/2015 |
| EP | 2 438 936 | 10/2015 |
| EP | 2 438 937 | 10/2015 |
| EP | 2 960 515 | 12/2015 |
| EP | 2 680 896 | 1/2016 |
| EP | 2 968 718 | 1/2016 |
| EP | 1 996 252 | 5/2016 |
| EP | 2 475 415 | 6/2016 |
| EP | 2 906 265 | 7/2016 |
| EP | 3 069 739 | 9/2016 |
| EP | 2 934 649 | 11/2016 |
| EP | 1 931 403 | 1/2017 |
| EP | 3 127 562 | 2/2017 |
| EP | 2 585 129 | 3/2017 |
| EP | 2 646 068 | 3/2017 |
| EP | 3 187 210 | 7/2017 |
| EP | 3 222 301 | 9/2017 |

(56) References Cited

FOREIGN PATENT DOCUMENTS

| | | |
|---|---|---|
| EP | 3 222 302 | 9/2017 |
| EP | 3 020 426 | 12/2017 |
| EP | 3 038 669 | 1/2018 |
| EP | 3 062 730 | 1/2018 |
| EP | 3 180 050 | 2/2018 |
| EP | 3 287 154 | 2/2018 |
| EP | 1 789 129 | 6/2018 |
| EP | 2 366 412 | 8/2018 |
| EP | 3 205 359 | 8/2018 |
| EP | 3 205 360 | 8/2018 |
| EP | 3 398 625 | 11/2018 |
| EP | 3 131 599 | 2/2019 |
| EP | 3 456 367 | 3/2019 |
| EP | 3 119 451 | 6/2019 |
| EP | 3 508 245 | 7/2019 |
| EP | 3 187 222 | 9/2019 |
| EP | 3 536 360 | 9/2019 |
| EP | 3 542 835 | 9/2019 |
| EP | 3 542 836 | 9/2019 |
| EP | 3 077 038 | 10/2019 |
| EP | 3 062 877 | 12/2019 |
| EP | 2 962 720 | 1/2020 |
| EP | 1 819 391 | 2/2020 |
| EP | 3 189 862 | 2/2020 |
| EP | 3 618 886 | 3/2020 |
| EP | 2 922 593 | 4/2020 |
| EP | 3 180 064 | 4/2020 |
| EP | 3 668 560 | 6/2020 |
| EP | 3 711 785 | 9/2020 |
| EP | 3 711 786 | 9/2020 |
| EP | 3 711 787 | 9/2020 |
| EP | 3 720 520 | 10/2020 |
| EP | 3 069 738 | 12/2020 |
| EP | 3 069 740 | 12/2020 |
| EP | 3 131 597 | 12/2020 |
| EP | 3 142 722 | 12/2020 |
| EP | 3 579 894 | 12/2020 |
| EP | 3 188 769 | 1/2021 |
| EP | 3 490 122 | 1/2021 |
| EP | 2 869 866 | 2/2021 |
| EP | 3 398 626 | 2/2021 |
| EP | 3 487 549 | 2/2021 |
| EP | 3 113 806 | 3/2021 |
| EP | 3 419 711 | 3/2021 |
| EP | 3 615 103 | 3/2021 |
| EP | 4 271 461 | 3/2021 |
| EP | 2 344 218 | 4/2021 |
| EP | 3 436 104 | 4/2021 |
| EP | 3 749 383 | 4/2021 |
| EP | 3 808 404 | 4/2021 |
| EP | 3 821 938 | 5/2021 |
| EP | 3 131 615 | 6/2021 |
| EP | 3 338 825 | 6/2021 |
| EP | 3 432 944 | 6/2021 |
| EP | 3 323 465 | 7/2021 |
| EP | 3 570 926 | 7/2021 |
| EP | 3 684 439 | 7/2021 |
| EP | 3 851 151 | 7/2021 |
| EP | 2 582 414 | 8/2021 |
| EP | 3 247 440 | 8/2021 |
| EP | 3 407 930 | 8/2021 |
| EP | 3 656 293 | 8/2021 |
| EP | 3 782 665 | 8/2021 |
| EP | 3 782 666 | 8/2021 |
| EP | 3 782 668 | 8/2021 |
| EP | 3 858 397 | 8/2021 |
| EP | 3 006 072 | 9/2021 |
| EP | 3 216 467 | 9/2021 |
| EP | 3 463 505 | 9/2021 |
| EP | 3 884 968 | 9/2021 |
| EP | 3 884 969 | 9/2021 |
| EP | 3 027 241 | 10/2021 |
| EP | 3 351 209 | 10/2021 |
| EP | 3 579 904 | 11/2021 |
| EP | 3 592 411 | 11/2021 |
| EP | 3 618 884 | 11/2021 |
| EP | 2 628 493 | 12/2021 |
| EP | 3 914 330 | 12/2021 |
| EP | 3 928 825 | 12/2021 |
| EP | 3 556 409 | 1/2022 |
| EP | 3 624 868 | 1/2022 |
| EP | 3 955 985 | 2/2022 |
| EP | 3 337 530 | 3/2022 |
| EP | 3 624 867 | 3/2022 |
| EP | 3 689 389 | 3/2022 |
| EP | 3 697 464 | 3/2022 |
| EP | 3 737 436 | 3/2022 |
| EP | 3 972 661 | 3/2022 |
| EP | 2 967 630 | 4/2022 |
| EP | 3 142 721 | 4/2022 |
| EP | 3 520 834 | 4/2022 |
| EP | 3 586 887 | 4/2022 |
| EP | 3 638 336 | 4/2022 |
| EP | 3 689 388 | 4/2022 |
| EP | 3 755 237 | 4/2022 |
| EP | 3 765 110 | 4/2022 |
| EP | 3 782 667 | 4/2022 |
| EP | 3 829 673 | 4/2022 |
| EP | 3 976 129 | 4/2022 |
| EP | 3 978 060 | 4/2022 |
| EP | 3 984 589 | 4/2022 |
| EP | 3 986 528 | 4/2022 |
| EP | 3 153 205 | 5/2022 |
| EP | 3 407 811 | 5/2022 |
| EP | 3 649 926 | 5/2022 |
| EP | 3 653 113 | 5/2022 |
| EP | 3 654 006 | 5/2022 |
| EP | 3 735 280 | 5/2022 |
| EP | 3 897 814 | 5/2022 |
| EP | 3 124 071 | 6/2022 |
| EP | 3 219 339 | 6/2022 |
| EP | 3 636 312 | 6/2022 |
| EP | 3 661 436 | 6/2022 |
| EP | 3 737 310 | 7/2022 |
| EP | 3 231 395 | 8/2022 |
| EP | 3 899 994 | 8/2022 |
| EP | 4 039 320 | 8/2022 |
| EP | 3 487 550 | 9/2022 |
| EP | 3 606 575 | 9/2022 |
| EP | 3 756 721 | 9/2022 |
| EP | 3 834 876 | 9/2022 |
| EP | 3 000 492 | 10/2022 |
| EP | 3 600 477 | 10/2022 |
| EP | 3 849 646 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 028 736 | 11/2022 |
| EP | 3 077 035 | 11/2022 |
| EP | 3 305 357 | 11/2022 |
| EP | 3 389 530 | 11/2022 |
| EP | 3 570 762 | 11/2022 |
| EP | 3 579 905 | 11/2022 |
| EP | 3 858 422 | 11/2022 |
| EP | 3 866 876 | 11/2022 |
| EP | 3 941 546 | 11/2022 |
| EP | 3 199 198 | 12/2022 |
| EP | 3 270 999 | 12/2022 |
| EP | 3 398 562 | 12/2022 |
| EP | 3 402 562 | 12/2022 |
| EP | 2 892 583 | 1/2023 |
| EP | 3 393 542 | 1/2023 |
| EP | 3 597 231 | 1/2023 |
| EP | 3 656 292 | 1/2023 |
| EP | 3 768 345 | 1/2023 |
| EP | 2 868 332 | 2/2023 |
| EP | 3 003 420 | 2/2023 |
| EP | 3 539 585 | 2/2023 |
| EP | 3 956 010 | 2/2023 |
| EP | 4 137 193 | 2/2023 |
| EP | 3 046 594 | 3/2023 |
| EP | 3 127 563 | 3/2023 |
| EP | 3 256 186 | 3/2023 |

(56) References Cited

FOREIGN PATENT DOCUMENTS

| | | |
|---|---|---|
| EP | 3 288 609 | 3/2023 |
| EP | 3 538 173 | 3/2023 |
| EP | 3 606 576 | 3/2023 |
| EP | 3 927 390 | 3/2023 |
| EP | 3 384 940 | 4/2023 |
| EP | 3 441 616 | 4/2023 |
| EP | 3 938 005 | 4/2023 |
| EP | 3 946 511 | 4/2023 |
| EP | 3 544 649 | 6/2023 |
| EP | 3 634 528 | 6/2023 |
| EP | 3 551 271 | 7/2023 |
| EP | 3 809 959 | 7/2023 |
| EP | 3 912 673 | 7/2023 |
| EP | 4 218 897 | 8/2023 |
| EP | 4 218 898 | 8/2023 |
| EP | 4 218 899 | 8/2023 |
| EP | 2 961 984 | 9/2023 |
| EP | 3 352 808 | 9/2023 |
| EP | 3 692 933 | 9/2023 |
| EP | 3 713 634 | 9/2023 |
| EP | 3 773 130 | 9/2023 |
| EP | 3 895 638 | 9/2023 |
| EP | 3 903 701 | 9/2023 |
| EP | 3 178 515 | 10/2023 |
| EP | 3 253 302 | 10/2023 |
| EP | 3 554 576 | 10/2023 |
| EP | 3 603 727 | 10/2023 |
| EP | 3 615 102 | 10/2023 |
| EP | 3 737 435 | 10/2023 |
| EP | 3 773 129 | 10/2023 |
| EP | 3 777 952 | 10/2023 |
| EP | 3 795 208 | 10/2023 |
| EP | 4 052 754 | 10/2023 |
| EP | 4 149 606 | 10/2023 |
| EP | 3 157 596 | 11/2023 |
| EP | 3 515 525 | 11/2023 |
| EP | 3 583 927 | 11/2023 |
| EP | 3 621 669 | 11/2023 |
| EP | 3 744 362 | 11/2023 |
| EP | 3 766 428 | 11/2023 |
| EP | 3 773 363 | 11/2023 |
| EP | 3 808 390 | 11/2023 |
| EP | 3 840 670 | 11/2023 |
| EP | 4 061 470 | 11/2023 |
| EP | 3 449 958 | 12/2023 |
| EP | 3 687 596 | 12/2023 |
| EP | 3 710 076 | 12/2023 |
| EP | 3 711 698 | 12/2023 |
| EP | 3 752 236 | 12/2023 |
| EP | 3 768 340 | 12/2023 |
| EP | 3 787 707 | 12/2023 |
| EP | 3 926 194 | 12/2023 |
| EP | 3 349 671 | 1/2024 |
| EP | 3 349 839 | 1/2024 |
| EP | 3 443 915 | 1/2024 |
| EP | 3 487 421 | 1/2024 |
| EP | 3 784 305 | 1/2024 |
| EP | 3 801 675 | 1/2024 |
| EP | 3 925 659 | 1/2024 |
| EP | 4 115 919 | 1/2024 |
| EP | 3 242 613 | 2/2024 |
| EP | 3 509 504 | 2/2024 |
| EP | 3 518 836 | 2/2024 |
| EP | 3 534 805 | 2/2024 |
| EP | 3 566 636 | 2/2024 |
| EP | 3 603 728 | 2/2024 |
| EP | 3 634 526 | 2/2024 |
| EP | 3 700 464 | 2/2024 |
| EP | 3 718 588 | 2/2024 |
| EP | 3 768 342 | 2/2024 |
| EP | 3 768 347 | 2/2024 |
| EP | 3 769 799 | 2/2024 |
| EP | 3 790 606 | 2/2024 |
| EP | 3 820 412 | 2/2024 |
| EP | 3 930 780 | 2/2024 |
| EP | 3 053 532 | 3/2024 |
| EP | 3 142 573 | 3/2024 |
| EP | 3 275 499 | 3/2024 |
| EP | 3 397 147 | 3/2024 |
| EP | 3 424 551 | 3/2024 |
| EP | 3 492 042 | 3/2024 |
| EP | 3 528 885 | 3/2024 |
| EP | 3 563 805 | 3/2024 |
| EP | 3 782 695 | 3/2024 |
| EP | 3 854 448 | 3/2024 |
| EP | 3 927 254 | 3/2024 |
| EP | 3 955 796 | 3/2024 |
| EP | 4 037 574 | 3/2024 |
| EP | 4 140 532 | 5/2024 |
| EP | 3 693 038 | 6/2024 |
| EP | 3 768 344 | 7/2024 |
| EP | 3 970 765 | 7/2024 |
| EP | 3 789 054 | 8/2024 |
| EP | 3 793 633 | 8/2024 |
| EP | 4 419 042 | 8/2024 |
| EP | 3 854 444 | 9/2024 |
| EP | 4 384 259 | 9/2024 |
| EP | 4 429 750 | 9/2024 |
| EP | 3 534 985 | 10/2024 |
| EP | 3 793 674 | 10/2024 |
| EP | 3 893 957 | 10/2024 |
| EP | 3 914 334 | 10/2024 |
| EP | 3 618 885 | 11/2024 |
| EP | 3 641 845 | 11/2024 |
| EP | 3 643 350 | 11/2024 |
| EP | 4 034 221 | 11/2024 |
| EP | 4 087 641 | 11/2024 |
| EP | 4 039 289 | 12/2024 |
| EP | 4 084 856 | 1/2025 |
| EP | 3 522 947 | 2/2025 |
| EP | 4 429 754 | 2/2025 |
| EP | 3 998 102 | 3/2025 |
| EP | 4 429 751 | 3/2025 |
| EP | 4 429 752 | 3/2025 |
| EP | 4 429 753 | 3/2025 |
| EP | 4 023 282 | 4/2025 |
| EP | 3 950 043 | 5/2025 |
| EP | 3 955 986 | 5/2025 |
| EP | 3 958 921 | 5/2025 |
| EP | 3 990 047 | 5/2025 |
| EP | 4 218 900 | 5/2025 |
| EP | 4 429 755 | 5/2025 |
| EP | 2 830 675 | 6/2025 |
| EP | 3 463 539 | 6/2025 |
| EP | 3 965 845 | 6/2025 |
| EP | 4 039 319 | 6/2025 |
| EP | 3 668 558 | 7/2025 |
| EP | 3 780 041 | 7/2025 |
| EP | 4 095 872 | 7/2025 |
| EP | 4 100 091 | 7/2025 |
| EP | 3 668 559 | 8/2025 |
| EP | 3 746 149 | 8/2025 |
| EP | 3 823 687 | 8/2025 |
| EP | 3 848 088 | 8/2025 |
| EP | 3 908 177 | 8/2025 |
| EP | 4 119 184 | 9/2025 |
| EP | 4 218 556 | 9/2025 |
| EP | 3 706 853 | 10/2025 |
| EP | 4 046 678 | 10/2025 |
| FR | 1458525 | 3/1966 |
| FR | 2 768 056 | 3/1999 |
| GB | 0 648 739 | 1/1951 |
| GB | 2 213 541 | 8/1989 |
| GB | 2 345 387 | 7/2000 |
| GB | 2 451 161 | 12/2011 |
| GB | 2 545 062 | 6/2017 |
| GB | 2 545 750 | 6/2017 |
| JP | S59-076463 | 5/1984 |
| JP | 59-119788 | 8/1984 |
| JP | S61-500059 | 1/1986 |
| JP | S62-113555 | 7/1987 |
| JP | S64-68236 | 3/1989 |
| JP | H02-055886 | 2/1990 |
| JP | H02-079738 | 3/1990 |

(56) References Cited

FOREIGN PATENT DOCUMENTS

| | | |
|---|---|---|
| JP | H04-176471 | 6/1992 |
| JP | H04-108384 | 9/1992 |
| JP | H08-057042 | 3/1996 |
| JP | H08-504621 | 5/1996 |
| JP | H09-028664 | 2/1997 |
| JP | H10-052489 | 2/1998 |
| JP | 2888609 | 5/1999 |
| JP | 2889384 | 5/1999 |
| JP | H11-239617 | 9/1999 |
| JP | 2001-037728 | 2/2001 |
| JP | 2001-515374 | 9/2001 |
| JP | 2001-515375 | 9/2001 |
| JP | 2003-019197 | 1/2003 |
| JP | 2003-525438 | 8/2003 |
| JP | 2003-528697 | 9/2003 |
| JP | 2004-019468 | 1/2004 |
| JP | 2004-515278 | 5/2004 |
| JP | 2004-278375 | 10/2004 |
| JP | 2005-028137 | 2/2005 |
| JP | 2005-507039 | 3/2005 |
| JP | 2007-222644 | 9/2007 |
| JP | 2008-511414 | 4/2008 |
| JP | 2008-516654 | 5/2008 |
| JP | 2010-503495 | 2/2010 |
| JP | 2010-518907 | 6/2010 |
| JP | 2010-258181 | 11/2010 |
| JP | 2010-534080 | 11/2010 |
| JP | 2013-013216 | 1/2013 |
| JP | 2013-519497 | 5/2013 |
| JP | 2014-004303 | 1/2014 |
| JP | 2014-524274 | 9/2014 |
| JP | 2015-514529 | 5/2015 |
| JP | 2015-514531 | 5/2015 |
| JP | 2015-122448 | 7/2015 |
| JP | 2016-002466 | 1/2016 |
| JP | 2016-532500 | 10/2016 |
| JP | 6063151 | 1/2017 |
| JP | 6267625 | 1/2018 |
| JP | 2018-057878 | 4/2018 |
| JP | 2019-508128 | 3/2019 |
| JP | 2019-516458 | 6/2019 |
| JP | 6572056 | 9/2019 |
| JP | 2020-072985 | 5/2020 |
| JP | 2020-523090 | 8/2020 |
| JP | 2018-510708 | 3/2021 |
| JP | 2019-509141 | 2/2022 |
| KR | 10-2011-0098192 | 9/2011 |
| RO | 131676 | 2/2017 |
| RU | 2 051 695 | 1/1996 |
| TW | 374317 | 11/1999 |
| UA | 97202 C2 | 1/2012 |
| WO | WO 94/009835 | 5/1994 |
| WO | WO 97/037696 | 10/1997 |
| WO | WO 97/037697 | 10/1997 |
| WO | WO 97/039785 | 10/1997 |
| WO | WO 99/049912 | 10/1999 |
| WO | WO 00/033446 | 6/2000 |
| WO | WO 02/022200 | 3/2002 |
| WO | WO 02/041935 | 5/2002 |
| WO | WO 02/070039 | 9/2002 |
| WO | WO 03/075981 | 9/2003 |
| WO | WO 03/103745 | 12/2003 |
| WO | WO 2005/007024 | 1/2005 |
| WO | WO 2005/020848 | 3/2005 |
| WO | WO 2005/028014 | 3/2005 |
| WO | WO 2005/037345 | 4/2005 |
| WO | WO 2007/006055 | 1/2007 |
| WO | WO 2007/033933 | 3/2007 |
| WO | WO 2007/044510 | 4/2007 |
| WO | WO 2007/105842 | 9/2007 |
| WO | WO 2008/017289 | 2/2008 |
| WO | WO 2008/081783 | 7/2008 |
| WO | WO 2008/106103 | 9/2008 |
| WO | WO 2009/010888 | 1/2009 |
| WO | WO 2009/046789 | 4/2009 |
| WO | WO 2009/046790 | 4/2009 |
| WO | WO 2009/073037 | 6/2009 |
| WO | WO 2009/114456 | 9/2009 |
| WO | WO 2010/014418 | 2/2010 |
| WO | WO 2010/092347 | 8/2010 |
| WO | WO 2010/119267 | 10/2010 |
| WO | WO 2011/003043 | 1/2011 |
| WO | WO 2011/081626 | 7/2011 |
| WO | WO 2011/096975 | 8/2011 |
| WO | WO 2011/160858 | 12/2011 |
| WO | WO 2012/018917 | 2/2012 |
| WO | WO 2012/047540 | 4/2012 |
| WO | WO 2012/112129 | 8/2012 |
| WO | WO 2013/013248 | 1/2013 |
| WO | WO 2013/037380 | 3/2013 |
| WO | WO 2013/092971 | 6/2013 |
| WO | WO 2013/093058 | 6/2013 |
| WO | WO 2013/120957 | 8/2013 |
| WO | WO 2013/167432 | 11/2013 |
| WO | WO 2013/173239 | 11/2013 |
| WO | WO 2014/042925 | 3/2014 |
| WO | WO 2014/096408 | 6/2014 |
| WO | WO 2015/019132 | 2/2015 |
| WO | WO 2015/039605 | 3/2015 |
| WO | WO 2015/063281 | 5/2015 |
| WO | WO 2015/085076 | 6/2015 |
| WO | WO 2015/109028 | 7/2015 |
| WO | WO 2015/134944 | 9/2015 |
| WO | WO 2015/172173 | 11/2015 |
| WO | WO 2015/175718 | 11/2015 |
| WO | WO 2016/028644 | 2/2016 |
| WO | WO 2016/055368 | 4/2016 |
| WO | WO 2016/137743 | 9/2016 |
| WO | WO 2016/146661 | 9/2016 |
| WO | WO 2016/146663 | 9/2016 |
| WO | WO 2017/004175 | 1/2017 |
| WO | WO 2017/015764 | 2/2017 |
| WO | WO 2017/021465 | 2/2017 |
| WO | WO 2017/053361 | 3/2017 |
| WO | WO 2017/053988 | 3/2017 |
| WO | WO 2017/060257 | 4/2017 |
| WO | WO 2017/112695 | 6/2017 |
| WO | WO 2017/112698 | 6/2017 |
| WO | WO 2017/118738 | 7/2017 |
| WO | WO 2017/147103 | 8/2017 |
| WO | WO 2017/147291 | 8/2017 |
| WO | WO 2017/157884 | 9/2017 |
| WO | WO 2017/159849 | 9/2017 |
| WO | WO 2017/162619 | 9/2017 |
| WO | WO 2017/194562 | 11/2017 |
| WO | WO 2017/205909 | 12/2017 |
| WO | WO 2018/007120 | 1/2018 |
| WO | WO 2018/036927 | 3/2018 |
| WO | WO 2018/039479 | 3/2018 |
| WO | WO 2018/088939 | 3/2018 |
| WO | WO 2018/078615 | 5/2018 |
| WO | WO 2018/081040 | 5/2018 |
| WO | WO 2018/089970 | 5/2018 |
| WO | WO 2018/109038 | 6/2018 |
| WO | WO 2018/139508 | 8/2018 |
| WO | WO 2018/165519 | 9/2018 |
| WO | WO 2018/197306 | 11/2018 |
| WO | WO 2018/202779 | 11/2018 |
| WO | WO 2018/234454 | 12/2018 |
| WO | WO 2019/034670 | 2/2019 |
| WO | WO 2019/035804 | 2/2019 |
| WO | WO 2019/038343 | 2/2019 |
| WO | WO 2019/038345 | 2/2019 |
| WO | WO 2019/055591 | 3/2019 |
| WO | WO 2019/057636 | 3/2019 |
| WO | WO 2019/067233 | 4/2019 |
| WO | WO 2019/078723 | 4/2019 |
| WO | WO 2019/118371 | 6/2019 |
| WO | WO 2019/135767 | 7/2019 |
| WO | WO 2019/137911 | 7/2019 |
| WO | WO 2019/138350 | 7/2019 |
| WO | WO 2019/145253 | 8/2019 |
| WO | WO 2019/158996 | 8/2019 |
| WO | WO 2019/161245 | 8/2019 |

(56) References Cited

FOREIGN PATENT DOCUMENTS

| | | |
|---|---|---|
| WO | WO 2019/180104 | 9/2019 |
| WO | WO 2019/180179 | 9/2019 |
| WO | WO 2019/180181 | 9/2019 |
| WO | WO 2019/191245 | 10/2019 |
| WO | WO 2019/193604 | 10/2019 |
| WO | WO 2018/135477 | 11/2019 |
| WO | WO 2018/135478 | 11/2019 |
| WO | WO 2019/211410 | 11/2019 |
| WO | WO 2019/219868 | 11/2019 |
| WO | WO 2019/219871 | 11/2019 |
| WO | WO 2019/219872 | 11/2019 |
| WO | WO 2019/219874 | 11/2019 |
| WO | WO 2019/219876 | 11/2019 |
| WO | WO 2019/219881 | 11/2019 |
| WO | WO 2019/219882 | 11/2019 |
| WO | WO 2019/219883 | 11/2019 |
| WO | WO 2019/219884 | 11/2019 |
| WO | WO 2019/219885 | 11/2019 |
| WO | WO 2019/229206 | 12/2019 |
| WO | WO 2019/229207 | 12/2019 |
| WO | WO 2019/229210 | 12/2019 |
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/229224 | 12/2019 |
| WO | WO 2019/234146 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030700 | 2/2020 |
| WO | WO 2020/064911 | 4/2020 |
| WO | WO 2020/073047 | 4/2020 |
| WO | WO 2020/123333 | 6/2020 |
| WO | WO 2020/132211 | 6/2020 |
| WO | WO 2020/137708 | 7/2020 |
| WO | WO 2020/176236 | 9/2020 |
| WO | WO 2020/187797 | 9/2020 |
| WO | WO 2020/219430 | 10/2020 |
| WO | WO 2020/234785 | 11/2020 |
| WO | WO 2020/242881 | 12/2020 |
| WO | WO 2020/264174 | 12/2020 |
| WO | WO 2021/046275 | 3/2021 |
| WO | WO 2021/062265 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2021/191106 | 9/2021 |
| WO | WO 2023/040546 | 12/2021 |
| WO | WO 2022/011095 | 1/2022 |
| WO | WO 2022/032286 | 2/2022 |
| WO | WO 2022/056542 | 3/2022 |
| WO | WO 2022/063650 | 3/2022 |
| WO | WO 2022/072944 | 4/2022 |
| WO | WO 2022/076862 | 4/2022 |
| WO | WO 2022/076948 | 4/2022 |
| WO | WO 2022/091784 | 5/2022 |
| WO | WO 2022/109589 | 5/2022 |
| WO | WO 2022/109590 | 5/2022 |
| WO | WO 2022/109591 | 5/2022 |
| WO | WO 2022/173970 | 8/2022 |
| WO | WO 2022/173977 | 8/2022 |
| WO | WO 2022/174249 | 8/2022 |
| WO | WO 2023/226779 | 9/2022 |
| WO | WO 2023/003937 | 1/2023 |
| WO | WO 2023/278599 | 1/2023 |
| WO | WO 2023/014742 | 2/2023 |
| WO | WO 2023/049813 | 3/2023 |
| WO | WO 2024/160098 | 4/2023 |
| WO | WO 2023/076461 | 5/2023 |
| WO | WO 2023/076869 | 5/2023 |
| WO | WO 2024/125157 | 5/2023 |
| WO | WO 2023/112044 | 6/2023 |
| WO | WO 2023/230157 | 11/2023 |
| WO | WO 2024/104184 | 5/2024 |
| WO | WO 2024/243154 | 11/2024 |
| WO | WO 2025/075927 | 4/2025 |
| WO | WO 2025/226734 | 10/2025 |

OTHER PUBLICATIONS

International Search Report and Written Opinion received in PCT Application No. PCT/US2021/072497, dated Mar. 7, 2022 in 12 pages.

"ABMD—Taking a Closer Look at Impella ECP as the Pivotal Trial Gets Underway", Guggenheim, Press Release, Mar. 29, 2022, pp. 4.

"Edwards Sapien 3 Kit—Transapical and Transaortic", Edwards Lifesciences, Released Nov. 8, 2016, pp. 11. chrome-extension://efaidnbmnnnibpcajpcglclefindmkaj/https://edwardsprod.blob.core.windows.net/media/De/sapien3/doc-0045537b%20-%20certitude.pdf.

Escudeiro et al., "Tribological behavior of uncoated and DLC-coated CoCr and Ti-alloys in contact with UHMWPE and PEEK counterbodies;" Tribology International, vol. 89, 2015, pp. 97-104.

Gopinath, Divya, "A System for Impedeance Characterization of Coronary Stents", University of Strathclyde Engineering, Thesis, Aug. 2015, pp. 77.

Hinkel et al., "Pump Reliability and Efficiency Increase Maintenance Program—Utilizing High Performance Thermoplastics;" Proceedings of the 16th International Pump Users Symposium, Texas A&M University. Turbomachinery Laboratories; 1999, pp. 115-120.

Neale, Michael J., "The Tribology Handbook;" 1999, Butterworth-Heinemann, Second Edition, pp. 582.

Park et al., "A Novel Electrical Potential Sensing Method for in Vitro Stent Fracture Monitoring and Detection", Jan. 1, 2011, vol. 21, No. 4, pp. 213-222.

Sak et al., "Influence of polyetheretherketone coatings on the Ti—13Nb—13Zr titanium alloy's bio-tribological properties and corrosion resistance;" Materials Science and Engineering: C, vol. 63, 2016, pp. 52-61.

"Transvalvular Insertion Tool (TVI)", Pressure Products, Feb. 2013, https://www.pressure-products.com/wip/tvi.html, as printed Jul. 25, 2024 in 2 pages.

Vollkron et al., "Advanced Suction Detection for an Axial Flow Pump", Artificial Organs, 2006, vol. 30, No. 9, pp. 665-670.

Vollkron et al., "Development of a Suction Detection System for Axial Blood Pumps", Artificial Organs, 2004, vol. 28, No. 8, pp. 709-716.

International Search Report and Written Opinion received in PCT Application No. PCT/US2024/030259, dated Sep. 4, 2024 in 15 pages.

International Search Report and Written Opinion received in PCT Application No. PCT/US2021/072499, dated Jul. 1, 2022 in 8 pages.

Ai, X. (2013). Radial Bearings. In: Wang, Q.J., Chung, YW. (eds) Encyclopedia of Tribology. Springer, Boston, MA https://doi.org/10.1007/978-0-387-92897-5_334, accessed Oct. 18, 2024, pp. 4.

GGB by Timken Bearings FAQ; "What is a Slide Bearing?;" https://www.ggbearings.com/en/why-choose-ggb/faq/bearings-faq/what-slide-bearing; accessed Oct. 10, 2024, pp. 1.

Google.com, "Spider Bearing—Search Results;" https://www.google.com/search?q=spider+bearing&rlz=X1C1GCEA_enUS1059US1059&oq=spider+beari&gs_lcrp=EgZjaHJvbWUqCQgAEEUYOxiABDIJCAAQRRg7GIAEMgYIARBFGDkyBwgCEAAYgAQyBwgDEAAYgAQyBwgEEAAYgAQyBwgFEAAYgAQyBwgGEAAYgAQyBggHEEUYPKgCALACAA&sourceid=chrome&ie=UTF-8, accessed Oct. 18, 2024, pp. 4.

(56)         References Cited

OTHER PUBLICATIONS

McMaster-Carr Online Catalog, "Bearings search results;" https://www.mcmaster.com/products/bearings/; accessed Oct. 18, 2024, pp. 5.

McMaster-Carr Online Catalog, "Slide Bearings search results;" https://www.mcmaster.com/products/slide-bearings/; accessed Oct. 18, 2024, pp. 21.

RBCbearings.com, "RBC Bearings Incorporated—Products;" https://www.rbcbearings.com/Products; accessed Oct. 18, 2024, pp. 2.

SKF.com; "Products: Bearings;" https://www.skf.com/us/products/bearings; accessed Oct. 18, 2024, pp. 8.

Wikipedia, "Plain Bearing," https://en.wikipedia.org/wiki/Plain_bearing; accessed Oct. 18, 2024, pp. 10.

Bergersen et al., "Congenital Heart Disease: The Catheterization Manual", Netherlands, Springer, 2009, pp. 115-118 and 143-150.

Delgado et al., "Interventional Treatment of Advanced Ischemic Heart Disease", Percutaneous Mechanical Assist Devices, Ch. 6, Springer, 2009, pp. 85-91.

Delgado et al., "Interventional Treatment of Advanced Ischemic Heart Disease", The Future of Treatment of Advanced Ischemic Heart Disease, Ch. 8, Springer, 2009, pp. 129-142.

Eeckhout, MD, PhD, et al., "Handbook of Complications During Percutaneous Cardiovascular Interventions", 2007 Informa UK Ltd., Ch. 12, pp. 167-177.

"FDA Approves Abiomed's Heart Pump Impella, Shares Rise", Reuters 2008 press release, Jun. 2, 2008, |https://jp.reuters.com/article/us-abiomed/fda-approves-abiomeds-heart-pump-impella-shares-rise-idUSBNG131420080602/, 1 page.

Lake et al., "Pediatric Cardiac Anesthesia", 4th Edition, 2005, Ch. 15, pp. 291-303.

Machiraju, Venkat R., "Redo Cardiac Surgery in Adults", Practical Approaches to the Current "On-Pump" Redo Coronary Artery Bypass Surgery, Ch. 2, Springer, 2012, pp. 7-19.

Machiraju, Venkat R., "Redo Cardiac Surgery in Adults", Options for Advanced Mechanical Support for Cardiogenic Shock Complicating Cardiac Reoperations, Ch. 9, Springer, 2012, pp. 67-80.

Machiraju, Venkat R., "Redo Cardiac Surgery in Adults", Percutaneous Approaches to Valvular Heart Disease After Previous Cardiac Surgery, Ch. 21, Springer, 2012, pp. 195-200.

New Hampshire Ball Bearings, Inc., "Engineering Reference, Rod End & Spherical Bearings", https://www.nhbb.com/index.php/knowledge-center/engineering-reference/rod-end-spherical-bearings/self-lubricating-liner-systems, 2021, p. 13.

Parrillo et al., "Critical Care Medicine", Principles of Diagnosis and Management in the Adult, Elsevier, 4th Edition, 2014, Chapters 4 & 29, pp. 47-58.e1 and 442-469.e4.

Vincent, MD, PhD, et al., "Textbook of Critical Care", Acute Coronary Syndromes: Therapy, Elsevier, 7th Edition, Ch. 78, 2017, pp. 520-531.e3.

Vincent, MD, PhD, et al., "Textbook of Critical Care", Mechanical Support in Cardiogenic Shock, Elsevier, 7th Edition, Ch. 91, 2017, pp. 637-648.e3.

* cited by examiner

DISTAL

PROXIMAL

1000

1002

DEVICE RUNNING
Change the flow rate via the rotary

MIN FLOW
1.6 l/min

MAX FLOW
2.2 l/min

TRUE FLOW
2.1

OK

RUNTIME
00:01:20

SET FLOW
2.0 l/min

160

80

0

XXXX

ABP
120/80 mmHg

LVP
140/15 mmHg

LVEDP
13 mmHg

KARDION

SETTINGS | OVERVIEW | 🔒 LOCK SCREEN

100%

XXXX 1010  1008

1006

1004

1000

1104

1102

1108

1106

1000

DEVICE RUNNING
Change the flow rate via the rotary

MIN FLOW
1.6 l/min

MAX FLOW
2.2 l/min

TRUE FLOW
2.1

RUNTIME
00:01:20

SET FLOW
2.0 l/min

160

80

0 xxxx

SETTINGS
OVERVIEW
LOCK SCREEN

ABP
120/80    mmHg
LVP
140/15    mmHg
LVEDP
13    mmHg

100%
xxxx

OK

KARDION

1302

RFID

1304

1107

1306

$$P_{Differential} = P_{AO} - P_{LV}$$

188

187

145

186

150

105C

160a

135

140

130

185

MECHANICAL CIRCULATORY SUPPORT SYSTEM WITH GUIDEWIRE AID

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. For example, this application claims priority to U.S. Provisional Application No. 63/116, 616, titled MECHANICAL LEFT VENTRICULAR SUPPORT SYSTEM FOR CARDIOGENIC SHOCK and filed on Nov. 20, 2020, to U.S. Provisional Application No. 63/116,686, titled MECHANICAL CIRCULATORY SUPPORT SYSTEM FOR HIGH RISK CORONARY INTERVENTIONS and filed on Nov. 20, 2020, to U.S. Provisional Application No. 63/224,326, titled GUIDEWIRE and filed Jul. 21, 2021, and to U.S. Provisional Application No. 63/229,436, titled SEAL FOR A MECHANICAL CIRCULATORY SUPPORT DEVICE and filed Aug. 4, 2021, the entire content of each of which is incorporated by reference herein in its entirety for all purposes and forms a part of this specification.

BACKGROUND

Mechanical circulatory support systems may be used to assist with pumping blood during various medical procedures. For example, percutaneous coronary intervention (PCI) is a non-surgical procedure to revascularize stenotic coronary arteries. PCI includes a variety of techniques, e.g. balloon angioplasty, stent implantation, rotablation and lithotripsy. A PCI is considered high risk if either the patient has relevant comorbidities (e.g. frailty or advanced age), the PCI per se is very complex (e.g. bifurcation or total occlusions) or hemodynamic status is challenging (e.g. impaired ventricular function). There remains a need for a mechanical circulatory support system, which may be temporary and specifically configured to lower the risk of high-risk PCI, and with features that reduce complexity of using the system.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods for mechanical circulatory support systems.

The following disclosure describes non-limiting examples of some embodiments. For instance, other embodiments of the disclosed systems and methods may or may not include the features described herein. Moreover, disclosed advantages and benefits can apply only to certain embodiments and should not be used to limit the disclosure.

A minimally invasive, miniaturized, percutaneous mechanical circulatory support (MCS) system is provided. A guidewire aid may be temporarily used prior to insertion of the pump device into a patient, and which aids in threading a guidewire through the pump device. The guidewire aid may include a guide tube extending through the pump device along a path that avoids a space occupied by a rotating impeller in use, which may be external to a device housing. A funnel at a distal end may aid with entry of the guidewire into the guide tube. A side tab may facilitate grasping the aid. The aid, for example the guide tube, funnel, and/or tab, may tear off for lateral removal of the guidewire aid from the guidewire, which may be after the guidewire has been inserted into the body. The pump device may be placed across the aortic valve via a single femoral arterial access point. The pump may be a low profile axial rotary blood pump carried by the distal end of a catheter, such as an eight French (Fr) catheter. The system may be percutaneously inserted through the femoral artery and positioned across the aortic valve into the left ventricle. The device actively unloads the left ventricle by pumping blood from the left ventricle into the ascending aorta and systemic circulation.

In one aspect, a mechanical circulatory support system, which may be used for high risk coronary interventions, is described. The system may include an elongate flexible catheter shaft, having a proximal end and a distal end, and a circulatory support device carried by the distal end of the shaft. The circulatory support device may include a tubular housing having a proximal end and a distal end, an impeller within the housing, and a removable guidewire guide tube. The removable guidewire guide tube may be entering a first guidewire port on the distal end of the housing, exiting the housing via a second guidewire port on a side wall of the housing distal to the impeller, entering a third guidewire port on a proximal side of the impeller, and extending proximally into the catheter shaft.

In another aspect, a method of inserting a guidewire through a mechanical circulatory support system is described. The method comprises inserting the guidewire into a distal end of a removable guide tube, where the guide tube enters a first guidewire port on a distal end of a tubular housing of the system, exits the tubular housing via a second guidewire port on a side wall of the tubular housing distal to an impeller of the system, enters a third guidewire port on a proximal side of the impeller, and extends proximally into a catheter shaft.

Various other example aspects and embodiments are shown and described throughout this disclosure. For example, various particular example embodiments are further described herein in the Detailed Description in the section "Example Embodiments."

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawings, can be arranged, substituted, combined, and designed in a wide variety of different configurations, all of which are explicitly contemplated and make part of this disclosure.

DETAILED DESCRIPTION

Figure 1:
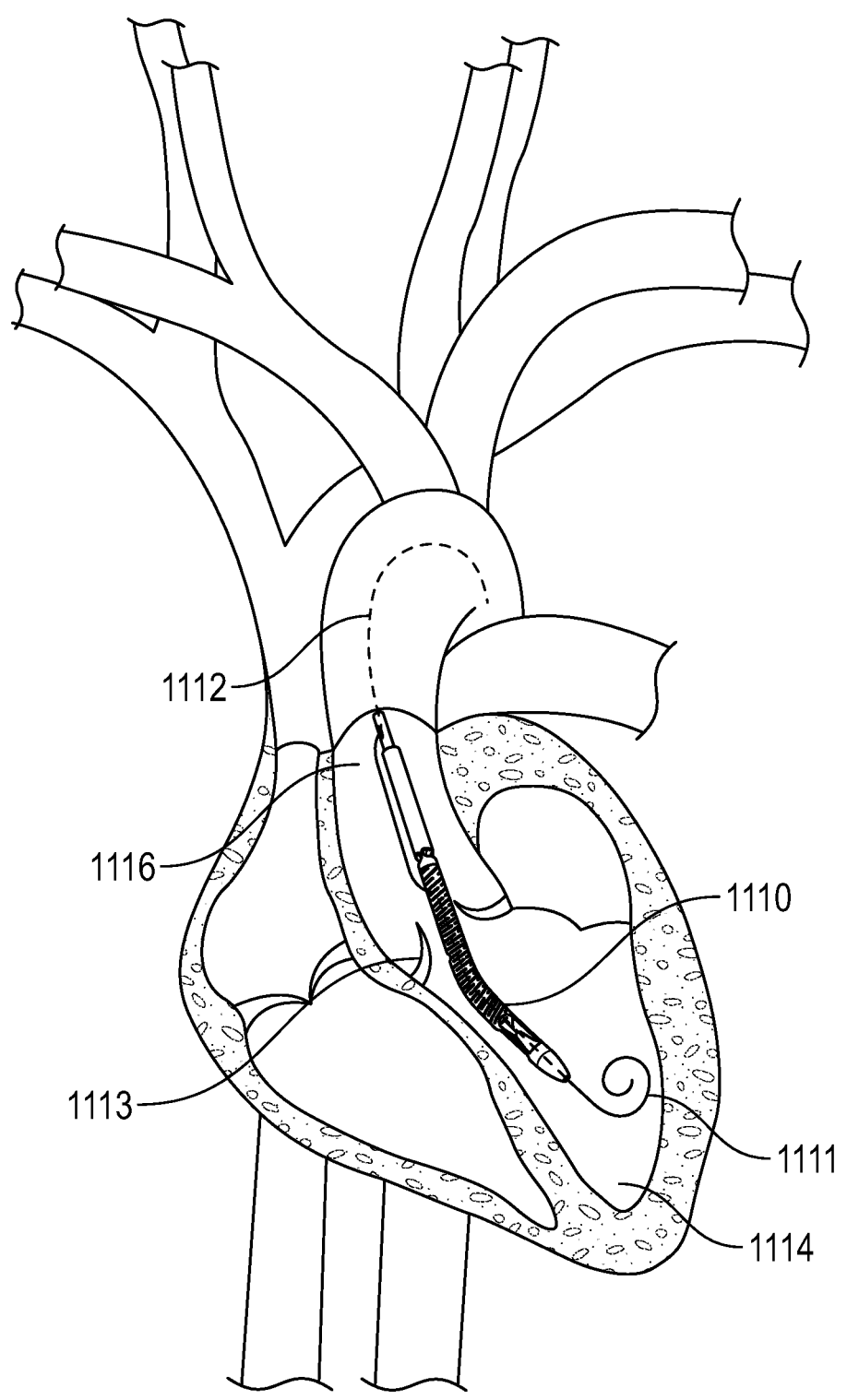
FIG. 1 is a cross sectional rendering of an embodiment of a mechanical circulatory support (MCS) device of the present disclosure carried by a catheter and positioned across an aortic valve via a femoral artery access.

The following detailed description is directed to certain specific embodiments of a mechanical circulatory support (MCS) system and method, and related features. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments. Reference will now be made in detail to embodiments of the invention, examples of which are illustrated in the accompanying drawings. Wherever possible, the same reference numbers will be used throughout the drawings to refer to the same or like parts.

The MCS system according to the present disclosure includes a temporary (e.g., generally no more than about 6 hours, or in some embodiments no more than about 3 hours, no more than about 4 hours, no more than about 7 hours, no more than about 8 hours, no more than about 9 hours, or no more than about 10 hours) left ventricular support device. The device may be used during high-risk percutaneous coronary intervention (PCI) performed in elective or urgent, hemodynamically stable patients with severe coronary artery disease and/or depressed left ventricular ejection fraction, e.g. when a heart team, including a cardiac surgeon, has determined high risk PCI is the appropriate therapeutic option. It is placed across the aortic valve via a single femoral arterial access.

The system includes a low-profile axial rotary blood pump mounted on a catheter such as an 8 Fr catheter, referred to as an MCS pump or MCS device. A guidewire guide tube and/or funnel aid may be used to assist with inserting a guidewire through the pump region of the system. The guide tube may extend through openings in a tubular housing portion, such as the inlet tube and/or pump region of the device, such that the guidewire extends partially through the tubular housing, exits the tubular housing to avoid the impeller and extends outside the tubular housing, and re-enters the tubular housing or other component of the system. When in place, the MCS pump can be driven by an MCS controller to provide up to about 4.0 liters/minute of partial left ventricular support, at about 60 mm Hg. No system purging is needed due to improved bearing design and sealed motor, and the system is visualized fluoroscopically eliminating the need for placement using sensors.

The system may further include a sheath, which may be expandable, which allows 8-10 Fr initial access size for easy insertion and closing, expandable to allow introduction of 14 Fr and 18 Fr pump devices and return to a narrower diameter around the 8 Fr catheter once the pump has passed. This feature may allow passage of the heart pump through vasculature while minimizing shear force within the blood vessel, advantageously reducing risk of bleeding and healing complications. Distention or stretching of an arteriotomy may be done with radial stretching with minimal shear, which is less harmful to the vessel. Access may be accomplished via transfemoral, transaxillary, transaortal, or transapical approach.

FIG. 1 shows a rendering of an embodiment of an MCS device 1110 mounted on the tip of a catheter 1112, which may be a 8 Fr catheter, and a guidewire 1111 extending outwardly from a distal end of the device 1110. An inlet tube portion of the device 1110 extends across the aortic valve 1113. As further described herein, an impeller is located at the outflow section of the inlet tube drawing blood from the left ventricle 1114 and ejecting it into the ascending aorta 1116. A motor is mounted directly proximal to the impeller in a sealed housing eliminating the need to flush the motor prior to or during use. This configuration provides hemodynamic support during high-risk PCI, for sufficient time and safety for a complete revascularization via a minimally invasive approach (rather than an open surgical procedure).

The system has been designed to eliminate the need for motor flushing, provide increased flow performance up to about 4.0 l/min at 60 mmHg with acceptably safe hemolysis due to a computational fluid dynamics (CFD) optimized impeller that minimizes shear stress.

Figure 2:
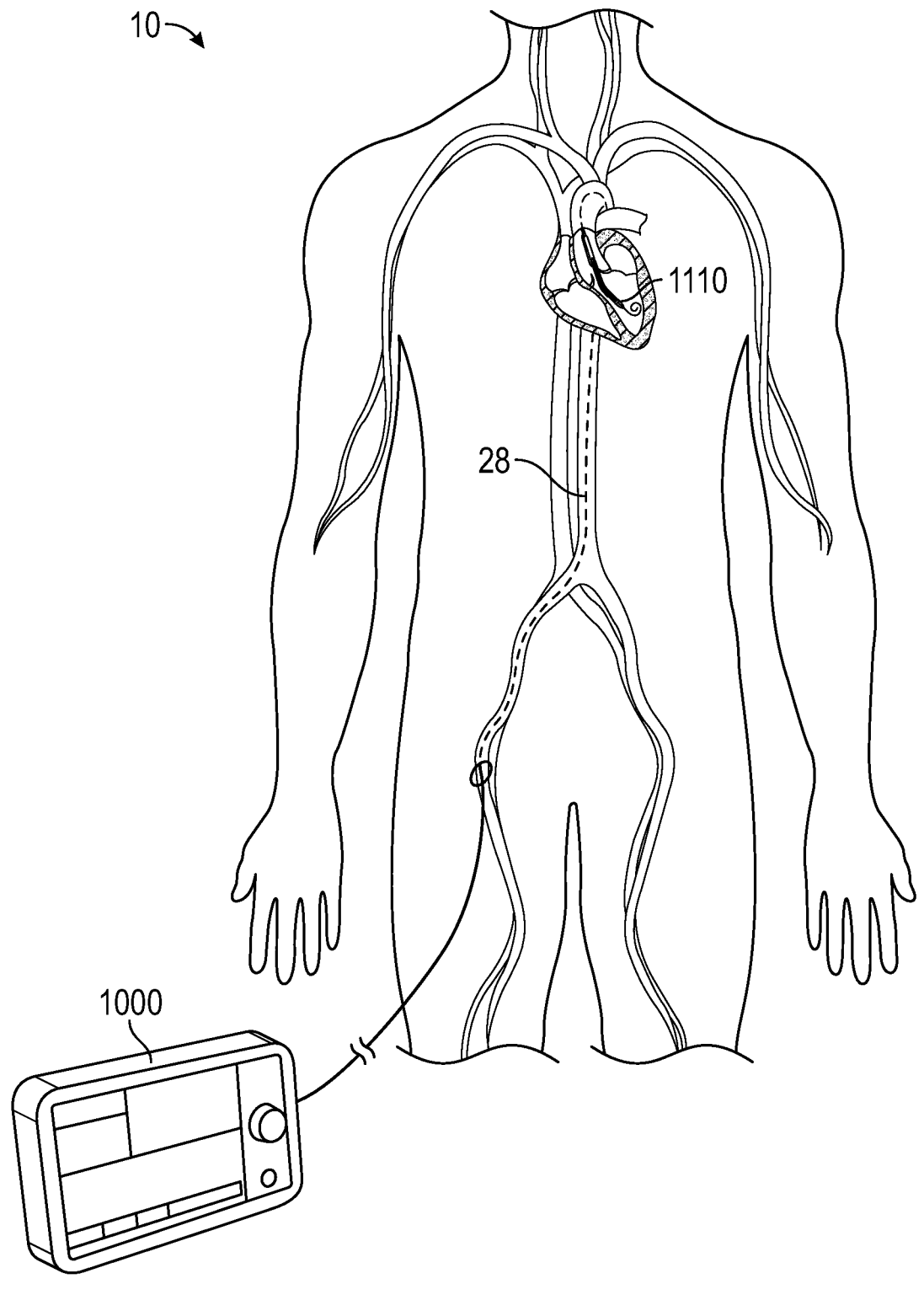
FIG. 2 schematically illustrates the access pathway from the femoral artery to the left ventricle.

The device actively unloads the left ventricle 1114 by pumping blood from the ventricle 1114 into the ascending aorta 1116 and systemic circulation (shown in FIGS. 1 and 2). When in place, the MCS device 1110 can be driven by a complementary MCS Controller 1000 (see, e.g. FIGS. 10A-18D) to provide between 0.4 l/min up to 4.0 l/min of partial left ventricular support. The controller 1000 may be in wired or wireless communication with pump, e.g. to analyze data from sensor and to control rotation of the impeller.

In general, the overall MCS system 10 may include a series of related subsystems and accessories, including one or more of the following. The MCS Device 1110 may include a pump, shaft, proximal hub, insertion tool, proximal cable, infection shield, guidewire guide tube and/or guidewire aid. The MCS Device 1110 may be provided sterile. An MCS shaft may contain the electrical cables and a guidewire lumen for over-the-wire insertion. The proximal hub contains guidewire outlet with a valve to maintain hemostasis and connects the MCS shaft to the proximal cable, that connects the MCS Device 1110 to the MCS Controller 1000. The proximal cable 28 may be 3.5 m (approx. 177 inch) in length and extend from a sterile field 5 to a non-sterile field 3 where the MCS Controller 1000 is located. An MCS insertion tool may be provided premounted on the MCS Device to facilitate the insertion of the pump into the introducer sheath and to protect the inlet tube and the valves from potential damage or interference when passing through the introducer sheath. A peel-away guidewire aid may be pre-mounted on the MCS Device to facilitate the insertion of a guidewire, such as an 0.018" placement guidewire, into the pump and into the MCS shaft, optionally with the MCS insertion tool also pre-mounted such that the guidewire guide tube may pass at least in part through a space between the MCS Device and the MCS insertion tool. A 3 m, 0.018" placement guidewire may be used, having a soft coiled pre-shaped tip for atraumatic wire placement into the left ventricle. The guidewire is provided sterile. A 14 Fr introducer sheath may be used with a usable length of 275 mm to maintain access into the femoral artery and provide hemostasis for a 0.035" guidewire, a diagnostic catheter, the 0.018" placement guidewire, and the insertion tool.

The housing of the introducer sheath may be designed to accommodate the MCS Insertion Tool. The introducer sheath is provided sterile. An introducer dilator may be compatible with the introducer sheath to facilitate atraumatic insertion of the introducer sheath into the femoral artery. The introducer dilator is provided sterile. The MCS Controller 1000 may be used which drives and operates the MCS Device 1110, observes its performance and condition as well as providing error and status information. The powered controller may be designed to support at least about 12 hours of continuous operation and contains a basic interface to indicate and adjust the level of support provided to the patient. Moreover, the controller provides an optical and audible alarm notification in case the system detects an error during operation. The MCS Controller 1000 may be provided non-sterile and be contained in an enclosure designed for cleaning and re-use outside of the sterile field 5. The controller enclosure may contain a socket into which the extension cable is plugged.

In some examples of an insertion process of an MCS device 1110 using two guidewires, the larger, 0.035" guidewire may be inserted first. The larger guidewire may be inserted through, for example, the dilator of the introducer kit with a lumen or through a different access sheath. After insertion, the access sheath may be removed and the introducer with dilator may be advanced over the larger guidewire. The dilater may then be removed from the introducer and a diagnostic catheter may be advanced through the introducer over the guidewire into the heart. The larger guidewire may then be removed and the smaller, 0.018" guidewire may be advanced through the diagnostic catheter. The diagnostic catheter may then be removed to leave the smaller, 0.018" guidewire in the introducer. Then the proximal end of the 0.018" guidewire may be sent through the MCS device via the guidewire aid (which may be external to the body). The guidewire aid may then be removed (such as by being peeled away) and the MCS device (still in the insertion tool) may be inserted into the introducer over the small guidewire. The MCS device may then be advanced over the smaller guidewire distally out of the insertion tool and up to the heart. The insertion tool may then optionally may be retracted from the introducer.

Figure 3:
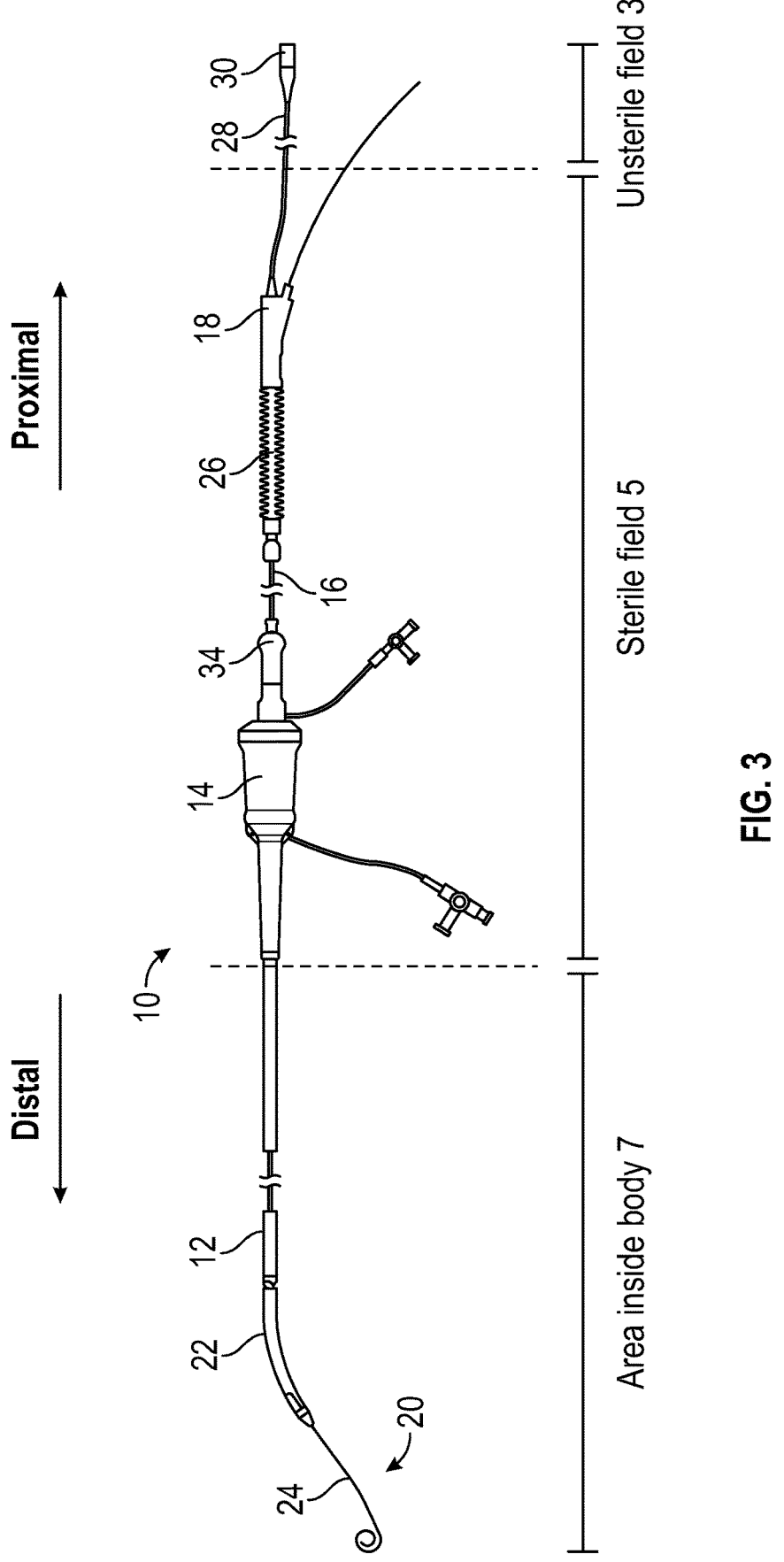
FIG. 3 is a side elevational view of an embodiment of a mechanical circulatory support system in accordance with the present disclosure.

Referring to FIG. 3, there is illustrated an overall MCS system 10 in accordance with one aspect of the present disclosure, subcomponents of which will be described in greater detail below. For reference, the "distal" and "proximal" directions are indicated by arrows in FIGS. 3, 4 and 8A. "Distal" and "proximal" as used herein have their usual and customary meaning, and include, without limitation, a direction more distant from an entry point of the patient's body as measured along the delivery path, and away a direction less distant from an entry point of the patient's body as measured along the delivery path, respectively.

The system 10 may include an introducer sheath 12 having a proximal introducer hub 14 with a central lumen for axially movably receiving an MCS shaft 16. The MCS shaft 16 extends between a proximal hub 18 and a proximal end 20 of a pump 22. The pump may be located at the distal end 20 of the system 10, with a guidewire 24 extending therefrom. The guidewire 24 or 1111 or any other guidewire described herein may have various features, such as those described in U.S. Provisional Application No. 63/224,326, titled GUIDEWIRE and filed Jul. 21, 2021, the entire content of which is incorporated by reference herein for all purposes and forms a part of this specification. The hub 18 may be provided with an integrated microcontroller or memory storage device for device identification and tracking of the running time, which could be used to prevent overuse to avoid excessive wear or other technical malfunction. The microcontroller or memory device could disable the device, for example to prevent using a used device. They could communicate with the controller, which could display information about the device or messages about its usage. An atraumatic cannula tip with radiopaque material allows the implantation/explantation to be visible under fluoroscopy.

The pump 22 comprises a tubular housing. The tubular housing of the pump 22 is used broadly herein and may include any component of the pump 22 or component in the pump region of the system, such as an inlet tube, a distal endpiece, a motor housing, other connecting tubular structures, and/or a proximal back end of the motor housing. The pump 22, for example the tubular housing, is carried by a distal region of the MCS shaft 16. The system 10 is provided with at least one central lumen for axially movably receiving the guidewire 24. The proximal hub 18 is additionally provided with an infection shield 26. A proximal cable 28 extends between the proximal hub 18 and a connector 30 for releasable connection to a control system typically outside of the sterile field 3, to drive the pump 22.

Figure 4:
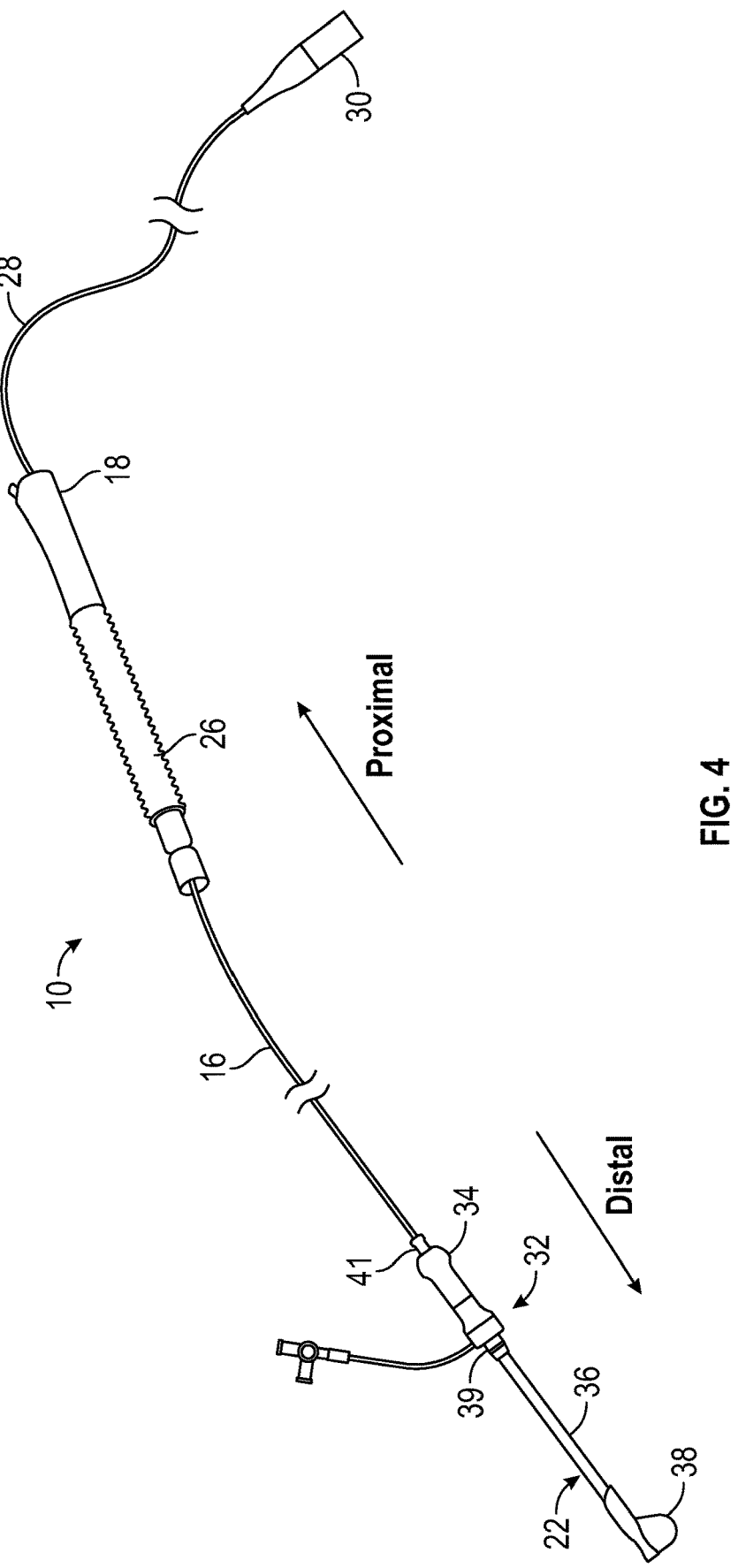
FIG. 4 is the system of FIG. 3, with the introducer sheath removed and including an insertion tool and a guidewire loading aid.

Referring to FIG. 4, the system 10 additionally includes an insertion tool 32. The insertion tool 32 has an elongate tubular body 36. The insertion tool 32 may have a length within the range of from about 85 mm to about 160 mm (e.g., about 114 mm) and an inside diameter within the range of from about 4.5 mm to about 6.5 mm (e.g., about 5.55 mm), extending distally from a proximal hub 34. The tubular body 36 includes a central lumen adapted to axially movably receive the MCS shaft 16 and pump 22 there through, and sufficient collapse resistance to maintain patency when passed through the hemostatic valves of the introducer sheath. As illustrated in FIG. 4, the pump 22 can be positioned within the tubular body 36, such as to facilitate passage of the pump 22 through the hemostatic valve(s) on the proximal end of an introducer hub 14. A marker 37 (such as illustrated in FIG. 7) is provided on the shaft 16 spaced proximally from the distal tip 64 such that as long as the marker 37 is visible on the proximal side of the hub 34, the clinician knows that the pump is within the tubular body 36.

The hub 34 may be provided with a first engagement structure 39 for engaging a complimentary second engagement structure on the introducer sheath to lock the insertion tool into the introducer sheath. The hub 34 may be connected with the infection shield 26 via a connection 41, such as a knob or button that connects via force-fit, screw, or other means. The hub 34 may also be provided with a locking mechanism for clamping onto the shaft 16 to prevent the shaft 16 from sliding proximally or distally through the insertion tool once the MCS device has been positioned at the desired location in the heart. The locking mechanism may be actuated by twisting one or more parts (for example, two parts) of the hub 34. Other actuation means may also be possible. The hub 34 may additionally be provided with a hemostasis valve to seal around the shaft 16. In some embodiments, the hub 34 may accommodate passage of the larger diameter MCS device which includes the pump. In one commercial presentation of the system, the MCS device as packaged is prepositioned within the insertion tool and the guidewire aid 38 is preloaded within the MCS device and shaft 16, as illustrated in FIG. 4. In some examples, the MCS device is configured to be prepositioned in the tube 36 and advanced distally. In such a configuration, the lumen in the hub 34 may be smaller than the MCS device and only the shaft 16 may be configured to pass through the hub 34. When removing the pump from the body, the MCS device may be pulled into the tube 36 and then the insertion tool may be pulled out of the introducer with the pump in the tube 36. Further details of a guidewire aid 38 are discussed, for example, with reference to FIGS. 8A and 8B.

Figure 5:
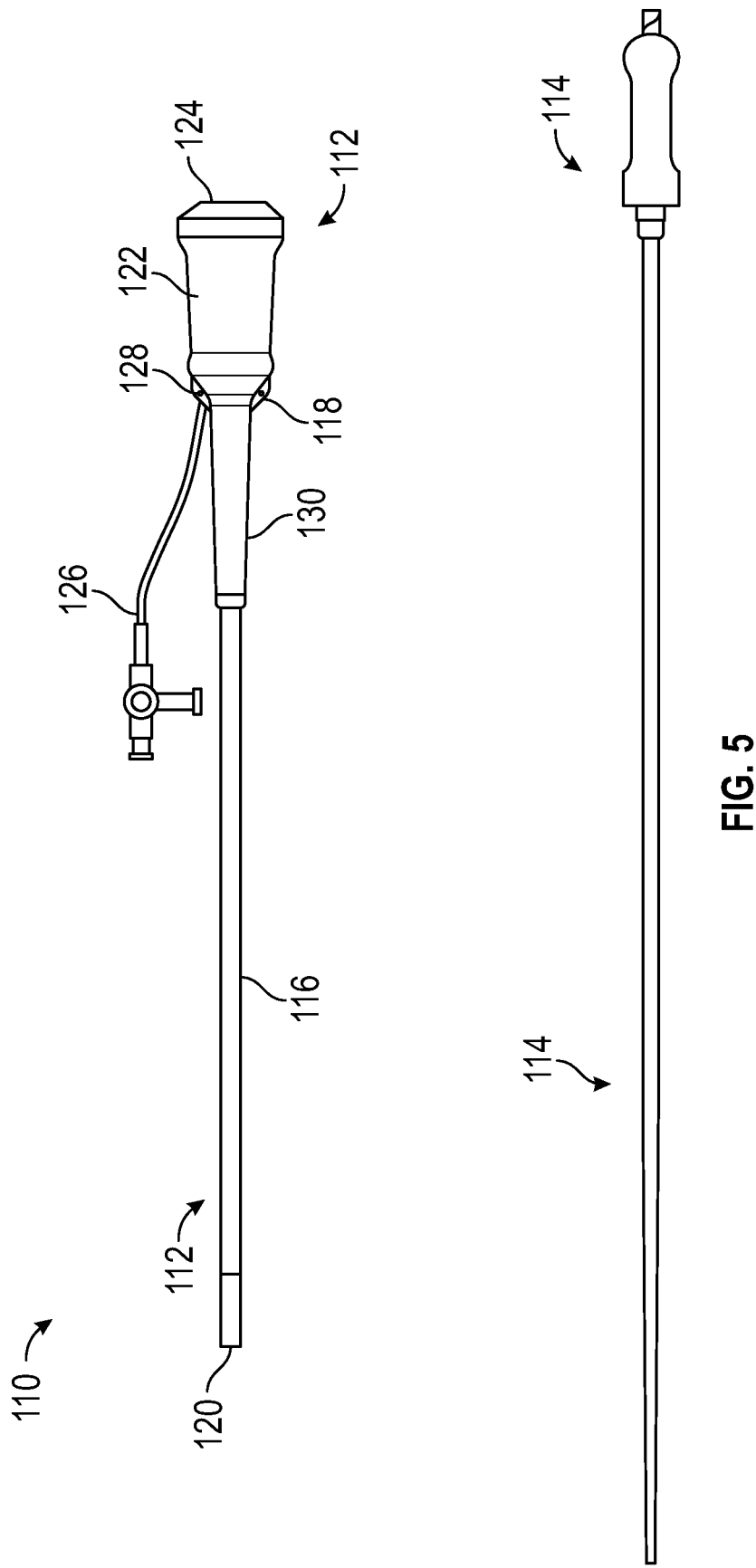
FIG. 5 shows an introducer kit having a sheath and dilator.
Figures 6, 7:
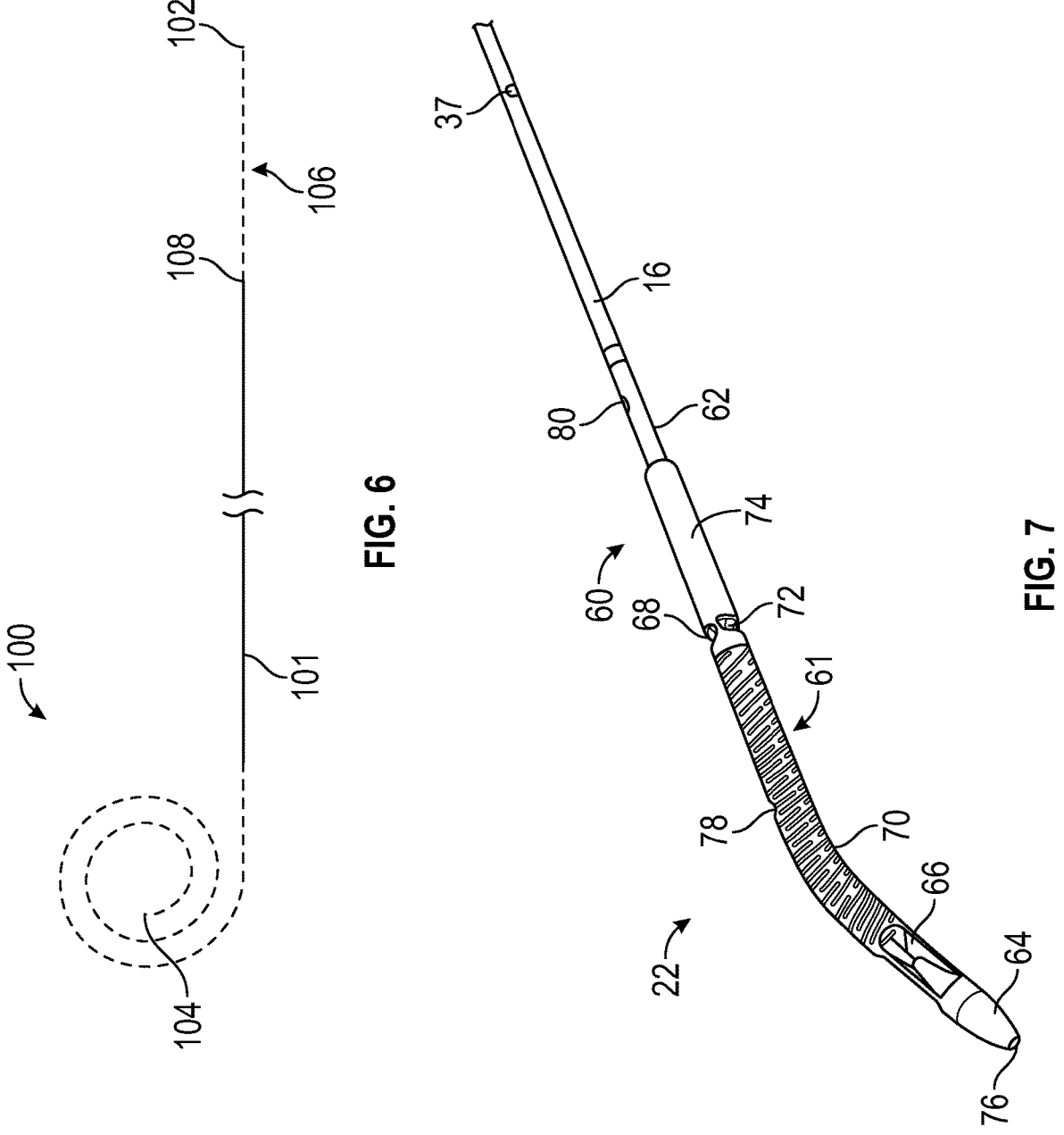
FIG. 6 shows an embodiment of a placement guidewire.
FIG. 7 is a partial perspective view of a distal, pump region of the MCS device.

Referring to FIGS. 5 and 6, an introducer kit 110 may include an introducer sheath 112, a dilator 114, a guidewire 100, and/or a guidewire aid 38, such as discussed with reference to FIGS. 8A and 8B. The guidewire 100 (e.g., 0.018" placement guidewire) may comprise an elongate flexible body 101 extending between a proximal end 102 and a distal end 104. A distal zone of the body 101 may be pre-shaped into a J tip or a pigtail, as illustrated in FIG. 6, to provide an atraumatic distal tip. A proximal zone 106 may be configured to facilitate threading through the MCS device, and extends between the proximal end 102 and a transition 108. The proximal zone 106 may have an axial length within the range of from about 100 mm to about 500 mm (e.g., about 300 mm).

The introducer kit 110 may comprise the sheath 112 and/or the dilator 114. The sheath 112 may comprise an elongate tubular body 116, extending between a proximal end 118 and a distal end 120. The tubular body 116 terminates proximally in a proximal hub 122. Optionally, the tubular body 116 may be expandable or may be peeled apart. The proximal hub 122 may include a proximal end port 124 in communication with a central lumen extending throughout the length of the tubular body 116 and out through a distal opening, configured for axially removably receiving the elongate dilator 114. The proximal hub 122 may additionally be provided with a side port 126, at least one and optionally two or more attachment features such as an eye 128 to facilitate suturing to the patient, and at least one and optionally a plurality of hemostasis valves for providing a seal around a variety of introduced components such as a standard 0.035" guidewire, a 5 Fr or 6 Fr diagnostic catheter, an 0.018" placement guidewire 100, the shaft 16, and the insertion tool 32.

FIG. 7 illustrates additional details of a distal pump region 60 of the MCS system showing the device or pump 22 and a distal portion of the catheter shaft 16. The pump zone or region 60 extends between a bend relief 62 at the distal end of shaft 16 and a distal tip 64. The pump 22 include a tubular housing 61, which may include an inlet tube 70, a distal tip 64, and/or a motor housing 74. The tubular housing 61 may include one or more pump inlets 66 and/or outlets 68, which may be part of the inlet tube 70, or part of other structures such as an intermediate structure joining a proximal end of the inlet tube 70 to the motor housing 74. A guidewire guide aid, as further described herein, may extend into and out of various components of the system, such as the tubular housing 61 of the pump 22 and/or the catheter shaft 16 (e.g., bend relief 62).

The pump inlet 66 comprising one or more windows or openings is in fluid communication with a pump outlet 68 comprising one or more windows or openings by way of a flow path extending axially through the inlet tube 70. The pump inlet 66 may be positioned at about the transition between the inlet tube 70 and the proximal end of distal tip 64. The pump inlet 66 may be generally within about 5 cm, 3 cm, or less distance from the distal port 76.

In some embodiments, the distal tip 64 is radiopaque. For example, the distal tip may be made from a polymer containing a radiopacifier such as barium sulfate, bismuth, tungsten, iodine. In some embodiments, an entirety of the MCS device is radiopaque. In some embodiments, a radiopaque marker is positioned on the inlet tube between the pump outlet 68 and the guidewire port 78 to indicate the current position of the aortic valve.

The inlet tube 70 may comprise a highly flexible slotted (e.g., laser cut) metal (e.g., Nitinol) tube having a polymeric (e.g., Polyurethane) tubular layer to isolate the flow path. Inlet tube may have an axial length within the range of from about 60 mm and about 100 mm and in one implementation is about 67.5 mm. The outside diameter may be within the range of from about 4 mm to about 5.4 mm, and in one implementation is about 4.66 mm. The connections between the inlet tube and the distal tip and to the motor may be secured such as through the use of laser welding, adhesives, threaded or other interference fit engagement structures, or may be via press fit.

Figures 9A, 9B:
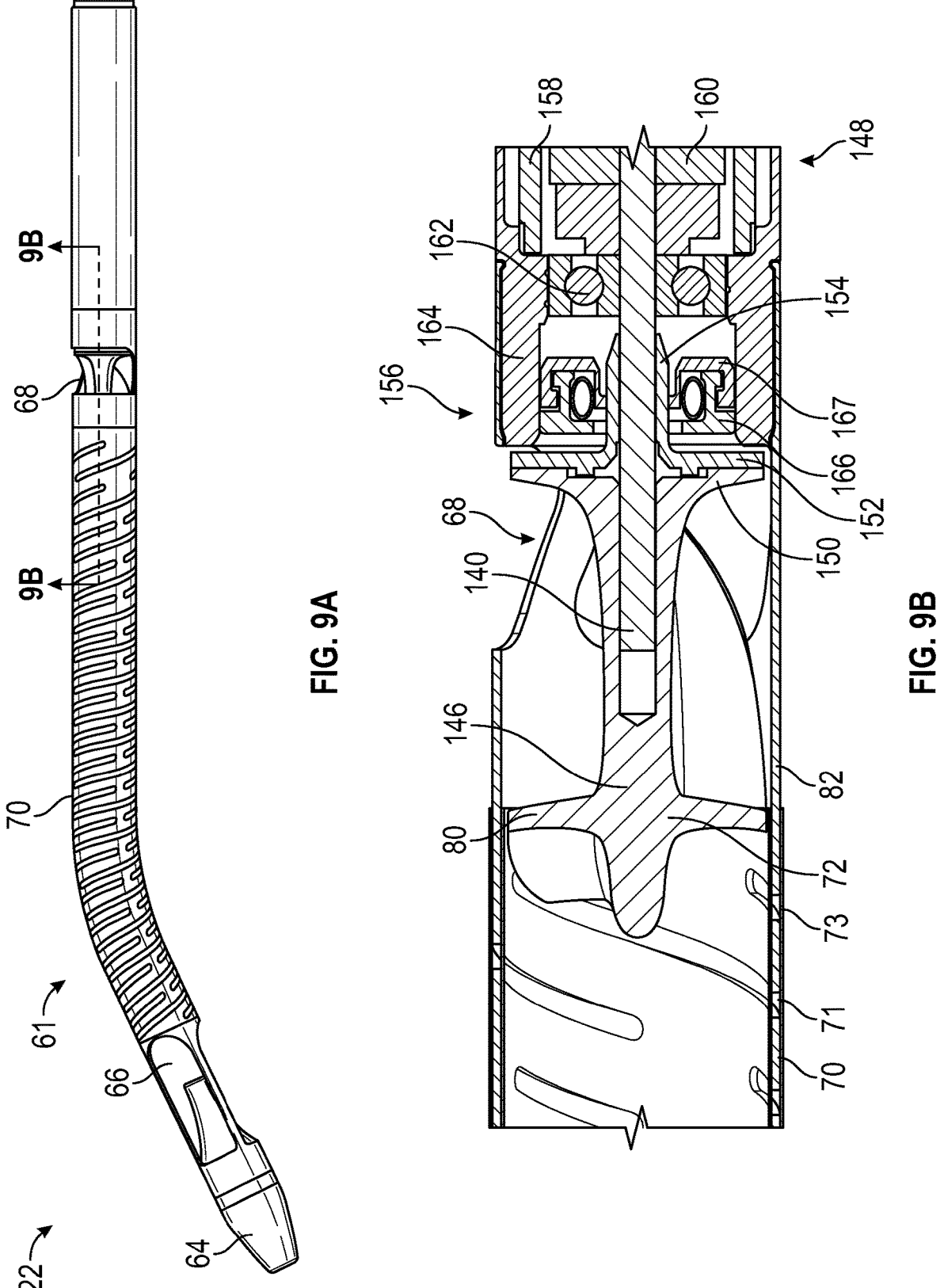
FIGS. 9A and 9B are respectively a side view of a pump region of the MCS device and a cross sectional view through the impeller region of the MCS device.

An impeller 72 may be positioned in the flow path between the pump inlet 66 and pump outlet 68 (see also FIGS. 9A and 9B). In the illustrated embodiment, the impeller 72 is positioned adjacent to the pump outlet 68. As is discussed further below, the impeller 72 is rotationally driven by a motor contained within a motor housing 74, on the proximal side of the impeller 72.

Figures 8A, 8B:
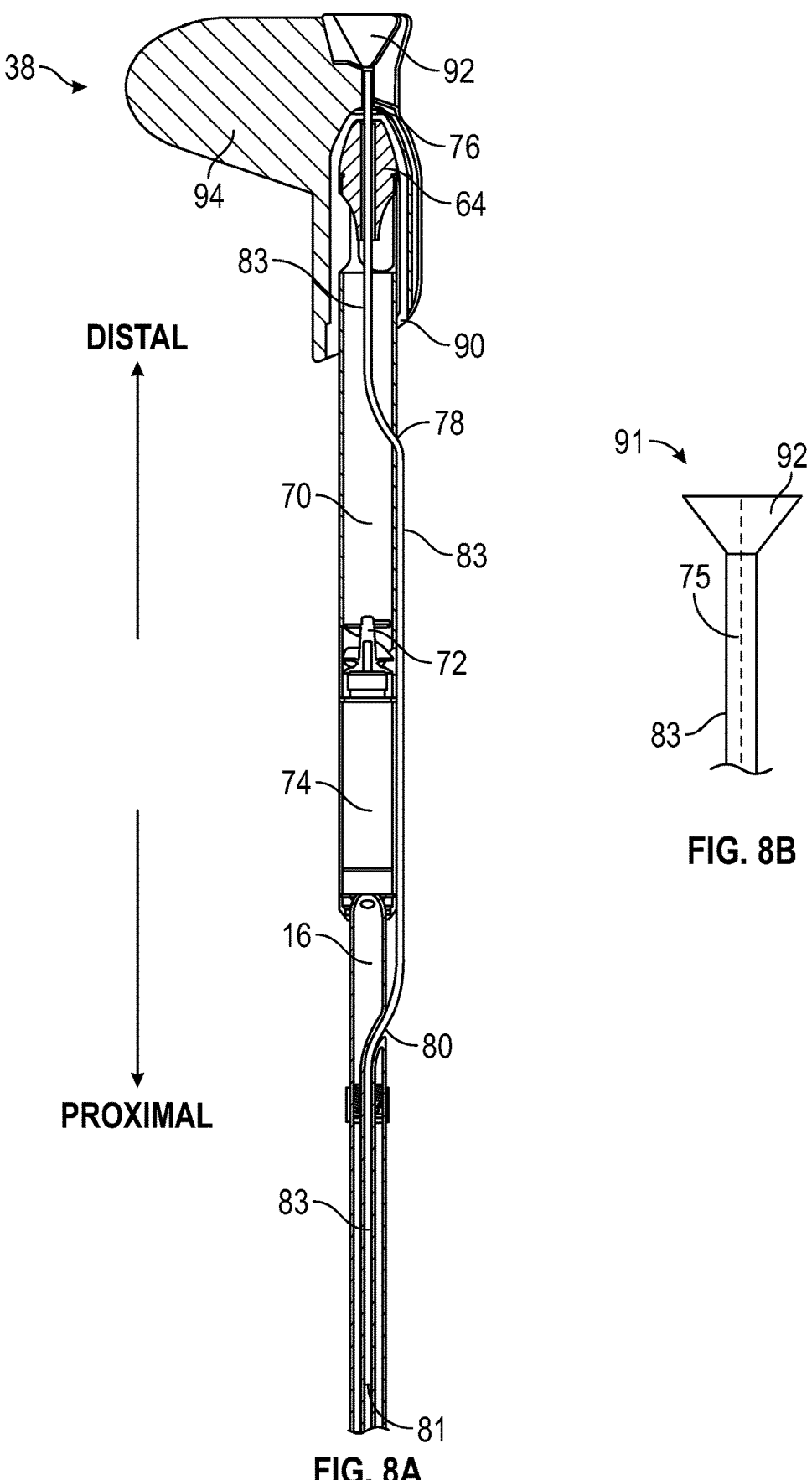
FIGS. 8A and 8B are a side elevational view and close up detail view respectively of a distal region of the MCS device, showing the guidewire guide tube defining the guidewire path and the guidewire back loading aid in place.

FIGS. 8A and 8B are a side cross-sectional view and a detail view respectively of the pump region showing an embodiment of a guidewire aid 38. The MCS device can be provided in either a rapid exchange configuration or over the wire configuration. A first guidewire port 76 such as a distal-facing opening on distal face of the distal tip 64 may be in communication, via a first guidewire lumen through the distal tip 64 and at least a portion of the flow path in the inlet tube 70, with a second guidewire port 78 such as an opening extending through a side wall of the inlet tube 70, and distal to the impeller 72. This could be used for rapid exchange, with the guidewire 100 extending proximally alongside the catheter from the second guidewire port 78.

The catheter may be provided in an over the wire configuration, in which the guidewire 100 extends proximally throughout the length of the catheter shaft 16 through a guidewire lumen therein. In the over the wire embodiment, for example of FIGS. 7, 8A and 8B, however, the guidewire 100 exits the inlet tube 70 via the second guidewire port 78, extends proximally across the outside of the impeller and motor housing, and reenters the catheter shaft 16 via a third guidewire port 80, which may be an opening in the sidewall of the catheter shaft or of a proximal component of the pump, housing, or backend. The third guidewire port 80 may be located proximal to the motor, and, in the illustrated embodiment, is located on the bend relief 62. The third guidewire port 80 is in communication with a guidewire lumen of the catheter shaft 16 which extends proximally throughout the length of the shaft 16 and exits at a proximal guidewire port carried by or located within the proximal hub 18 (see FIG. 4).

As shown in FIG. 8A, the pump may be provided assembled with the removable guidewire aid 38. The guidewire aid 38 may have a guidewire guide tube 83. The guide tube 83 may be a cylindrical or other closed cross-sectional shape extending axially. The guide tube 83 may be a flexible material such as polyimide. The guide tube 83 may be adapted to be peeled apart longitudinally, such as having a longitudinal slit or tear line. The inside surface of the guide tube 83 may be provided with a lubricious coating, such as PTFE. The guide tube 83 may track the intended path of the guidewire 100 from the first guidewire port 76, proximally through the tip 64 and back outside of the inlet tube via second guidewire port 78, and back into the catheter shaft 16 via the third guidewire port 80. In the illustrated implementation, the guidewire guide tube 83 extends proximally within the catheter shaft 16 to a proximal end 81 of the guide tube 83, in communication with or within the guidewire lumen which extends to the proximal hub 18. The proximal end 81 of the guide tube 83 may be positioned within about 5 mm or 10 mm of the distal end of the shaft 16, or may extend into the catheter shaft guidewire lumen for at least about 10 mm or 20 mm, such as within the range of from about 10 mm to about 50 mm. In some embodiments, the third port 80 may be located within a proximal end of the tubular housing, such as the motor housing or backend, or in any other components of the device at a location that is proximal to the impeller.

The guidewire aid 38 may have a funnel 92. The funnel 92 may be located at a distal end of the guide tube 83 and provided pre-positioned at a distal end of the inlet tube, for example at the distal tip 64. The funnel 92 may increase in width in the distal direction, from a narrow proximal end in communication with the guide tube 83, to a wider distal opening at a distal end of the funnel 92. The funnel 92 may be conical, frustoconical, pyramidal, segmented, or other shapes. A proximal end of the funnel 92 may be attached to a distal end of the guidewire guide tube 83. The proximal end 102 of the guidewire 100 (see FIG. 6) may be inserted into the funnel 92, passing through the first (distal) guidewire port 76 and guided along the intended path by tracking inside of the guidewire guide tube 83. The guidewire guide tube 83 may then be removed by sliding the guide tube 83 distally out of the distal tip 64 and peeling it apart longitudinally, leaving the guidewire 100 in place.

The guidewire aid 38 may have a pull tab 94. In some embodiments, a distal end of the guidewire guide tube 83 is attached to the pull tab 94 of the guidewire aid 38. The pull tab 94 may be a structure capable of being gripped by a human hand, for example with a lateral, planar extension as shown. The guidewire aid 38, for example, the pull tab 94, the guide tube 83 and/or the funnel 92, may be provided with a tearable line 75, as more clearly seen in FIG. 8B. The tearable line 75 line may be an axially extending split line. The tearable line 75 may include a weakening, a slot, or a perforated linear region. Removal of the guidewire aid 38 may be accomplished such as by grasping the pull tab 94 and pulling out the guidewire tube 83 and/or funnel 92 and removing them from the guidewire 100 as they split or peel away along the split line 75, such as shown in the detailed inset 91 of FIG. 8B.

The guidewire aid 38 may include a proximal opening 90 configured to slip over and removably receive the distal tip 64 and/or struts at the distal end of the inlet tube 70 that define windows of the pump inlet 66. The guidewire guide tube 83 having a lumen therethrough is positioned within the proximal opening 90 and aligned to pass through the guidewire port 76 of the distal tip 64. The proximal opening 90 may further be configured to slip over and removably receive a distal end of tubular body 36 of an insertion tool 32 as shown in FIG. 4. The MCS system may be dimensioned so that an annular space defined between the outer surface of the MCS device—such as the inlet tube 70, motor housing 74, or MCS catheter bend relief 16—and the inner surface of the tubular body 36 of the insertion tool 32, may removably receive the guidewire guide tube 83 therein, when the MCS device, guidewire aid 38 and insertion tool 32 are assembled together.

In some embodiments, the lumen of the guidewire guide tube 83 is in communication with the distal flared opening of the funnel 92 which gets larger in cross-section in the distal direction. The guidewire aid 38 may be provided assembled on the MCS pump with the guidewire guide tube 83 pre-loaded along a guidewire path, for example into the MCS pump through port 76, through a portion of the fluid path within the inlet tube 70, out of the MCS pump through port 78, along the exterior of the MCS pump and back into the shaft 16 through port 80. This helps a user guide the proximal end of a guidewire into the funnel 92 through the guidewire path and into the guidewire lumen of the MCS shaft 16. The pull tab 94 may be provided on the guidewire aid 38 to facilitate grasping and removing the guidewire aid, including the guidewire guide tube 83, following loading of the guidewire. The guidewire aid 38 may have a longitudinal slit or tear line 75, for example along the funnel 92, proximal opening 90 and guidewire guide tube 83, to facilitate removal of the guidewire aid 38 from the MCS pump 22 and guidewire 100.

The guidewire aid 38 features described herein may be used with a variety of different MCS systems and/or pump devices. The guidewire aid 38 may be used for guidewire paths that enter and exit a pump housing, as described, or that do not exit a housing. The guidewire aid 38 is described herein as being used with an MCS system configured for temporary operation for high-risk PCI procedures. The system may include rotating impeller with a radial shaft seal and a motor rotating the impeller via a shaft extending through the seal. The guidewire aid 38 may be used with a variety of different devices. The guidewire aid 38 may also be used with a pump having a magnetic drive, where the motor rotates a first magnet within a sealed motor housing that magnetically communicates with a second magnet of the impeller that is external to the sealed housing to rotate the impeller. Thus, the guidewire aid 38 is not limited to use with only the particular pump embodiments described herein.

FIGS. 9A and 9B depict side views and a partial cross-section view respectively of the pump 22. As shown, the impeller 72 may be attached to a short, rigid motor drive shaft 140. The drive shaft 140 may extend distally into a proximally facing central lumen 142 in the impeller 72, such as through a proximal extension 154 on the impeller hub 146, where it may be secured by a press fit, laser weld, adhesives or other bonding technique. The impeller 72 may include a radially outwardly extending helical blade 80, which, at its maximum outside diameter, is spaced apart from the inside surface of tubular impeller housing 82 within the range of from about 40 μm to about 120 μm. Impeller housing 82 may be a proximal extension of the inlet tube 70, on the proximal side of the slots 71 formed in the inlet tube 70 to provide flexibility distal to the impeller. A tubular outer membrane 73 may enclose the inlet tube and seals the slots 71 while preserving flexibility of the inlet tube. The one or more pump outlets 68 may be formed in the sidewall of the impeller housing, axially aligned for example with a proximal portion of the impeller (e.g., a proximal 25% to 50% portion of the impeller.

The impeller may comprise a medical grade titanium. This enables a CFD optimized impeller design with minimized shear stress for reduced damage of the blood cells (hemolysis) and a non-constant slope increasing the efficiency. This latter feature cannot be accomplished with a mold-based production method. Electro polishing of the surface decreases the surface roughness to minimize the impact on hemolysis.

In one implementation of the invention, the impeller hub 146 may flare radially outwardly in a proximal direction to form an impeller base 150, which may direct blood flow out of the outlets 68. A proximal surface of the impeller base 150 may be secured to an impeller back 152, which may be in the form of a radially outwardly extending flange, secured to the motor shaft 140. For this purpose, the impeller back 152 may be provided with a central aperture to receive the motor shaft 140 and may be integrally formed with or bonded to a tubular sleeve 154 adapted to be bonded to the motor shaft 140. In one implementation, the impeller back 152 may be first attached to the motor shaft 140 and bonded such as through the use of an adhesive. In a second step, the impeller 72 may be advanced over the shaft and the impeller base 150 bonded to the impeller back 152 such as by laser welding.

The distal opening in the aperture in impeller back 152 may increase in diameter in a distal direction, to facilitate application of an adhesive. The proximal end of tubular sleeve 154 may decrease in outer diameter in a proximal direction to form and entrance ramp for facilitating advancing the sleeve proximally over the motor shaft and through the motor seal 156, discussed further below.

The motor 148 may include a stator 158 having conductive windings surrounding a cavity which encloses motor armature 160 which may include a plurality of magnets rotationally secured with respect to motor shaft 140. The motor shaft 140 may extend from the motor 148 through a rotational bearing 162 and also through a seal 156 before exiting the sealed motor housing 164. The seal 156 may include a seal holder 166 which supports an annular seal 167 such as a polymeric seal ring. The seal ring may include a central aperture for receiving the sleeve 154 and is biased radially inwardly against the sleeve 154 to maintain the seal ring in sliding sealing contact with the rotatable sleeve 154. The outside surface of the sleeve 154 may be provided with a smooth surface such as by electro polishing, to minimize wear on the seal.

The pump may include a sealed motor due to the short time of usage for high risk PCI (typically no more than about 6 hours), configured for use without flushing or purging. This provides the opportunity to directly bond the impeller on the motor shaft as discussed in further detail below, removing issues sometimes associated with magnetic coupling such as the additional stiff length, space requirements or pump efficiency. In some embodiments, the pump may include one or more of the seal features described herein with respect to FIGS. 26A-26C. A four pole motor design may be used, which enables flow performance up to 4.0 liters per minute (l/min) at 60 millimeters of mercury (mmHg) with low temperature change. The motor cable interface may be provided with a high tensile strength for explanation.

Figure 10A:
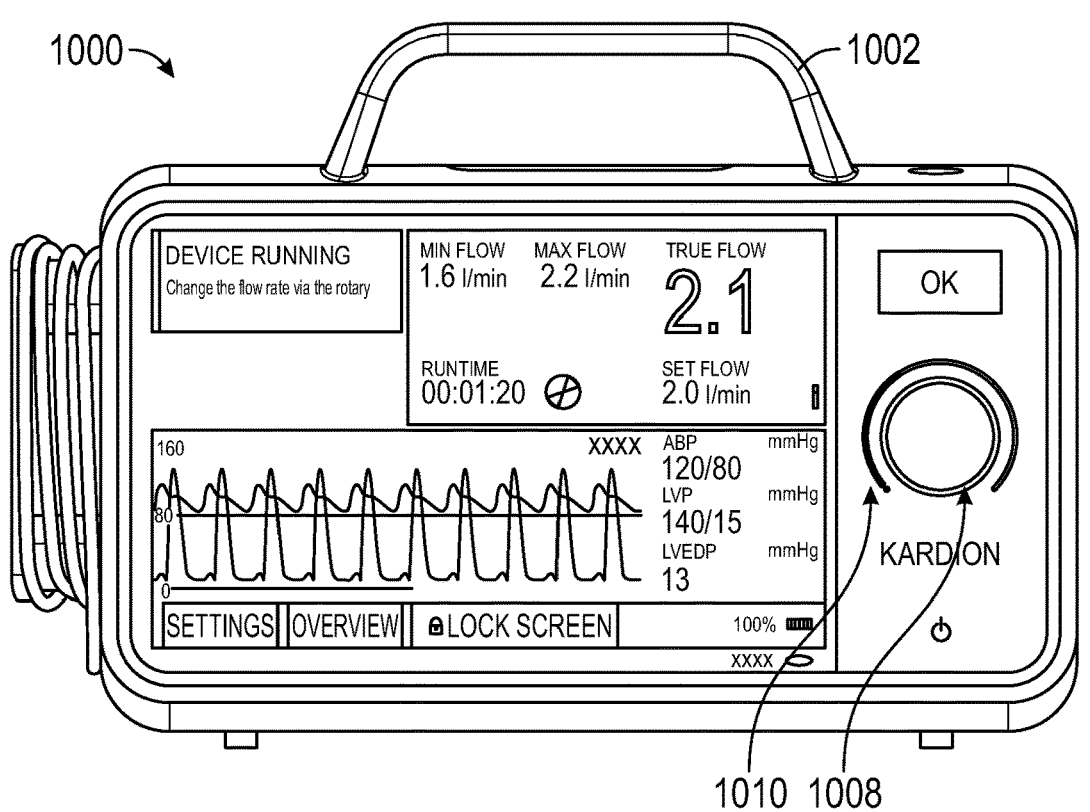
FIG. 10A is a front elevational view of an MCS controller.
Figure 10B:
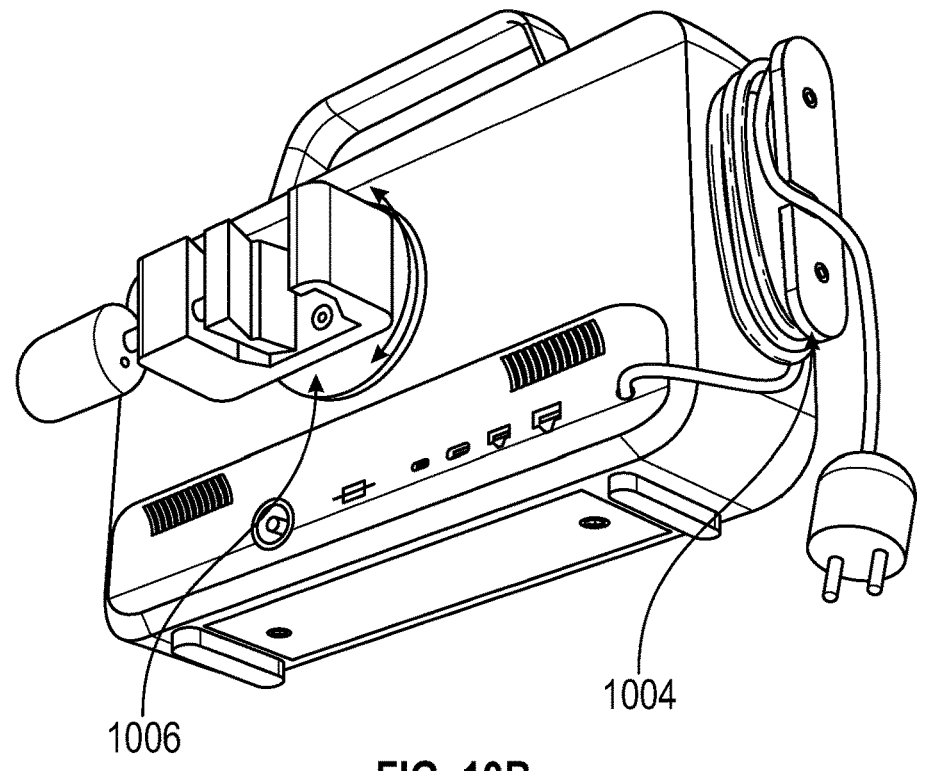
FIG. 10B is a rear perspective view of the MCS controller.

FIGS. 10A and 10B show a front and a back view of an embodiment of MCS controller or controller 1000. The controller 1000 may support operation of one or more cardiac or circulatory support systems, such as left ventricular support devices, ventricular assist devices, or MCS devices as described herein. The controller 1000 may include one more modules to provide power to the cardiac support systems. The controller 1000 may house electronic circuits to send and receive operational signals to the cardiac support system. The controller 1000 may house one or more hardware processors as described below to receive and process data, such as sensor data, from the cardiac support system. In some embodiments, the controller 1000 may have an integrated or self-contained design in which all or almost all of the components required for operation of the controller are housed within the controller. For example, any power supply components, such as transformers or AC/DC converters, may be housed within the controller 1000. As shown in FIG. 2, the controller 1000 may be wired to the pump via electronic wires extending through the catheter shaft 62 to the pump.

In some embodiments, the controller 1000 may include communications systems, or any other suitable systems, to allow the controller 1000 to be adapted to new or modified uses after construction of the controller. For example, multiple modes of wired or wireless communication can be integrated within the controller 1000 to communicate with outside technology, such as, for example, RF, wifi, and/or Bluetooth. In some embodiments, the controller 1000 may have an RFID reader. In some embodiments, the controller 1000 may have systems or components that enable syncing patient data, telemedicine, patient monitoring, real time data collection, error reporting, and/or sharing maintenance records.

The controller 1000 may include a housing for these modules that support any of the cardiac support systems described herein. The housing may further include a handle 1002 to support portability. In contrast to some of the other controllers, such as Abiomed's Impella Controller, the controller 1000 may not include components required for purging. For example, the controller 1000 does not include a cassette for purging. The cassette typically delivers rinsing fluid to the catheter. However, the cassette requires significant real estate and makes the housing bigger and heavier. Due to the design improvements described herein, such as bearing design and sealed motor discussed herein, the controller 1000 does not include a cassette. Furthermore, in some embodiments, the controller 1000 does not require a port for receiving a purging tube. Accordingly, the controller 1000 may be light and compact to support portability.

Figure 13:
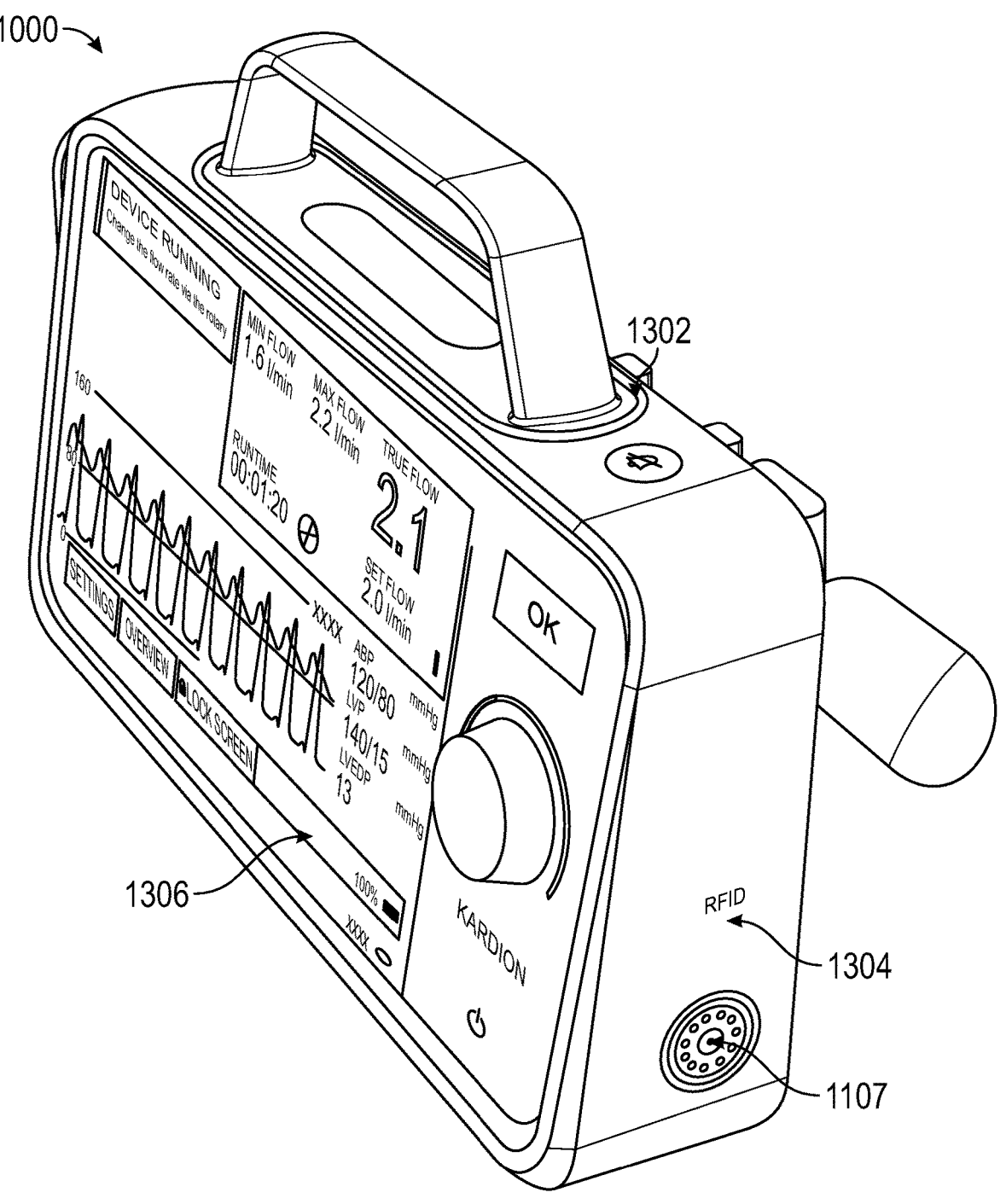
FIG. 13 illustrates a side perspective view of the MCS controller.

The controller may also include a cable management support 1004. In some embodiments, the cable management support 1004 is positioned on one end or side of the controller 1000. The controller 1000 may also include a mount 1006 that may support mounting the controller to a pole in a clinical environment. The mount 1006 may rotate about an axis to support horizontal or vertical clamping. The mount 1006 may be rapidly locked into the desired orientation by quick fastening with a slipping clutch. In some instances, the mount 1006 is positioned away from the cable management support 1004. Furthermore, in some embodiments, the cable management support 1004 is positioned on a left end of the controller 1000 as shown in FIG. 10A. The port 1107 (such as shown in FIG. 13) can be positioned on a side opposite from the cable management support 1004. In some instances, the control element 1008 discussed below is positioned on a side opposite from the cable management support 1004 and in close proximity to the port 1107. This may enable a user to have an improved interaction with the active components of the controller 1000. Therefore, the arrangement of all these elements in the controller 1000 as illustrated can improve operational experience and improve portability.

The controller 1000 can include a control element 1008. In some embodiment, the control element 1008 can provide a haptic feedback. The control element 1008 can include a push button rotary dial. The control element 1008 can enable a user to change parameters on the controller 1000 to control one or more processes described herein. The control element 1008 may also include status indicator 1010 as illustrated in FIG. 10A. In some embodiments, the controller 1000 may include a separate confirmation control element. Furthermore, in some embodiments, aside from the separate confirmation control element, all the parameters can be modified using a single control element 1008. The grouping of controls in a dedicated area can improve user experience.

Figure 11:
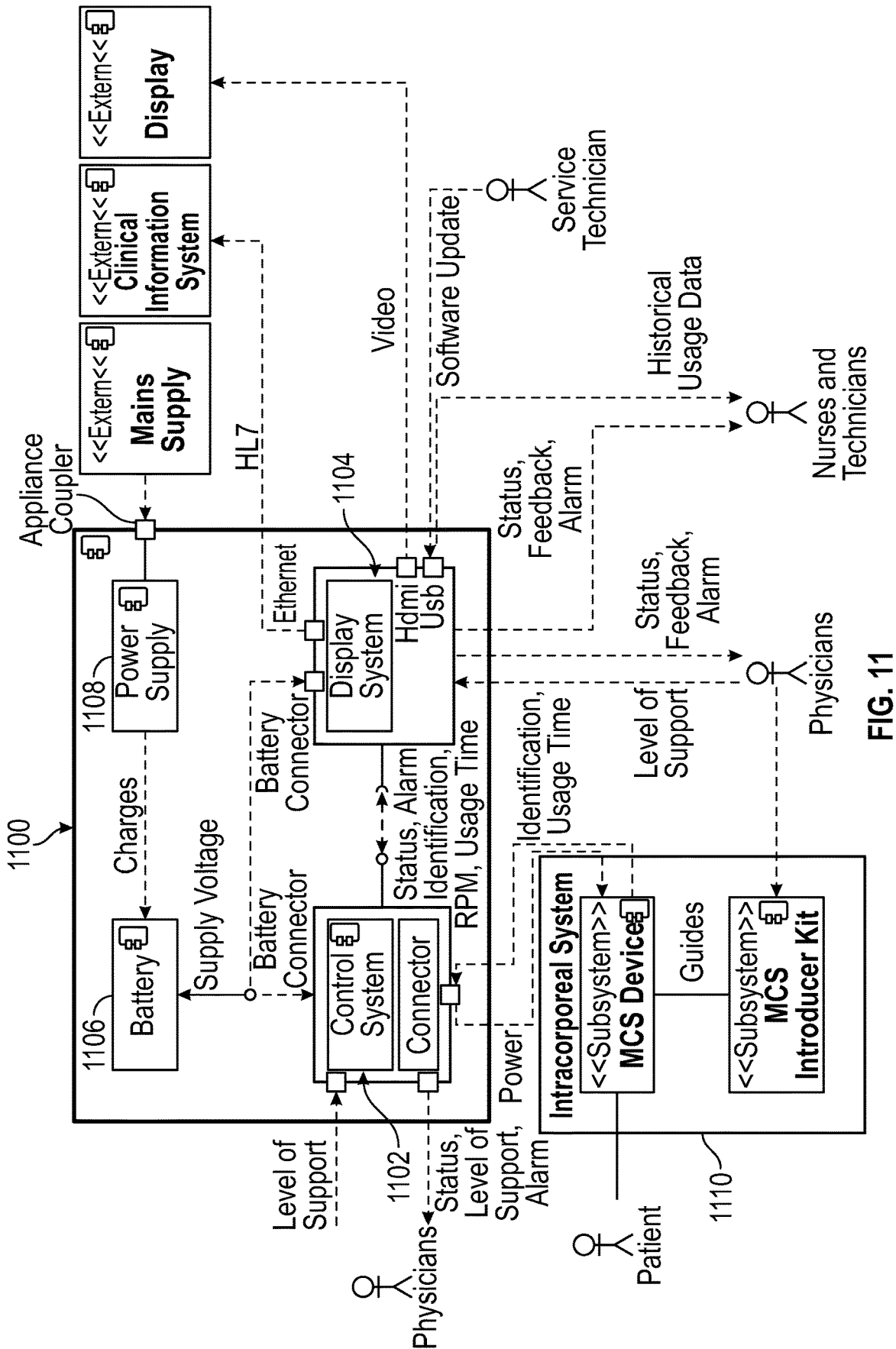
FIG. 11 illustrates a block diagram of an electronic system that can be housed inside the controller of FIGS. 10A and 10B.

FIG. 11 illustrates a block diagram of an electronic system 1100 that can be included in the controller 1000. In some embodiments, the electronic system 1100 can include one or more circuit boards in conjunction with one or more hardware processors for controlling MCS device 1110. The electronic system 1100 can also receive signals, process signals, and transmit signals. The electronic system 1100 can further generate a display and/or alarms. The electronic system 1100 can include a control system 1102 and a display system 1104. In some embodiments, the display system 1104 can be integrated into the control system 1102 and is not separate as shown in FIG. 11. In some embodiments, it may be advantageous for the display system 1104 to be separate from the control system 1102. For example, in the event of failure of the control system 1102, the display system 1104 can serve as a backup.

The control system 1102 can include one or more hardware processors to control various aspects of the MCS device 1110. For example, the control system 1102 can control a motor of the MCS device 1110. The control system 1102 can also receive signals from the MCS device 1110 and process parameters. The parameters can include, for example, flow rate, motor current, ABP, LVP, LVEDP, etc. The control system 1102 can generate alarms and status of the controller 1100 and/or MCS device 1110. In some embodiments, the control system 1102 can support multiple MCS devices 1110. The control system 1102 can transmit the generated alarms or status indicators to the display system 1104. The display system 1104 can include one or more hardware processors to receive processed data from the control system 1102 and render the processed data for display on a display screen. The control system 1102 can also include a memory for storing data.

The electronic system 1100 can also include a battery 1106 that can enable its electronics systems to operate without connection to an external power supply. The power supply interface 1108 can charge the battery 1106 from the external power supply. The control system 1102 can use the battery power to supply current to the motor of the MCS device 1110.

The one or more hardware processors can include microcontrollers, digital signal processors, application specific integrated circuit (ASIC), a field programmable gate array (FPGA) or other programmable logic device, discrete gate or transistor logic, discrete hardware components, or any combination thereof designed to perform the functions described herein.

Figure 12:
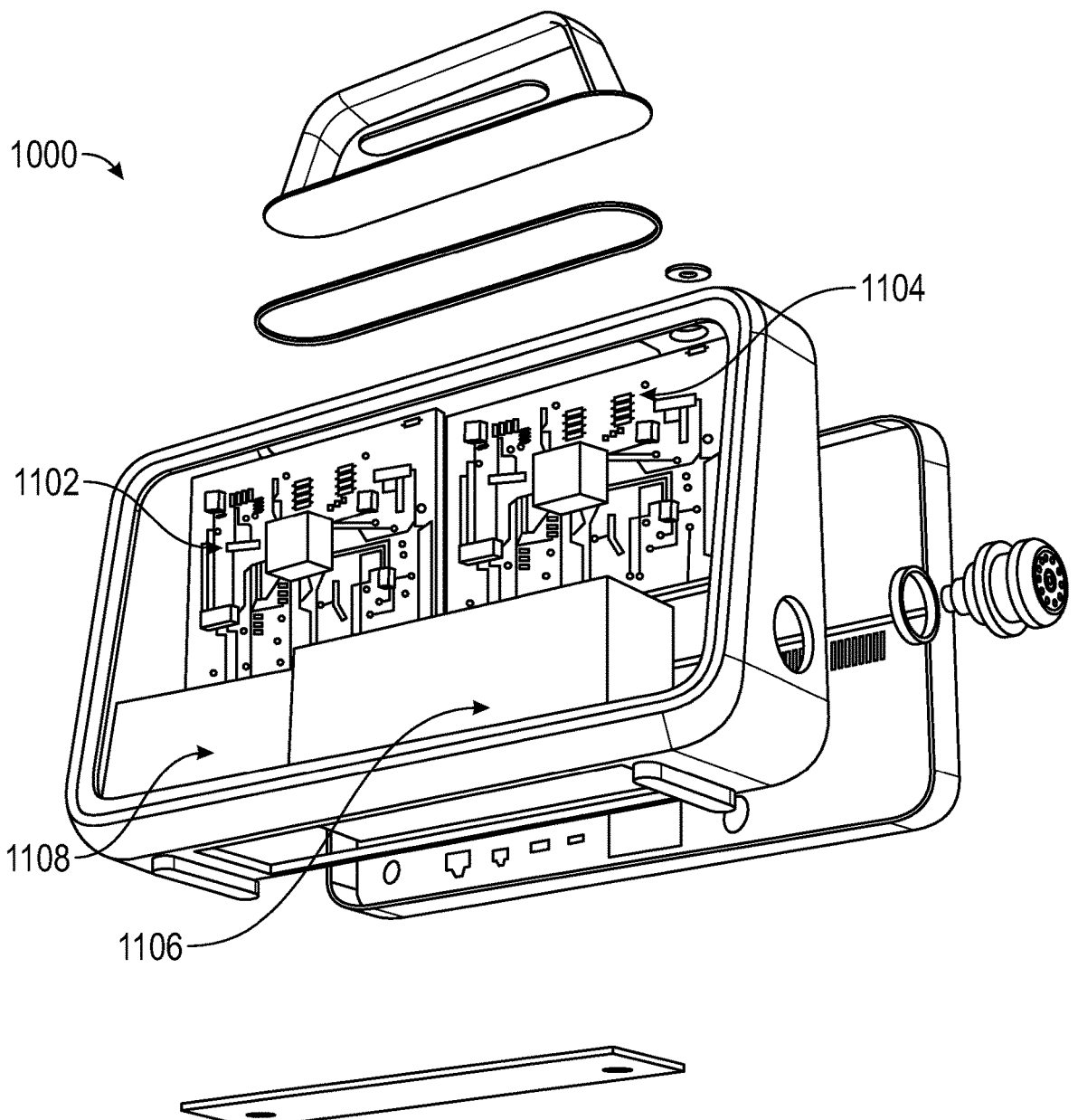
FIG. 12 illustrates an exploded view with components of the electronic system of FIG. 11 inside the controller.

FIG. 12 is an exploded view of an embodiment of the controller 1000 having physical components corresponding to the features of the block diagram schematic of the electronics system 1100 of FIG. 11. As shown in FIG. 12, the controller 1000 may include the control system 1102 and display system 1104 including circuit boards arranged within the housing. The battery 1106 may be located within the bottom section of the housing. The power supply interface 1108 may be located within a corner of the housing.

FIG. 13 is a front perspective view of the controller 1000. In some embodiments, the controller 1000 can include an alarm feedback system, which can provide feedback to an operator regarding the operation of the MCS system. In some embodiments, the alarm feedback system can be in the form of an LED 1302 as illustrated. The LED 1302 may be positioned so that it can be seen by an operator using the controller. As illustrated, the LED 1302 is positioned around the handle 1002. Therefore, it can be seen from positions 360° around the controller. The LED 1302 may be in the form of a ring (oval, oblong, circular, or any other suitable shape) wrapping the handle 1002. Such an LED 1302 may be visualized from any direction as long as the top of the controller is viewable. The control system 1102 can generate different colors or patterns for the LED 1302 to provide various alarms or status of the controller 1000 and/or the MCS device 1110.

The controller 1000 further includes a port 1107 that can receive a cable connected to an MCS device. The port 1107 can support multiple versions of the MCS devices. The controller 1000 can also include an RFID reader 1304 on a side of the controller 1000. The RFID reader 1304 can read badges of a sales representative and operate the device according to a particular demo mode. The controller 1000 can include a glass cover 1305 that is tilted as shown in FIG. 13 to improve readability for the user.

Figure 14A:
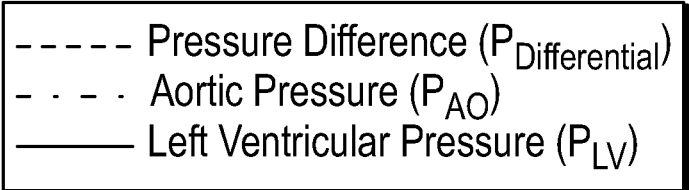
FIG. 14A illustrates a graph showing pressure differences between aortic pressure and left ventricular pressure.
Figure 14A:
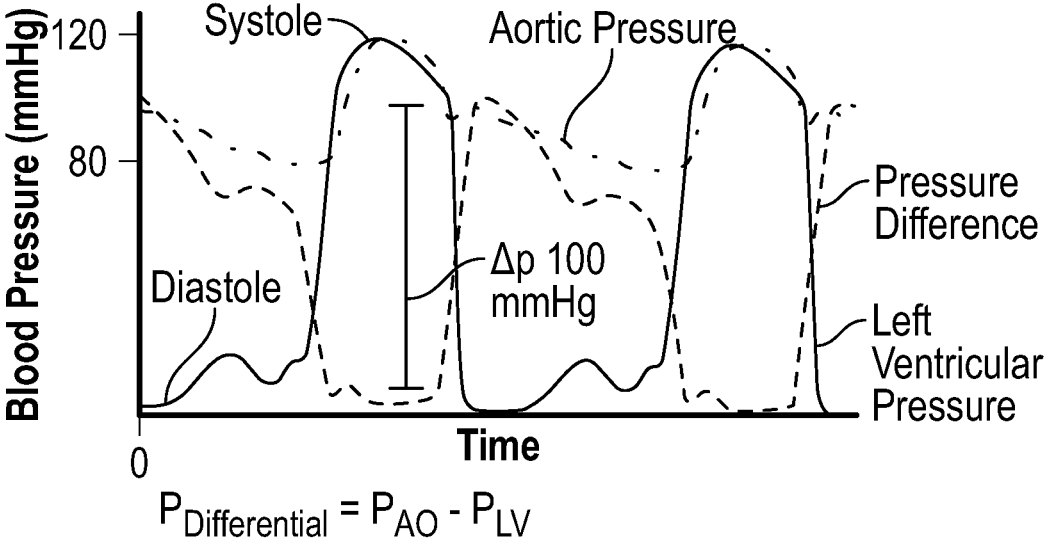

FIG. 14A illustrates a graph showing pressure differences between aortic pressure and left ventricular pressure, which may be typical pressure differences. In some instances, the MCS device 1110 can be positioned between the two locations of the heart corresponding to the different pressure levels (e.g. left ventricle and aortic arch). Therefore, the MCS device 1110 may operate against a pressure difference shown in FIG. 14A. Accordingly, the motor of the MCS device 1110 may in some instances work with the pressure and in other instances against the pressure. Therefore, it was observed that to keep the velocity of the motor, e.g. rotational speed of a motor shaft, constant or approximately stable, the current supplied to the motor would need to change based on the pressure differential.

Figure 14B:
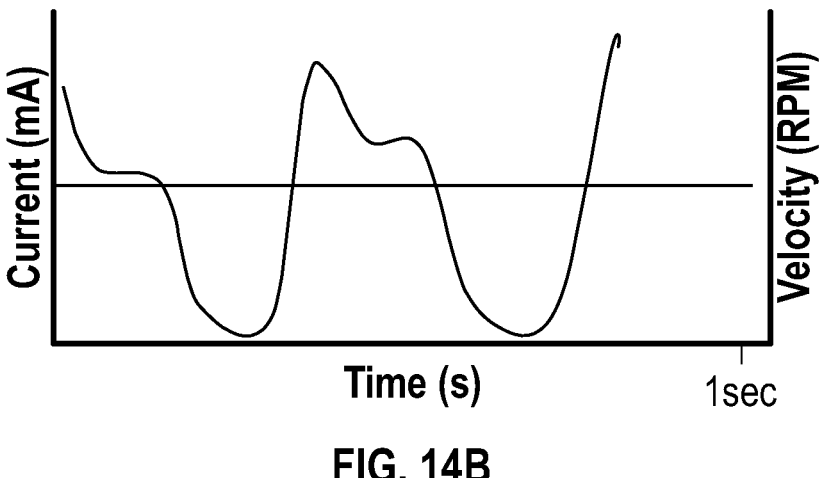
FIG. 14B illustrates a graph showing applied current for a constant rotational speed of a motor shaft.

FIG. 14B shows the applied current for a constant motor velocity. The current curve of FIG. 14B follows a similar behavior as to the pressure differential curve of FIG. 14B. In some embodiments, the control system 1102 can control a motor to run at constant velocity by varying the motor current. The variation in the motor current can be used by the control system 1102 to probe the differential pressure, and therefore physiology of the patient, operating conditions, and machine conditions.

Figure 15:
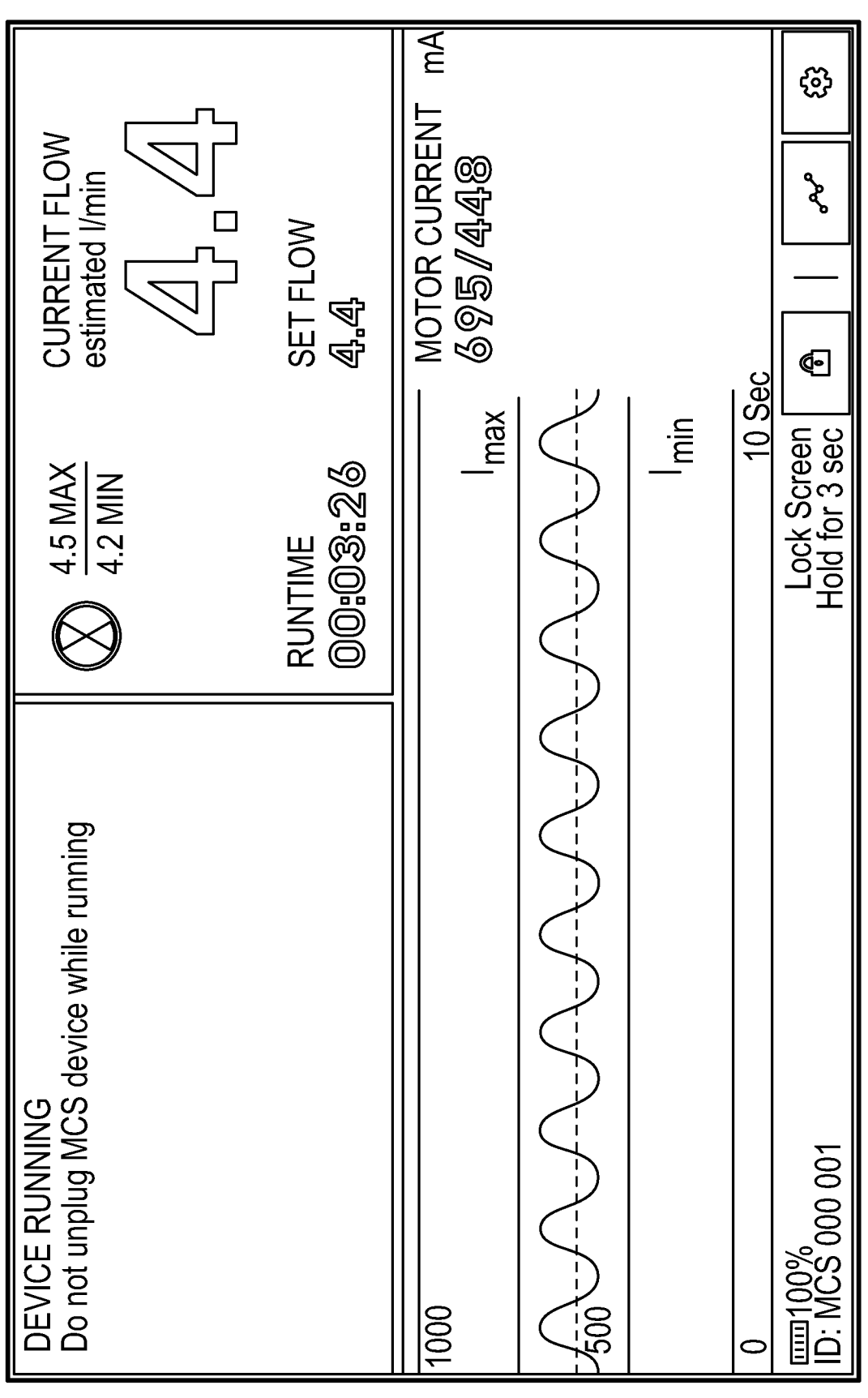
FIG. 15 illustrates an example controller user interface for displaying control parameters.

FIG. 15 illustrates an example user interface that can display flow rate parameters and motor current. The user interface can also display the parameters as a graph plotted with time. The user interface may be shown on the controller 1000, for example on the display.

Figure 16A:
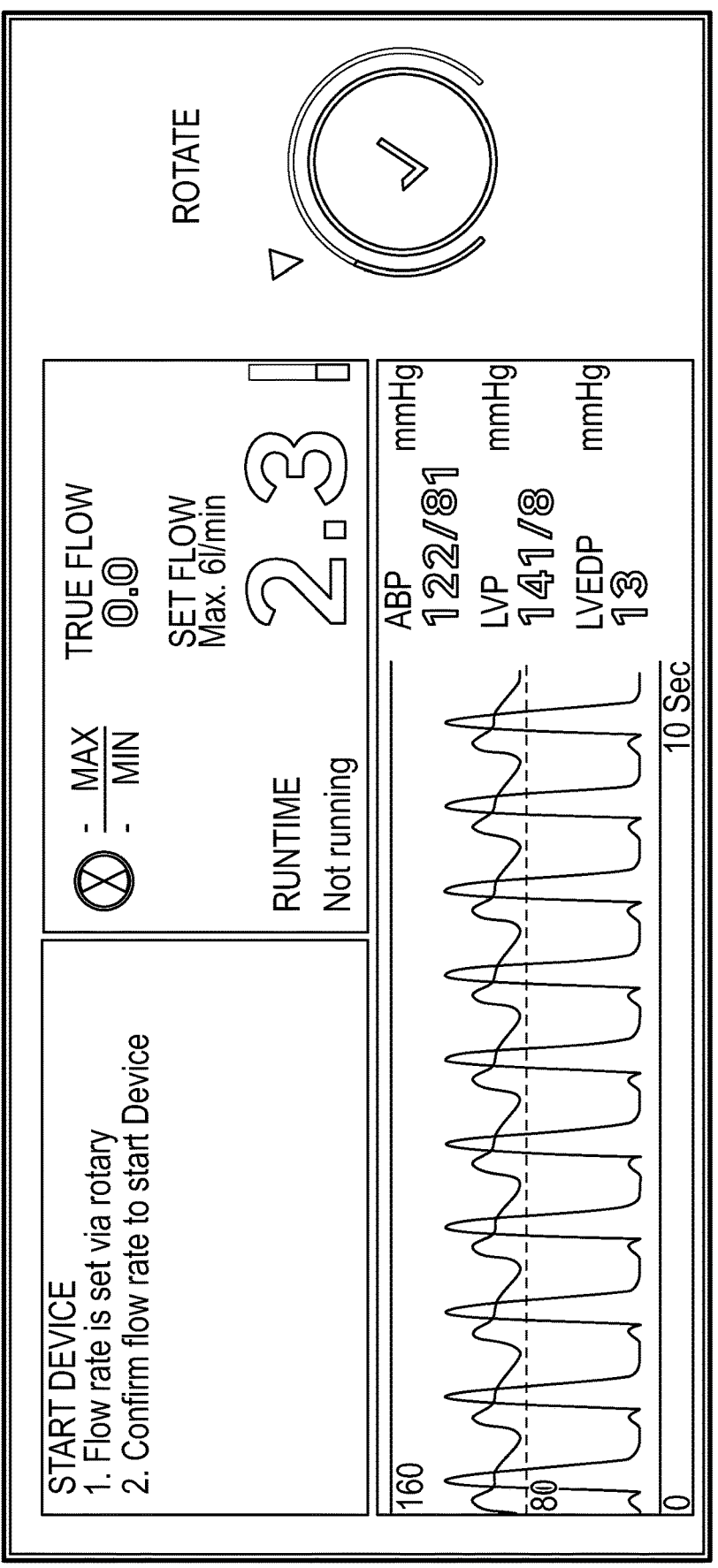
FIG. 16A illustrates an example user interface in a configuration mode.
Figure 16B:
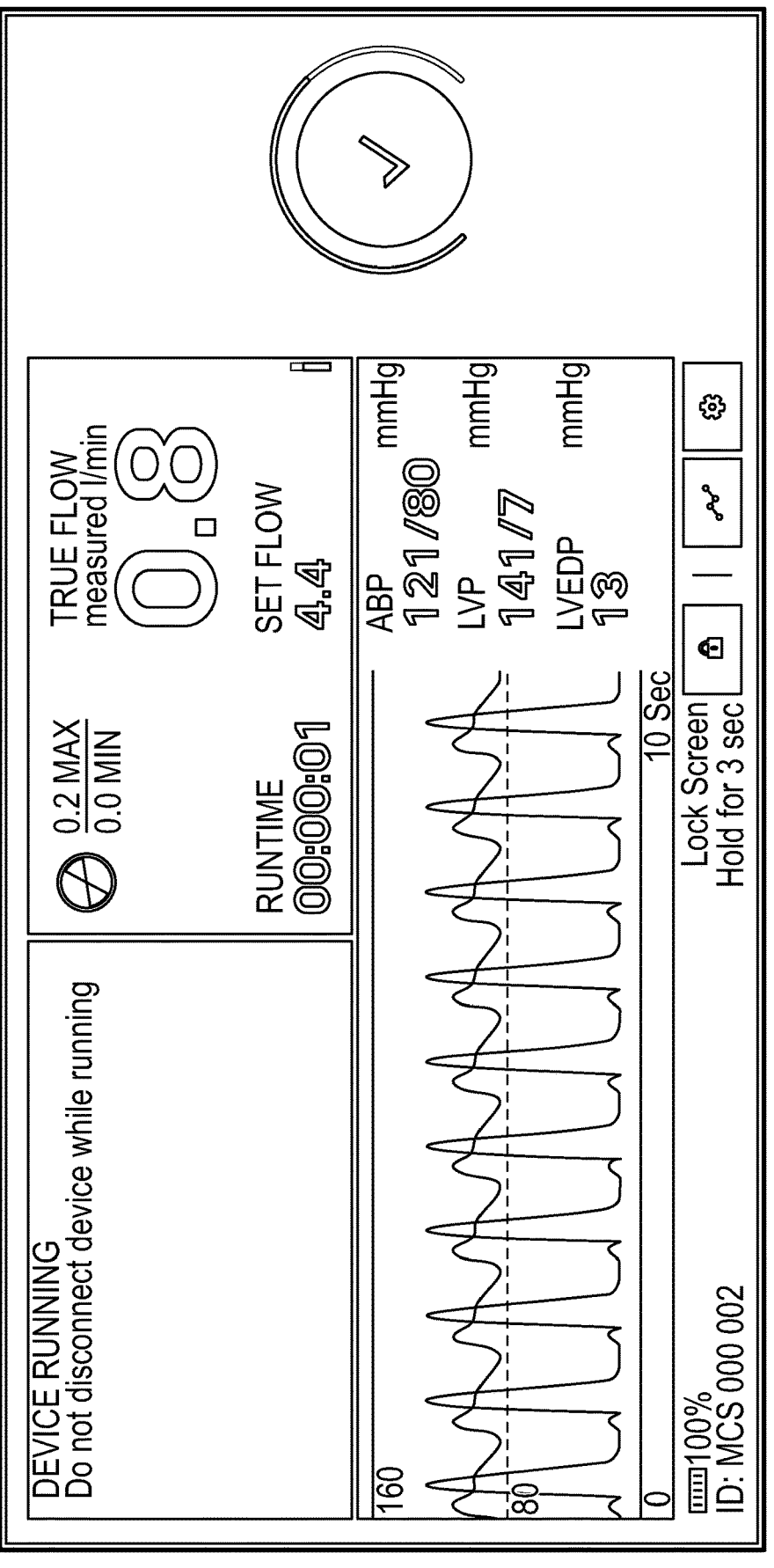
FIG. 16B illustrates an example user interface in an operating mode.

FIG. 16A illustrates an example user interface in a configuration mode where the control element 1008 can be used to modify parameters, such as setting the flow rate. The control element 1008 can include a visual feedback system directly on the knob and/or adjacent to the knob. FIG. 16B shows an example user interface during operation mode. Comparing FIGS. 16A and 16B, certain text on the user interface can be highlighted or emphasized depending on the modes. In the configuration mode, the set flow rate is enlarged. In operational mode, the flow rate is enlarged. This improves readability for the users particularly when the user interface includes several parameters.

In some embodiments, only some of the user interfaces may be available depending on the type of MCS device 1110 connected with the controller. For example, some devices discussed above may not include any sensors and may not support all the user interfaces discussed above. These sensor-less devices may be lower cost and smaller.

Figure 17B:
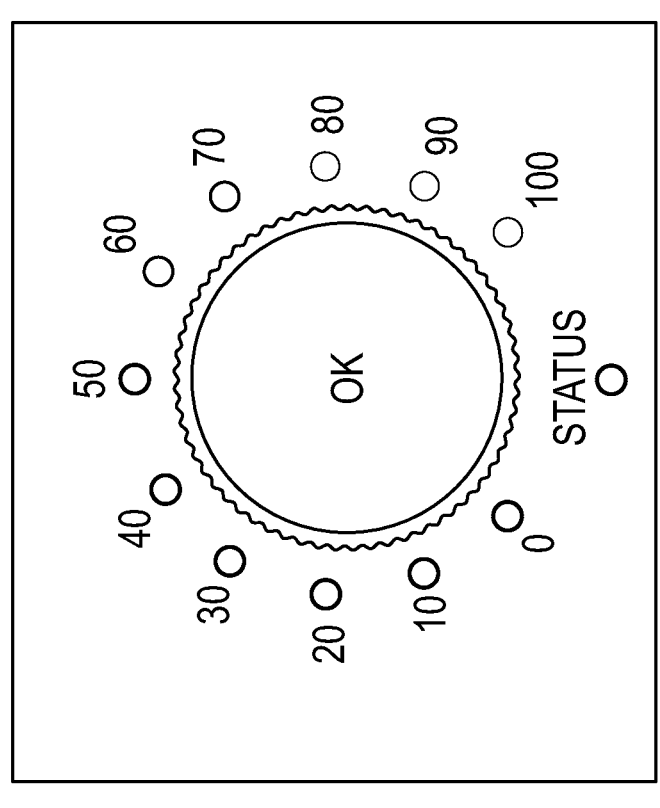
FIGS. 17A and 17B illustrate embodiments of an electronic control element.
Figure 17A:
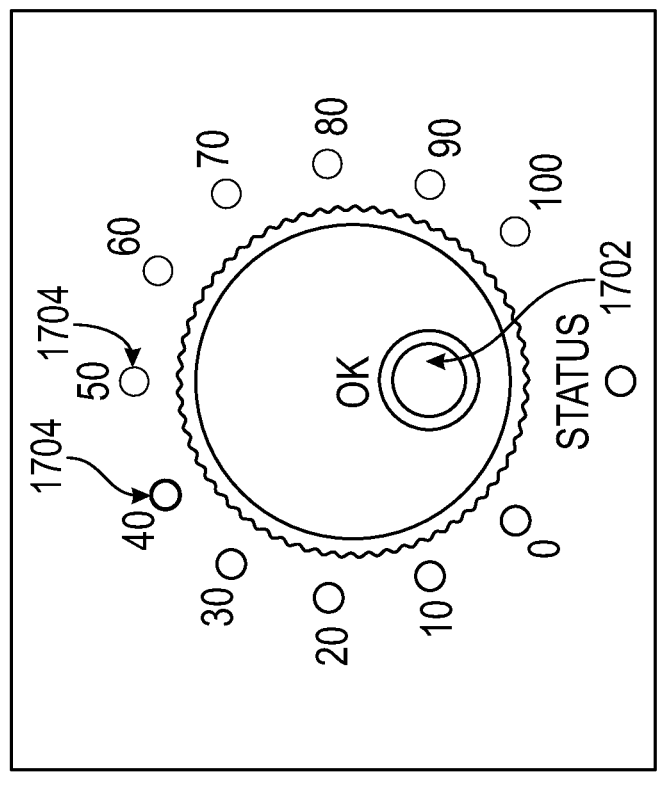

FIG. 17 illustrates an embodiment of an electronic control element 1702 and visual indicators 1704. The electronic control element 1702 can include a display on the face of the dial. Furthermore, the visual indicators 1704 can indicate status of the motor or other operating conditions as the dial is rotated.

Figures 18A, 18B, 18C, 18D:
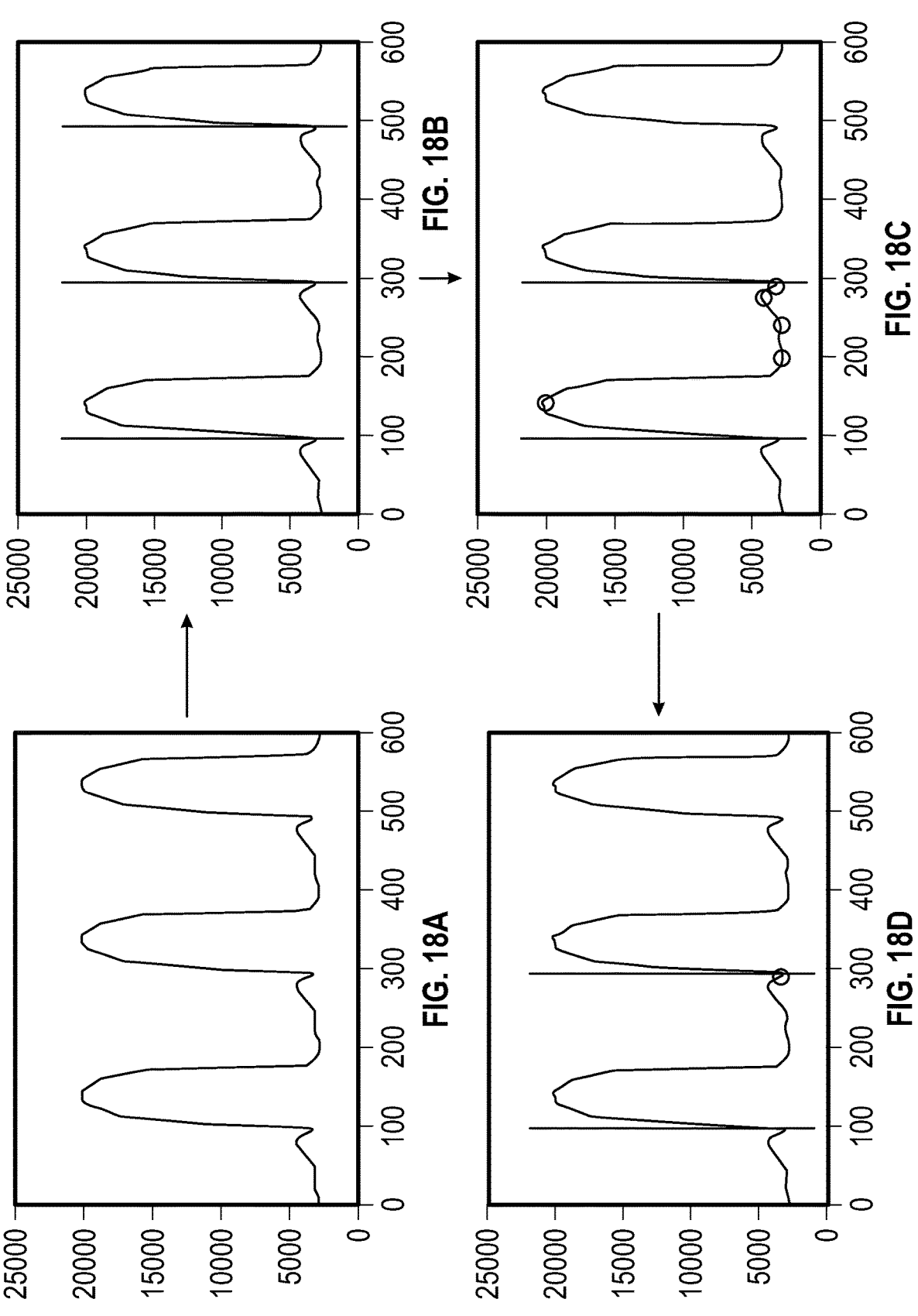
FIGS. 18A to 18D are example left ventricle (LV) pressure curves illustrating a process for determining left ventricular end-diastolic pressure (LVEDP).

FIGS. 18A to 18D are example left ventricle (LV) pressure curves illustrating a process for determining left ventricular end-diastolic pressure (LVEDP). The control system 1102 can document the status and operational parameters, which may be transferred to an EMR system via network communications. The control system 1102 can measure left ventricular end-diastolic pressure (LVEDP). FIGS. 18A to 18D illustrate a series of steps for the determination of LVDEP from the measured LV pressure curve. FIG. 18A illustrates an example LV pressure curve measured with 100 MHz sampling rate. The control system 1102 can process the measured LV pressure curve to determine LVDEP. For example, the control system 1102 can identify a largest positive gradient in the LV curve as illustrated in FIG. 18B. This can identify the pulse value. Other techniques can be used to identify a start of a pulse. Once pulse are identified, the control system 1102 can find maxima and minima in the LV curve between 2 steep positive slopes as illustrated in FIG. 18B. This can also yield systolic and diastolic values. In some instances, the control system 1102 can identify a minimum value left of the $2^{nd}$ slope as illustrated in FIG. 18D. This value can represent the LVEDP determination.

As discussed above, e.g. with respect to FIG. 14B, controlling or synchronizing motor current with heart and measuring the motor current can enable the control system 1102 to probe the differential pressure through measuring current, and therefore physiological processes of the patient, operating conditions, and machine conditions. Physiological processes may include when the pump is hitting the wall of the heart. In some instances, the motor current is kept constant while measuring the change in RPM. In some instances, a separate flow or pressure sensor is not required to probe physiological processes. The motor design including a motor controller, such as the controller 1000, can enable high resolution current measurement. In some instances, a motor controller is sensorless, for example the motor controller may not include a Hall sensor. In some instances, the control system 1102 may operate the motor in a pulsatile mode to improve heart recovery.

Figure 19:
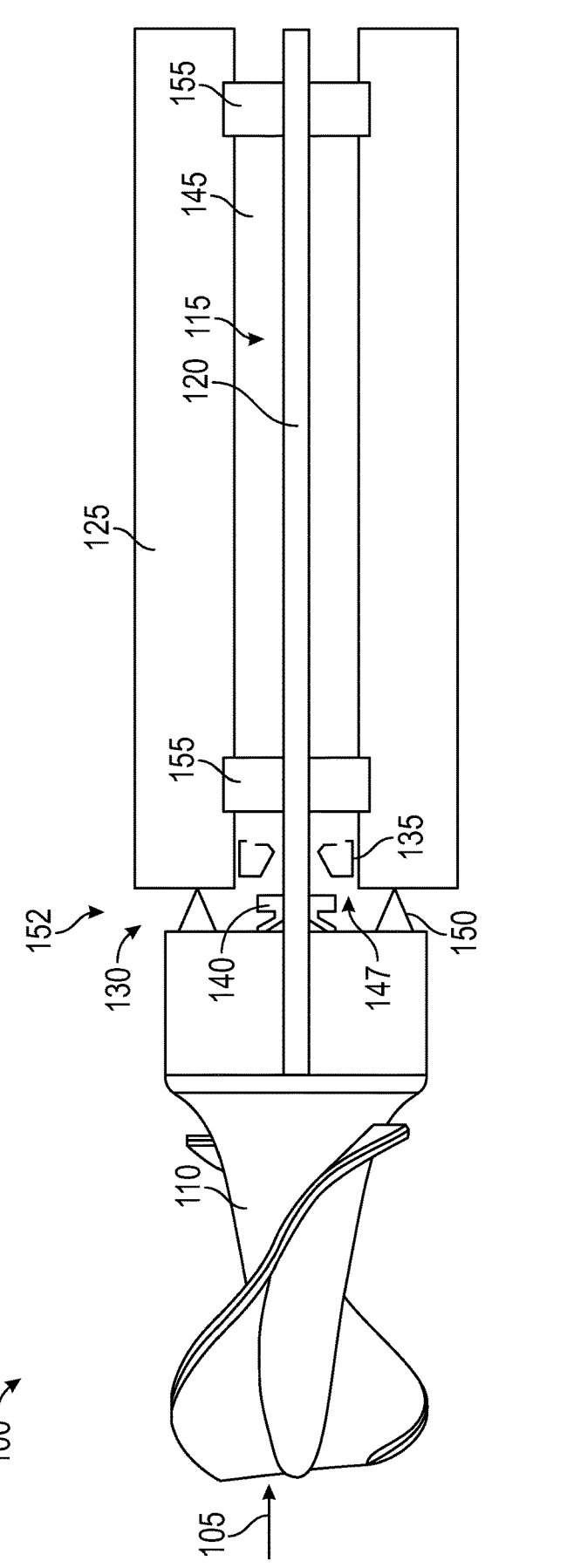
FIG. 19 is a side view of an alternative embodiment of a pump of an MCS system.

FIG. 19 shows a schematic side view of another embodiment of a pump 100 for pumping blood 105. The pump 100 is designed and shaped for use in a fluid channel such as a blood vessel. The pump 100 or features thereof may be used with any of the other pumps or features described herein, such as the pump 22, and vice versa. For example, features of the pump 100 may be used with the pump 22 described above. In some embodiments, the pump 22 include the motor, shaft and seal arrangement of the pump 100, as further described.

The pump 100 may have an impeller 110, a drive device 115 with a shaft 120, a shaft housing 125 and a sealing device 130. The impeller 110 may be designed to pump the blood 105 or other fluid. The drive device 115 with shaft 120 may be designed to drive the impeller 110. The shaft housing 125 may be designed to accommodate the shaft 120 and/or the drive device 115 and is also referred to as the "housing" in the following. The sealing device 130 may comprise at least one casing sealing element 135 and/or one impeller sealing element 140, which is accommodated between the drive device 115 and the impeller 110 and which is designed to prevent fluid 105 from entering the drive device 115 and/or the shaft casing 125 during operation of the pump 100. In some embodiments, the pump 100 may include one or more of the seal features described herein with respect to FIGS. 26A-26C.

According to this embodiment, the impeller 110 may only have an exemplary tapered basic body, which may be rotated around a longitudinal axis during operation of the impeller 110. Radially around the longitudinal axis, the basic body according to this embodiment may have two blades in order to generate a fluid flow or fluid suction in the fluid 105 when the impeller 110 rotates. For this purpose, the blades may be arranged spirally wound around an outer wall of the basic body according. A body of rotation of the impeller 110 may be created by the rotation of one or more so-called "B-spindles". According to an alternative embodiment, the impeller 110 may have a differently shaped, for example cylindrical, basic body and/or a different number of blades or vanes. According to this embodiment, the drive unit 115, which will also be referred to as "drive" in the following, may have a motor 145, for example in the form of an electric motor. According to this embodiment, the motor 145 may be coupled to the shaft 120. The shaft 120 is straight according to this embodiment. The shaft housing 125 may be correspondingly tubular according to this embodiment and accommodate at least the shaft 120 or, according to this embodiment, the entire drive unit 115 with the motor 145 completely. According to an alternative embodiment, the motor 145 may be arranged outside the shaft housing 125. According to this embodiment, the housing sealing element 135 and/or impeller sealing element 140 may be made of a strong but elastic material. In other words, the casing sealing element 135 and/or impeller sealing element 140 may have no liquid or semi-liquid material.

According to this embodiment, the housing sealing element 135 may be attached to an inner side of the shaft housing 125 and/or be arranged around the shaft 120. According to this embodiment, the housing sealing element 135 may be formed as a sealing ring, according to this embodiment as a rotary shaft seal. According to this embodiment, the casing sealing element 135 may be attached to an inlet opening 147 of the shaft casing 125 facing the impeller 110. According to one embodiment, the casing sealing element 135 may be fixed directly to the inlet opening 147.

The additional or alternative impeller sealing element 140 may be attached to the impeller 110 and/or arranged around the shaft 120 and/or the shaft casing 125 in contact according to this embodiment. According to this embodiment, the impeller sealing element 140 may be designed as an additional sealing ring, here an axial shaft seal. The axial shaft seal may also be described as a "V-ring". According to this embodiment, this V-ring may have a V-shaped or plate-shaped flexible sealing lip that extends away from an annular base body of the axial shaft seal. According to this embodiment, the sealing lip may be attached to the impeller 110.

The impeller sealing element 140 may also be preloaded towards the shaft 120 in the mounted state according to this embodiment. A pretension may be caused by a deformation of the impeller sealing element 140. According to an alternative embodiment, the pump 100 may have a spring element which causes the preload.

Furthermore, according to this embodiment, the impeller sealing element 140 may have at least one gap sealing element 150, which may be arranged to fluidically seal a gap 152 between the shaft housing 125 and the impeller 110 in order to prevent the fluid 105 from entering the gap 152. According to this embodiment, the gap sealing element 150 is designed as an additional sealing ring. According to this embodiment, an outer diameter of the gap sealing element 150 is larger than an outer diameter of the impeller sealing element 140. According to this embodiment, the impeller sealing element 140 may be arranged coaxially with respect to the additional sealing ring in a passage opening of the additional sealing ring.

A free end of the shaft 120 is fixed in the impeller 110 according to this embodiment. According to an alternative embodiment, the free end of the shaft 120 and the impeller 110 are connected without contact by means of a magnetic coupling, whereby a driving force of the motor 145 is magnetically transferable to the impeller 110.

The pump 100 also has, according to this embodiment, a bearing device 155 for radial and/or axial bearing of the shaft 120 in the shaft housing 125. For this purpose, the bearing device 155 according to this embodiment may have two bearing elements at two opposite ends of an interior of the shaft housing 125, in which the shaft 120 is, for example, centrally mounted. According to this embodiment, the housing sealing element 135 may be arranged outside a space bounded by the two bearing elements.

The pump 100 presented here may be used and shaped as a blood pump for a cardiac support system. According to one embodiment, the pump 100 may be designed as a ventricular assist device (VAD) pump for short-term implantation with a contacting radial and/or axial seal.

If the pump 100 is used as a temporary/short-time used VAD-pump, it is important that the pump 100 may be implanted very quickly. According to this embodiment, a system as simple as possible is used for this purpose. There may be only one or more sealing elements 135, 140, 150, and liquid or partially liquid media such as flushing media or barrier media may be dispensed, or an external forced flushing for sealing or preventing blood from entering the motor.

According to this embodiment, the pump 100 may have the electric drive in the form of the electric motor 145, the rotating shaft 120, the impeller 110, the bearing device 155, the shaft housing 125 and at least one sealing element 135, 140, 150, which may be firmly connected to the housing 125 according to an embodiment in the form of the housing sealing element 135 and has a sealing function with respect to the rotating shaft 120 and/or the impeller 110. Additionally or alternatively, the pump 100 may have a sealing element in the form of the impeller sealing element 140 and/or gap sealing element 150, which seals the housing 125 against the rotating impeller 110 in the axial direction. According to this embodiment, the impeller 110 may consist of a core with, for example, a hub and at least two or more blades. During operation of the pump 100, the fluid 105 may be fed axially to the impeller 110 (suction) and discharged radially/diagonally through openings in an impeller housing of the impeller 110 not shown here. According to this embodiment, the impeller 110 may be firmly connected to the drive shaft 120 of the motor 145, which provides the required drive power. According to this embodiment, the shaft 120 may be supported by at least one radial and/or at least one axial bearing. Optionally, the bearings may also be realized in combination with a radial-axial bearing. According to one possible embodiment, the housing 125 may have at least one sealing element 135 to the impeller 110. According to another embodiment, this at least one sealing element 140, 150 may be attached to the impeller 110. The seal may be of contact design, where the sealing element 125, 140 is always in contact with the shaft 120 and the casing 125. Furthermore, at least one (further) sealing element 140, which seals the shaft 120 against the casing 125, may be arranged optionally/alternatively. This may be designed according to an embodiment in such a way that the sealing element 140 is preloaded towards the shaft 120. According to one embodiment, this may be realized with a spring or according to another embodiment, it is ensured by shaping the elastic sealing element 140. One possible design of the housing sealing element 135 is a rotary shaft seal. The axial shaft sealing ring may be a possible design of the alternative/optional sealing element 140.

According to one embodiment, the pump 100 may have a maximum outside diameter of less than five millimeters. In another embodiment the pump 100 may have an outside diameter of less than eight millimeters. According to one embodiment, the pump 100 may be designed for a short-term use of less than 24 hours, in another embodiment for a use of less than ten days, in another embodiment for less than 28 days, and in another embodiment for less than or equal to six months.

Figure 20:
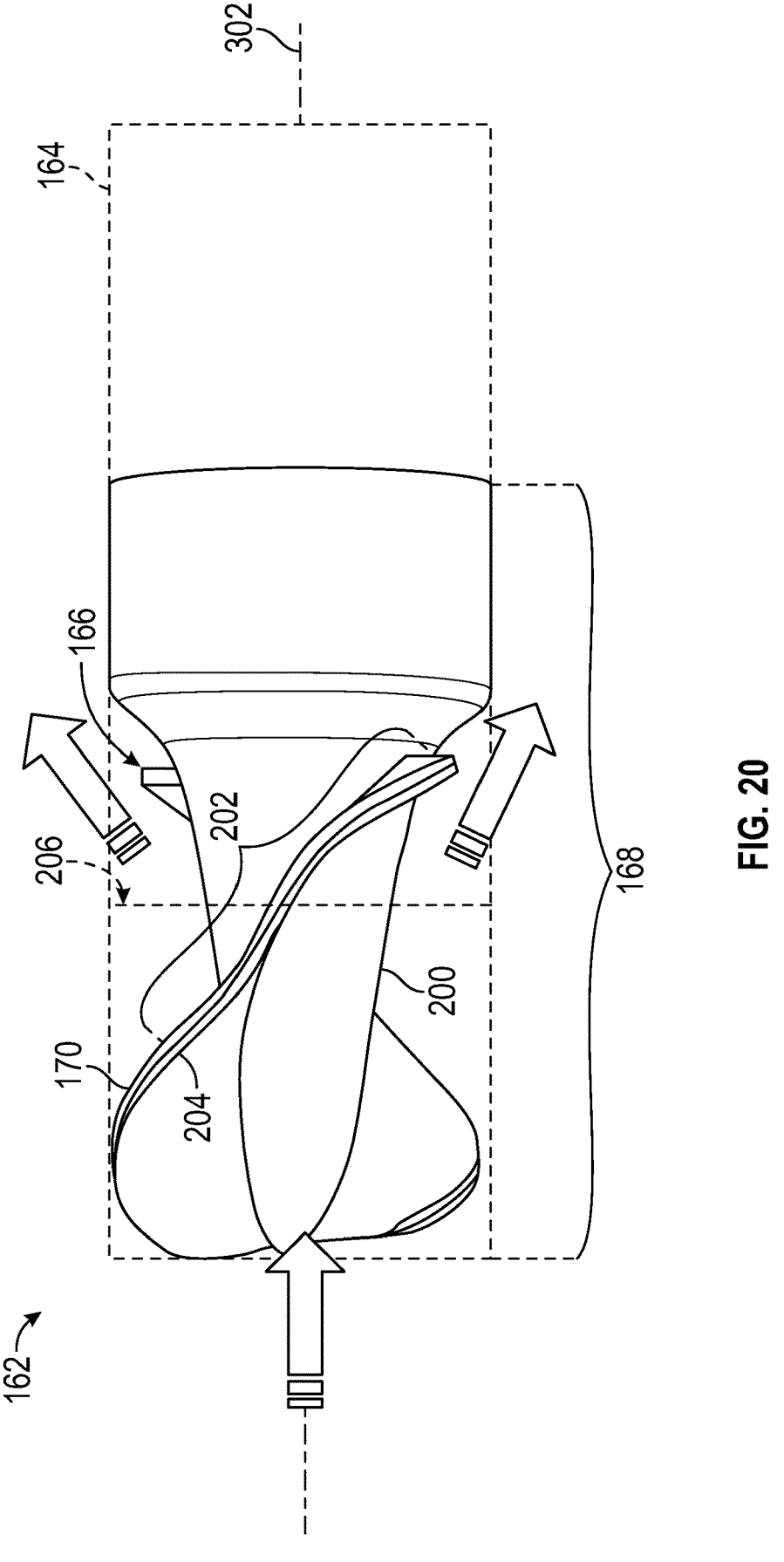
FIG. 20 is a side view of an alternative embodiment of an impeller of an MCS system.

FIG. 20 is a side view of an alternative embodiment of a pump 162 having an alternative embodiment of an impeller 168. The impeller 168 is rotatably mounted within an impeller housing, which may be a proximal end of an inlet tube or a separate housing for the impeller 168. The impeller 168 may face outlet openings 166. The impeller 168 provides for axial suction and radial or diagonal discharges of the blood via the outlet openings 166. The pump 162 may rotate about an axis of rotation 302. A motor inside the sealed motor housing 164 may rotate the impeller 168.

The impeller 168 may include at least one helically wound blade 170. The blade 170 may ensure the efficient and gentle transport of blood. As shown in FIG. 20, the blade 170 may be helically wound around a hub 200 of the pump 162. The hub 200 may form an inner core of the impeller 168. A flow direction of the blood flow path is indicated by three arrows. The blood is aspirated by a pump inlet that acts as an intake opening upstream of the impeller 168 and exits out the outlet openings 166.

A skeleton line 204 of the blade 170 may have a point of inflection in a region of the upstream start of outlet openings 166. The blade 170 may extend from an upstream end of the impeller 168 over an entire length or at least over a major part of the hub 200. The hub 200 may have a diameter that increases in the direction of flow, so that the shape of the hub 200 thickens along the direction of flow. This shape of the hub 200 may facilitate a radial or diagonal discharge of the blood.

The blade 170 may include a vane section 202 having a wave-shaped vane curvature, which is defined by multiple curved portions of the skeleton line 204 of the blade 170. As discussed herein, a wave-shaped curvature of the blade can refer to a change in curvature of the blade section 202 associated with at least one sign change, for example positive or negative concavity/convexity. At least one section of the blade 170 and/or the entire vane section 202, or one portion of the vane section 202, may be located radially inwardly of the outlet openings 166. The vane section 202 may be at least partially in the region of a flow-facing edge 206 of the outlet opening 166. The blade section 202 may represent one or more transitions between a convex and a concave curvature.

In certain embodiments, the impeller 168 may comprises two blades 170, which are wound in the same direction around the hub 200. Each blade 170 may have a vane section 202. In alternative embodiments, the impeller 108 includes more than two blade elements 170, such as three, four, five, six or more. The pump 162, or other pumps described herein, may have additional features or modifications, such as those described in PCT Publication No. WO 2019/229223, filed May 30, 2019, titled AXIAL-FLOW PUMP FOR A VENTRICULAR ASSIST DEVICE AND METHOD FOR PRODUCING AN AXIAL-FLOW PUMP FOR A VENTRICU-LAR ASSIST DEVICE, and/or described in U.S. patent application Ser. No. 17/057,252, filed Jun. 18, 2021, titled AXIAL-FLOW PUMP FOR A VENTRICULAR ASSIST DEVICE AND METHOD FOR PRODUCING AN AXIAL-FLOW PUMP FOR A VENTRICULAR ASSIST DEVICE, the disclosures of each of which is hereby incorporated by reference herein in its entirety for all purposes and forms a part of this specification.

Figures 21, 22:
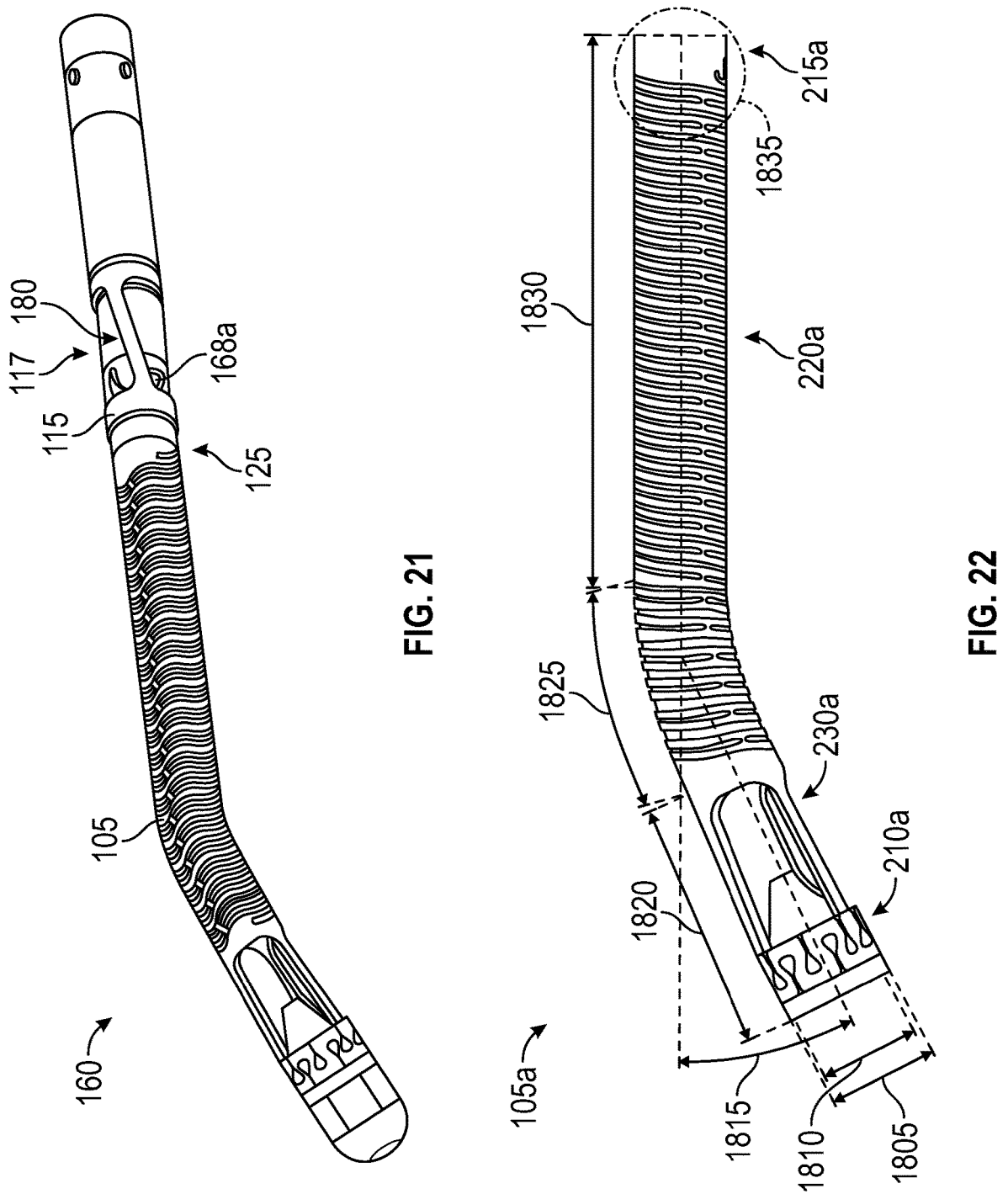
FIG. 21 is a perspective view of an alternative embodiment of a pump region of an MCS system.
FIG. 22 is a side view of an alternative embodiment of an inlet tube of an MCS system.

FIG. 21 is a perspective view of an alternative embodiment of a pump region 160 of an MCS system. The pump region 160 may include a pump 117 having an alternative embodiment of an impeller housing 115. The pump region 160 or features thereof may be used with any of the MCS systems or pumps described herein. The pump region 160 may be arranged in a minimally invasive manner through a transfemoral or transaortic catheter in an aorta and/or at least partially in a ventricle. As described herein, the pump region 160 may include a blood pump for the MCS system. A maximum external diameter of the pump region 160 may be less than ten millimeters (mm) (e.g., less than or equal to 7 mm, or less than or equal to 5 mm). The pump region 160 may include a pump 117. The pump 117 may have an axial design including an impeller 168a against which axial flow occurs. The axial design of the pump may facilitate the pump region 160 having a maximum external diameter of less than 10 mm.

Blood flows during the operation of the pump device 160 through an inlet tube 105 and is expelled through outlet openings 180 within a circumference of the impeller housing 115 of the pump 117 in order to be pumped into the ascending aorta. The impeller 168a may be completely enclosed in a first section in or near the impeller housing 115, which is in the form of a cylindrical impeller housing, and is interrupted in a second section by the outlet openings 180 in the impeller housing 115. A transition between these two sections is characterized by a beginning 125 of the outlet openings 180. The pump 160, or other pumps described herein, may have additional features or modifications, such as those described in PCT Publication No. WO 2019/229214, filed May 30, 2019, titled PUMP HOUSING DEVICE, METHOD FOR PRODUCING A PUMP HOUSING DEVICE, AND PUMP HAVING A PUMP HOUSING DEVICE, and/or described in U.S. patent application Ser. No. 17/057,548, filed May 19, 2021, titled PUMP HOUSING DEVICE, METHOD FOR PRODUCING A PUMP HOUSING DEVICE, AND PUMP HAVING A PUMP HOUSING DEVICE, the disclosures of each of which is hereby incorporated by reference herein in its entirety for all purposes and forms a part of this specification.

FIG. 22 is a side view of an alternative embodiment of an inlet tube 105a of an MCS system. The inlet tube 105a may be used with any of the MCS systems or pumps described herein. The inlet tube 105a includes a first connection section 210a that may connect the inlet tube 105a to a distal tip. The inlet tube 105a also includes a second connection section 215a that may connect the inlet tube 105a to a pump outlet or impeller housing. The inlet tube 105a also includes a structural section 220a extending between the second connection section 215a and the first connection section 210a. In some embodiments, the structural section 220a may extend between a pump inlet 230a and the first connection section 210a.

In some embodiments, the structural section 220a can include one or more stiffening recesses that can change the rigidity of the inlet tube 105a. The stiffening recesses may extend over part of the structural section 220a or over the entire structural section 220a. The stiffening recesses may be arranged in a helical circumferential manner. The stiffening recesses may be in the form of slots.

FIG. 22 further includes geometric reference markings for illustrating exemplary dimensions of the inlet tube 105a. At the first connection section 210a, the inlet tube 105a may have an inner diameter of 6.5 millimeters (or between 4.5 to 8.5 millimeters) shown by the marking 1805. The outer diameter shown in this area by the mark 1810 is 7 millimeters (or between 5 mm to 9 mm). The angle of the bend indicated by the marking 1815 is 26 degrees (or between 16 degrees to 36 degrees). The marking 1820 shows a length of 15 millimeters (or between 10 millimeters and 20 millimeters) of a region of the inlet tube 105a that includes the first connection section 210a and the pump inlet 230a, as well as a region of the structural section 220a with the recess closest to the pump inlet 230a. In some embodiments, the first connection section 210a is part of the pump inlet 230a. An adjacent bent portion of the structural section 220a, which is inclined with respect to the longitudinal axis of the inlet tube 105a, has a length of 14 millimeters, as shown by the mark 1825. The adjacent portion of the inlet tube 105a shown by the mark 1830 includes a remainder of the structural section 220a and the second connection section 215a. The inlet tube 105a, or any other inlet tube described herein, may have additional features or modifications, such as those described in PCT Publication No. WO 2019/229210, filed May 30, 2019, titled LINE DEVICE FOR CONDUCTING A BLOOD FLOW FOR A HEART SUPPORT SYSTEM, AND PRODUCTION AND ASSEMBLY METHOD, and/or described in U.S. patent application Ser. No. 17/057,355, filed May 18, 2021, titled LINE DEVICE FOR CONDUCTING A BLOOD FLOW FOR A HEART SUPPORT SYSTEM, AND PRODUCTION AND ASSEMBLY METHOD, the disclosures of each of which is hereby incorporated by reference herein in its entirety for all purposes and forms a part of this specification.

Figure 23:
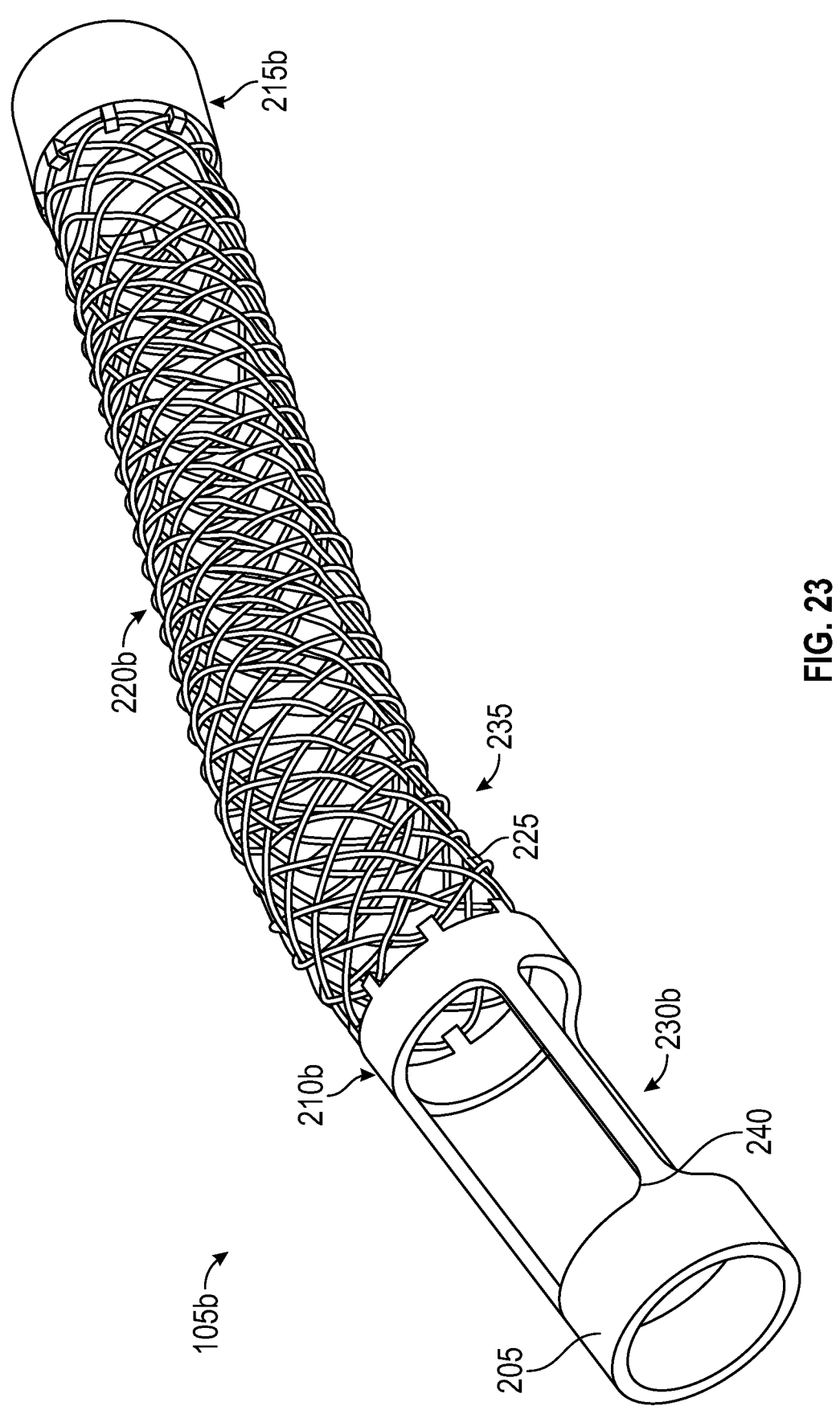
FIG. 23 is a perspective view of an alternative embodiment of an inlet tube of an MCS system.

FIG. 23 is a perspective view of an alternative embodiment of an inlet tube 105b of an MCS system. The inlet tube 105b may be used with any of the pumps or MCS systems described herein. The inlet tube 105 may be in the form of a braided suction hose. The inlet tube 105b has a main body 205. The main body 205 may have at a first end a first connection section 210b for connecting the inlet tube 105b to a distal tip and at a second end a second connection section 215b for connecting the inlet tube 105b to a pump outlet or impeller housing. The main body 205 may have a pump inlet 230b arranged in the first connection section 210b for introducing the blood flow into the base body 205. The inlet tube 105b may be shaped to be connectable to adjacent components of the circulatory support system. The pump inlet 230b may have at least one inlet opening 240 cut out or formed in the first connection section 210b. The inlet opening 240 may be implemented as a multi-part window. The pump inlet 230b may comprise three rectangular-shaped inlet openings 240, which may be rounded off in the direction of the braid section 220b in the form of an arc of a circle.

The main body 205 may have a braid section 220b between the connection sections 210b and 215b. The braid section 220b may have a braid structure 235 formed from at least one braided wire 225. The braid structure 235 may be shaped as a diamond lattice. For this purpose, the at least one braided wire 225 may be braided as a lattice and have a plurality of diamond meshes which form the braided structure 235. The inlet tube 105b is shown with a braided flow channel in the braid section 220b. In some embodiments, at least the braid section 220b may be formed from a shape memory material. In some embodiments, the inlet tube 105b may be completely formed from nitinol. By using nitinol, the inlet tube 105b may be not only suitable for short-term use, but also for a service life of over ten years. Nitinol may combine the advantages of biocompatibility and the shape memory property, which makes it possible to implement complex structures in a small installation space, as in the braid section 220.

The braid section 220b may be perforated at the connection sections 210b and 215b. For this purpose, the connection sections 210b and 215b may have a fastening element for threading in a section of the braided wire 225. Additionally or alternatively, the braid section 220b may be glued or soldered to the connection sections 210b and 215b.

The braid section 220b may extend over at least half of the inlet tube 105b in order to adjust the rigidity of the inlet tube 105b. The inlet tube 105b is shaped to enable transfemoral surgery (access via the groin). The inlet tube 105b may thus be flexible enough to be able to be pushed through the aortic arch, and also has a rigidity so that it can be pushed through the blood vessels in the axial direction without kinking. The relevant requirements for flexibility and rigidity of the inlet tube 105 are set by means of the shaping of the braid section 220. The design of the braid structure can determine the ratio of flexibility and rigidity. Variables affecting the ratio of flexibility and rigidity include the number of wire tracks of the at least one braided wire 225, a stiffness and a material thickness of the at least one braided wire 225, and the braid pattern of the braid structure 235.

The higher the number of wire tracks of the at least one braided wire 225, the more rigid the braid structure 235 is. The braid wire 225 comprises, for example, 12 to 24 wire tracks. The larger the wire diameter of the braided wire 225, the stiffer the braided structure 235 is. The wire diameter is between 0.1 millimeter and 0.3 millimeter, for example. In addition, the material properties of the braided wire 225 are important: the higher the modulus of elasticity of the braided wire 225, the more rigid the braid structure 235 is. The braid wire 225 has an elasticity between 74 GPa and 83 GPa, for example. The type of braid of the braid structure 235 is also significant: the closer-meshed the braid, the stiffer it is.

In the embodiment shown in FIG. 23, the inlet tube 105b may be bent in the direction of the first connection section 210b, the bend being shaped, for example, as an obtuse angle with respect to a longitudinal axis of the inlet tube 105b. The bend can be realized by heat treatment of the nitinol braid section 220b. Due to the shape-memory properties of the nitinol, the inlet tube 105b can be formed with a curve shape of the braid section 220b corresponding to the human anatomy in order to enable the inlet opening of the pump inlet 230b of the first connection section 210b to be positioned in the center of the heart chamber. The inlet tube 105b, or any other inlet tube described herein, may have additional features or modifications, such as those described in PCT Publication No. WO 2019/229211, filed May 30, 2019, titled LINE DEVICE FOR CONDUCTING A BLOOD FLOW FOR A HEART SUPPORT SYSTEM, HEART SUPPORT SYSTEM, AND METHOD FOR PRODUCING A LINE DEVICE, and/or described in U.S. patent application Ser. No. 17/057,411, filed Jun. 1, 2021, titled LINE DEVICE FOR CONDUCTING A BLOOD FLOW FOR A HEART SUPPORT SYSTEM, HEART SUPPORT SYSTEM, AND METHOD FOR PRODUCING A LINE DEVICE, the entire contents of each of which is hereby incorporated by reference herein in its entirety for all purposes and forms a part of this specification.

Figure 24:
FIG. 24 is a perspective view of an alternative embodiment of a pump region of an MCS system.

FIG. 24 is a perspective view of an alternative embodiment of a pump region 160a of an MCS system. The pump regions 160a or features thereof may be used with any pump region or MCS system described herein. The pump region 160*a* has an inlet tube 105*c*. The elongated, axial design of the pump region 160, shown with an essentially constant outer diameter, enables transfemoral or transaortic implantation of the pump region 160*a* for placement by means of a catheter in a blood vessel, for example the aorta.

According to the shape for the aortic valve position, the inlet tube 105*c* may have, for example, an incline or curvature of the longitudinal axis and thus a slightly curved shape. In addition to the inlet tube 105*c*, the pump region 160*a* may include a pump or pump unit 186. The pump region 160*a* may also include a distal tip 185, a housing section 188, and/or an anchoring frame 187. The inlet tube 105*c* may be arranged between the distal tip 185 and the pump unit 186. The pump unit 186 may be connected at an end remote from the inlet tube 105*c* to the housing section 188 to which the anchoring frame 187 is attached.

The inlet tube 105*c* may be designed to guide fluid flow to the pump unit 186 of the pump region 160*a*. The inlet tube 105*c* may comprise a pump inlet 130 and a contour section 135. The pump inlet 130 may have at least one inlet opening 140 for introducing the fluid flow into the inlet tube 105*c*. The contour section 135 may be arranged adjacent to the pump inlet 130. In some embodiments, a length of the contour section 135 corresponds to a radius of the inlet tube 105*c* within a tolerance range. The tolerance range may be a deviation of a maximum of twenty percent from the radius of the inlet tube. The contour section 135 may have an inner surface contour. In the flow direction, the inside diameter of the contour section 135 at a first axial position may be greater than the inside diameter at a second axial position. The inner surface contour may have a rounding to reduce the inner diameter at the second axial position. At least one inlet edge of the inlet opening 140 of the pump inlet 130 may be rounded. The inlet opening 140 may be designed, for example, as a window-shaped inlet opening cut into or formed within the pump inlet 130. Further details of an example inner surface contour that may be implemented are shown in, and described with respect to, FIG. 25.

In FIG. 24, the pump inlet 130 and the contour section 135 are shown marked for reference by way of example. In particular, the contour section 135 may be a smaller or larger portion of the inlet tube 105*c* than shown in FIG. 24. When implanted, the pump inlet 130 and the contour section 135 are arranged in the left ventricle. Another section of the inlet tube 105*c* may be led through the aortic valve, and a section of the pump region 160*a* with the pump unit 186 is arranged in a section of the aorta or ascending aorta. A pump outlet 145 in the area of the pump unit 186 guides the fluid flow conveyed through the inlet tube 105*c* into the aorta. The marking 150 shows, by way of example, a position of a heart valve, for example the aortic valve, through which the inlet tube 105*c* is passed in order to position the pump region 160*a*.

A circulatory support system that is limited in terms of installation space, such as a circulatory support system having the pump region 160*a* shown here by way of example, which can be implanted in a minimally invasive manner, has a comparatively low power consumption at a certain pump efficiency. The efficiency is limited by the friction in the pump of the pump unit 186. The pressure loss or the friction in the inlet tube 105*c* when the fluid flow is directed from the inlet opening 140 of the pump inlet 130 in the heart chamber to the pump unit 186 can be affected by the shape of the inlet tube 105*c*. For this purpose, the inlet edges of the inlet opening 140 may be rounded in order to reduce the pressure loss. This alone may not prevent the flow separation. The flow separation is suppressed and thus the pressure loss is reduced by an inlet inner surface contour formed according to the approach presented here in the form of the contour section 135.

Figure 25:
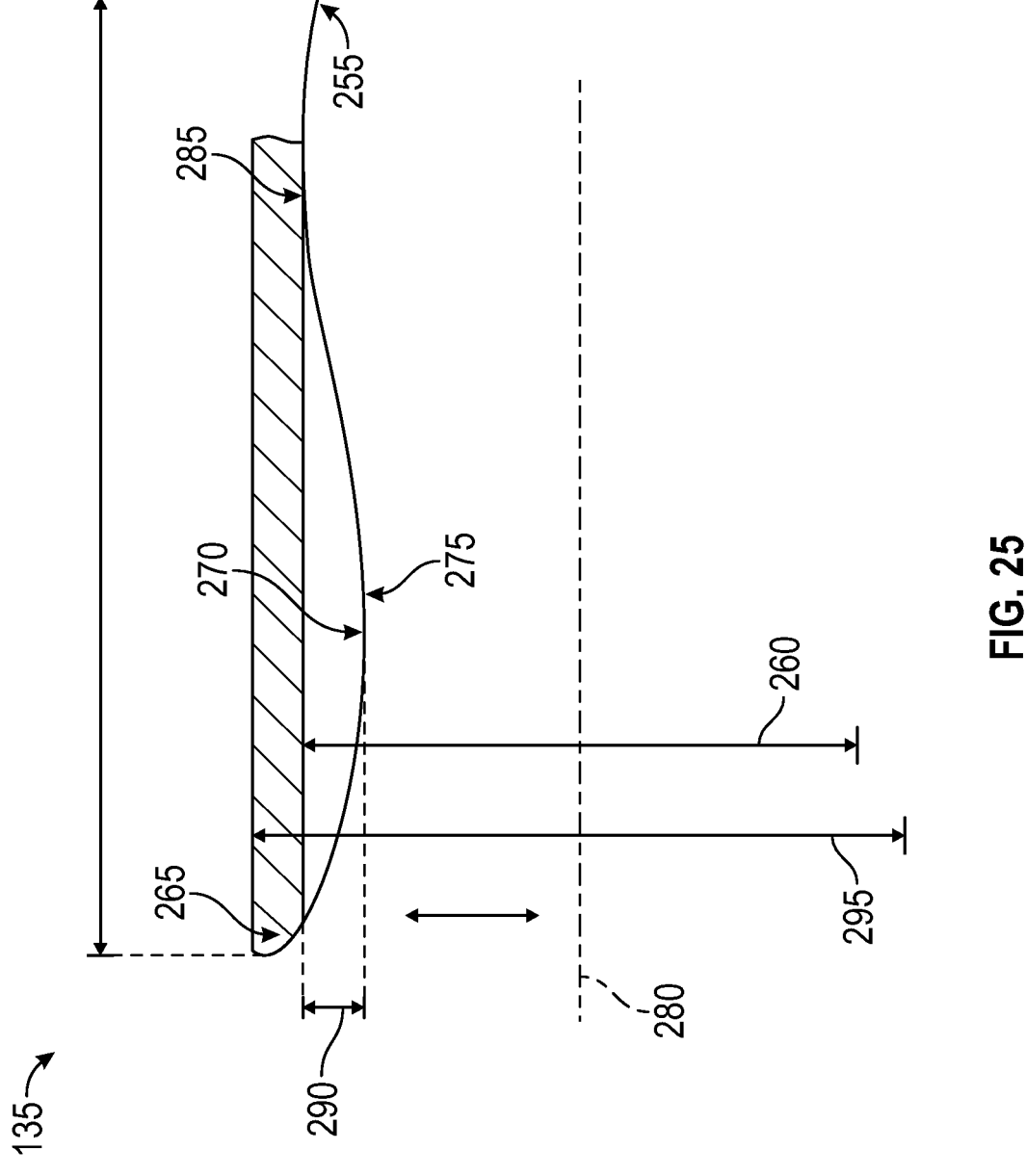
FIG. 25 is a partial cross sectional view of a contour section of an inlet tube of the pump region of FIG. 24.

FIG. 25 is a partial cross sectional view of a contour section 135 of an inlet tube of the pump region 160*a*. Exemplary geometric reference dimensional relationships of the contour section 135 and the inner surface contour 255 are indicated in the figure. An axial section of one half of the contour section 135 is shown. The inner diameter 260 of the contour section 135 is larger at a first axial position 265 than the inner diameter 260 at a second axial position 270. The inner surface contour 255 may have a rounding 275 in the form of an axially arcuate inner wall profile in order to reduce the inner diameter 260 at the second position 270. The first position 265 may mark a point of the contour section 135 along a longitudinal axis of the contour section 135, and the second position 270 may mark a further point of the contour section 135 along the longitudinal axis. The second position 270 may be downstream of the first position 265. In the exemplary embodiment shown here, the longitudinal axis corresponds to an axis of rotation 280 of the contour section 135.

The first position 265 may be arranged in the contour section 135 between the pump inlet and the second position 270. With regard to a flow direction of the fluid flow introduced through the pump inlet, which is directed in the direction of the pump unit through the inlet tube and thus through the contour section 135, the first position 265 is arranged upstream of the second position 270. In addition, the inner diameter of the contour section 135 at a third position 285 is greater than the inner diameter at the second position 270. The third position 285 is downstream of the first and second positions 265, 270.

An inner radius of the contour section 135 at the second position 270 may be at most one fifth smaller than the inner radius at the first position 265. This is shown by the marking 290, which marks a fifth of the inner radius. Correspondingly, the rounding 275 of the inner surface contour 255 may be designed at most as a convex bulge in the region of one fifth of the inner radius, which the marking 290 additionally illustrates.

In some embodiments, the inner surface contour 255 may be designed to be rotationally symmetrical. A part of the contour section 135, which is opposite the part of the inner surface contour 255 shown in FIG. 25 in relation to the axis of rotation 280, accordingly has a rotation of the inside surface contour 255 which may be symmetrical. By means of the formation of the contour section 135 and the inner surface contour 255 shown in FIG. 25, it is possible to reduce or suppress flow detachments of the fluid flow in the inlet tube, which would otherwise form downstream of the inlet edges. In this case, an outer diameter 295 of the contour section 135 may remain constant, and there is advantageously no increase in the installation space of the inlet line or tube. The pressure loss of fluid flow can be reduced by means of the contour section 135 with the inner surface contour 255. The inlet flow and thus the flow behavior of the fluid flow are only directed locally through the contour section 135.

The contour section 135 may have a length which in some embodiments corresponds to a maximum of twice the inner diameter of the inlet tube. Due to the shape of the contour section 135, the pressure loss of the fluid flow may be lower further downstream than in an inlet tube with a constant inner diameter without an inner surface contour, since a suppression or reduction of the separation results in less turbulence downstream. The inner surface contour 255 is shaped in such a way that the flow separation is largely suppressed over a length of up to four times the radius of the inlet tube. The local outside diameter 295 of the inlet tube is limited by a prescribed wall thickness. Adjacent to the inlet opening of the pump inlet, the inlet edge may be rounded convexly in order to reduce the flow separation. An optimization of the shape of the inner surface contour 255, such as the shape shown in FIG. 25, is optionally rotationally symmetrical or, alternatively, independent of the angle of rotation.

In the embodiment of FIG. 25, an optimization of the contour profile of the inner surface contour 255 may form two concave sections and one convex section, regardless of the described inlet edge rounding, with a constant wall thickness, as shown in FIG. 25 with reference to the first position 265, the second position 270, the third position 285, and rounding 275. To this end, the inner wall contour may be optionally shaped in such a way that locally an inner wall radius of up to four fifths based on the inner wall radius is achieved with a constant wall thickness of the contour section 135. The inlet tube 160a or any other inlet tube described herein may have additional features or modifications, such as those described in PCT Publication No. WO 2020/016438, filed Jul. 19, 2019, titled FEED LINE FOR A PUMP UNIT OF A CARDIAC ASSISTANCE SYSTEM, CARDIAC ASSISTANCE SYSTEM AND METHOD FOR PRODUCING A FEED LINE FOR A PUMP UNIT OF A CARDIAC ASSISTANCE SYSTEM, and/or described in U.S. patent application Ser. No. 17/261,335, field Jul. 19, 2021, titled FEED LINE FOR A PUMP UNIT OF A CARDIAC ASSISTANCE SYSTEM, CARDIAC ASSISTANCE SYSTEM AND METHOD FOR PRODUCING A FEED LINE FOR A PUMP UNIT OF A CARDIAC ASSISTANCE SYSTEM, the entire contents of each of which is hereby incorporated by reference herein in its entirety for all purposes and forms a part of this specification.

Figure 26A:
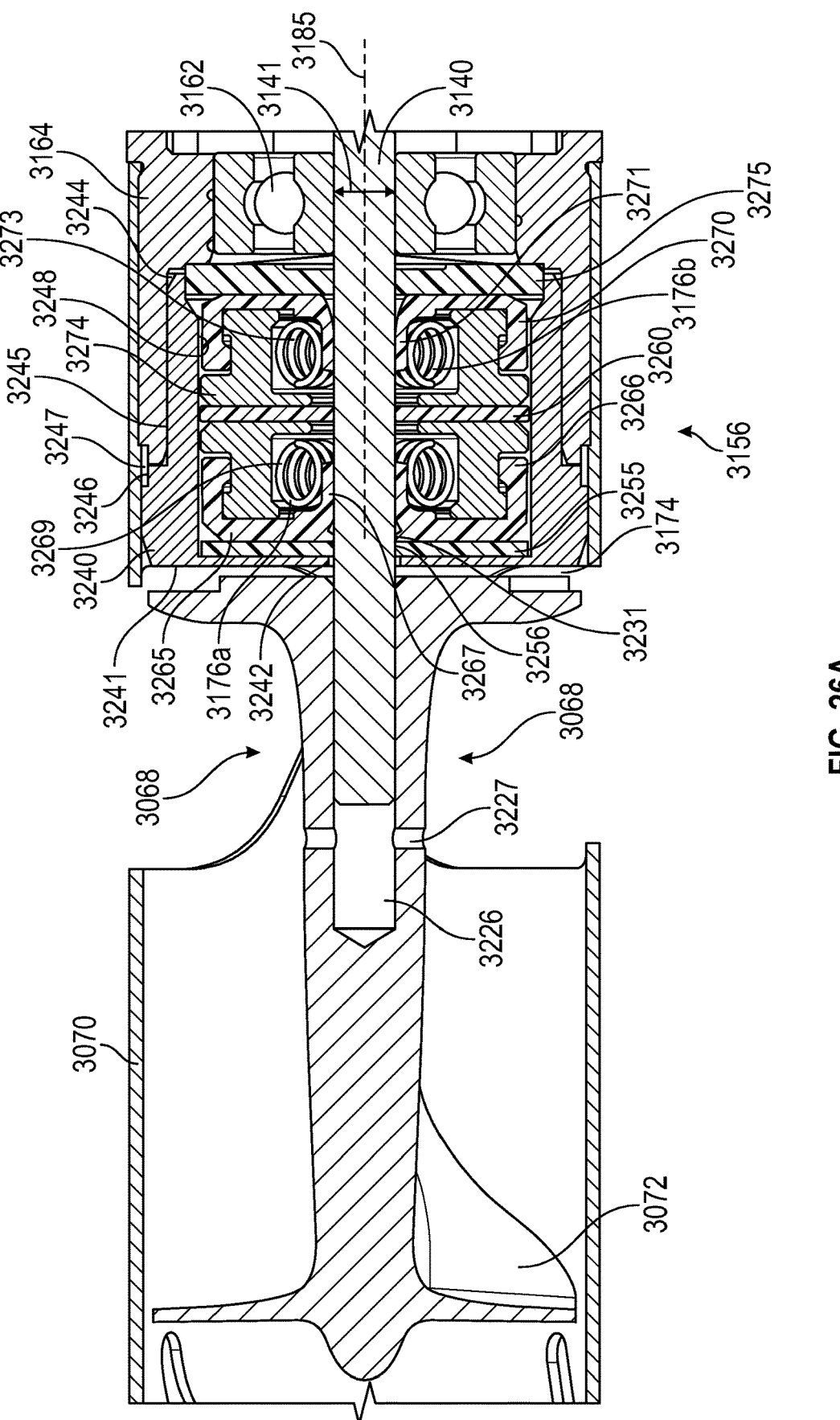
FIGS. 26A-26C are various views of another embodiment of an MCS device having two lip seals facing one another.
Figure 26B:
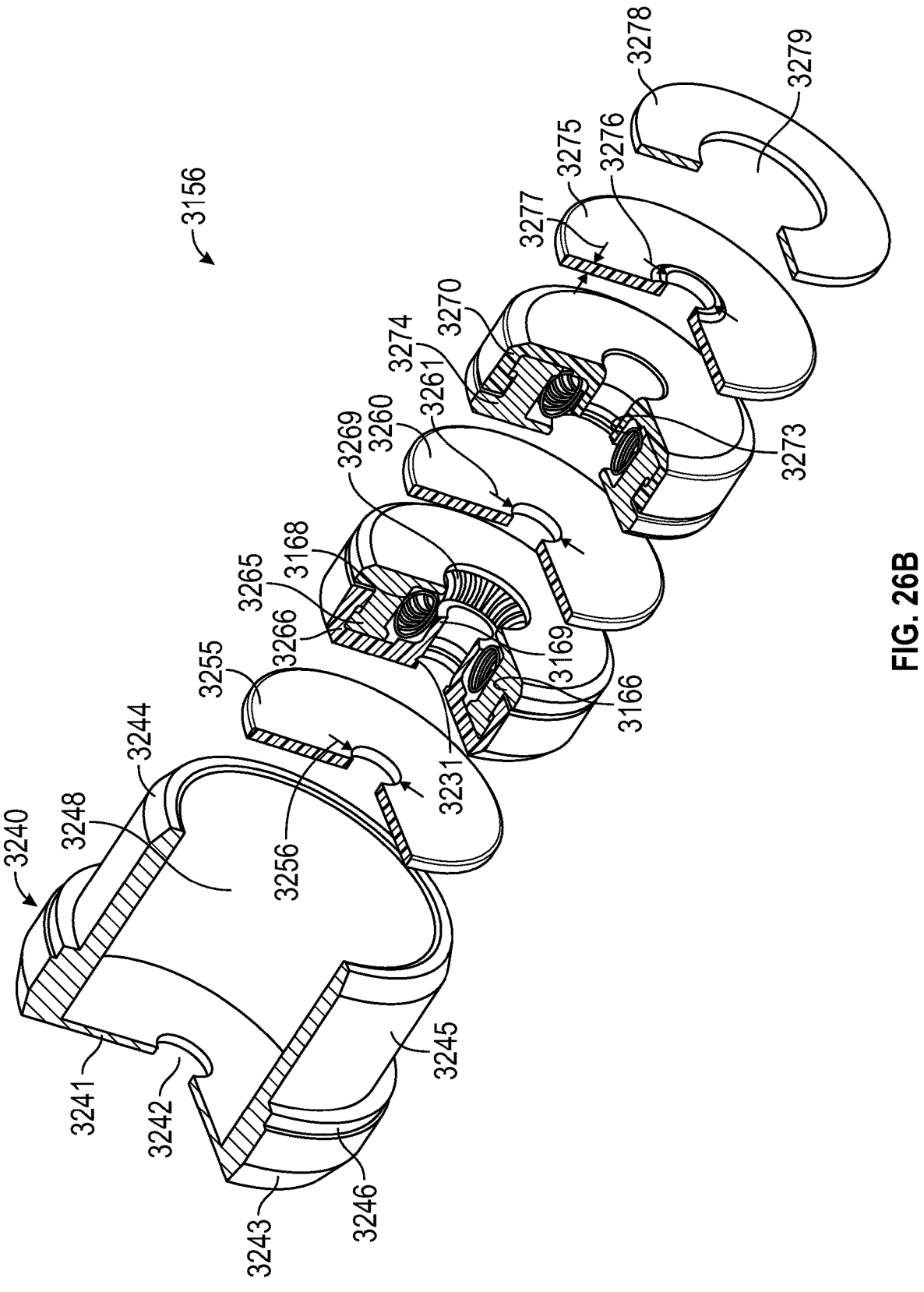
Figure 26C:
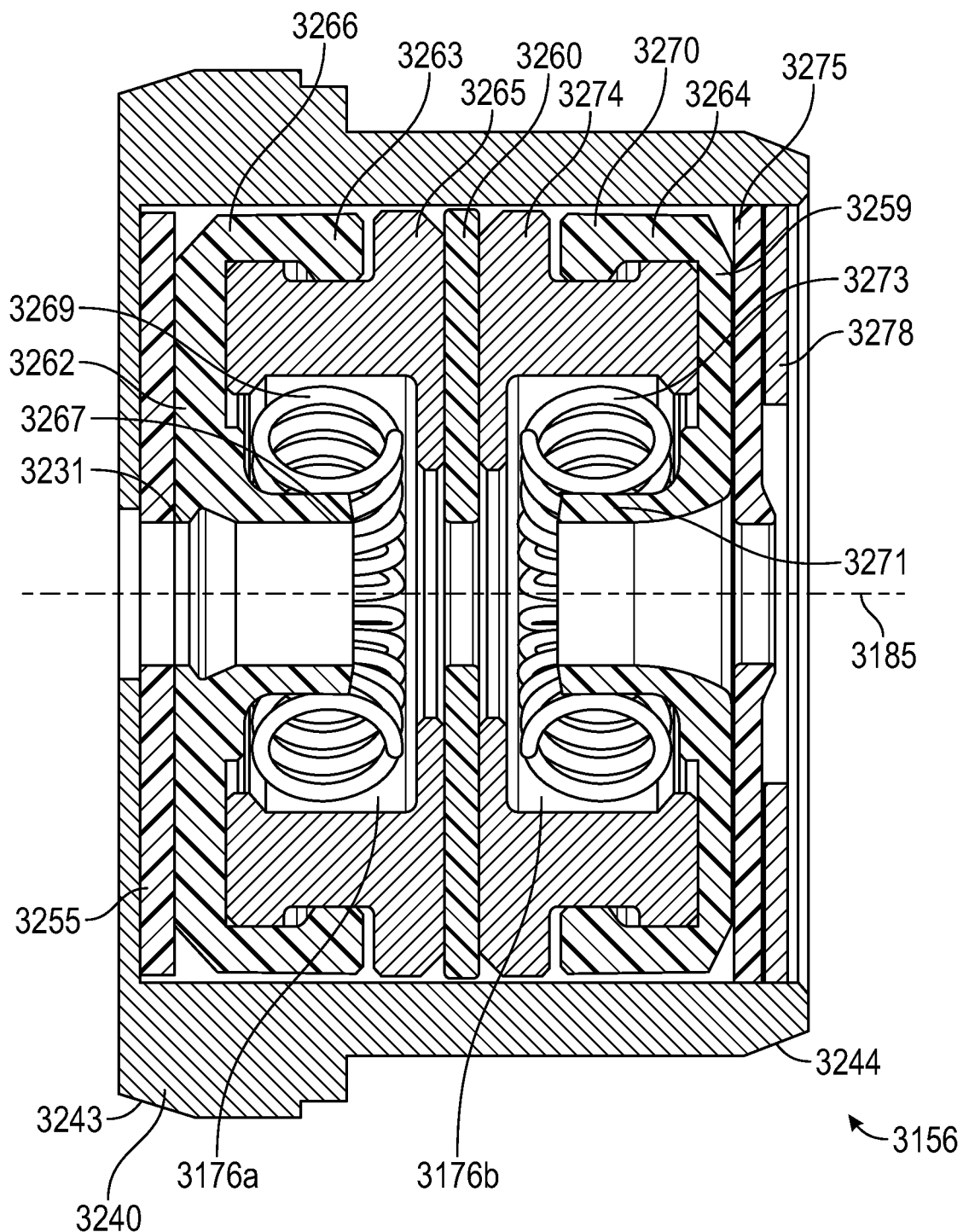

Another embodiment of an MCS device having a sealed rotary shaft is shown in FIGS. 26A-26C. FIG. 26A is a partial cross-sectional view of the device having two lip seals facing one another, a front disc, a middle disc, and a rear disc contained in a seal housing, FIG. 26B is an isometric, exploded, partially cut-away view thereof, and FIG. 26C is a cross-sectional view of the seal components shown isolated as a subassembly. The MCS device of FIGS. 26A-26C, or variations or embodiments thereof, may be included in any of the MCS systems described herein and may include any of the features for MCS devices described herein, and vice versa. Thus, for example, the pump 22, the MCS system 10, the motor housing 74, the pump 1900, the pump 2062, and/or the pump region 2160, etc. may include the MCS device or features thereof of FIGS. 26A-26C, in particular the sealing features thereof, and vice versa. In addition or alternatively to the features described herein with respect to FIGS. 26A-26C, any of the pump embodiments in this disclosure may include other features for a seal, for example those described in U.S. Provisional Application No. 63/229,436, titled SEAL FOR A MECHANICAL CIRCULATORY SUPPORT DEVICE and filed Apr. 14, 2021, the entire content of which is incorporated by reference herein in its entirety for all purposes and forms a part of this specification.

As shown in FIGS. 26A-26C, the device includes a distal annular radial or rotary shaft seal 3266 having a radially inward contact lip 3267 forming a seal cavity 3176a. The contact lip 3267 and seal cavity 3176a of the distal seal 3266 face proximally. The distal seal 3266 thus has an "open side"

facing proximally toward the motor, and a "flat side" facing distally toward the impeller and blood. The distal seal 3266 is thus oriented "backwards" from conventional orientations. In some embodiments, the "open side" may be a side of the seal 3266 formed in part by upper and/or lower flanges or lips of the seal 3266. A cavity may be formed by the open side of the seal 3266. The cavity may be formed between an end wall of the seal 3266 and the one or more flanges or lips of the seal 3266. The cavity may have a spring and/or grease located therein. Further details of the end wall, lips, etc. are described herein.

The device further includes a proximal annular radial or rotary shaft seal 3270, having a radially inward contact lip 3271 forming a seal cavity 3176b. The contact lip 3271 and a seal cavity 3176b of the proximal annular seal 3270 faces distally. The proximal seal 3270 thus has an "open side" (as described above) facing distally toward the motor, and a "flat side" facing proximally toward the impeller and blood. Therefore, the seal assembly includes the proximal annular seal 3270 and the distal annular seal 3266 having opposite orientations, with their contact lips 3267, 3271 and seal cavities 3176a, 3176b facing one another.

The lips 3267, 3271 contact the shaft 3140. The lips 3267, 3271 may extend along the shaft 3140. All or a part of the radially inward surface or surfaces of the lips 3267, 3271 may contact the shaft 3140. The lips 3267, 3271 may be flat, and/or have non-flat features, as described in further detail herein, for example with respect to FIG. 26C.

The seals 3266, 3270 may include radially outer lips 3263, 3264. The lips 3263, 3264 may contact a radially inward surface of the housing or other component of the seal compartment. The lips 3263, 3264 may extend along the housing or other component. The lips 3263, 3264 may seal off the space between the seal 3266, 3270 and the housing or other component. The radially outer surfaces of the lips 3263, 3264 may be flat, non-flat, or combinations thereof.

The lips 3263, 3264 may extend from respective end walls 3262, 3259. The lip 3263 extends distally from the end wall 3262. The lip 3264 extends proximally from the end wall 3259. The end walls 3262, 3259 may refer to the "flat" sides described herein. The radially inner lips 3267, 3271 may extend from the end walls 3262, 3259, as described. The outer lips 3263, 3264 may extend perpendicular to the end walls 3262, 3259, either under no external forces and/or when installed in the seal compartment. The outer lips 3263, 3264 may have the same or similar features as the inner lips 3267, 3271, such as the leading edge, groove or recess, etc.

In some embodiments, a middle elastomeric disc 3260 may be positioned between the proximal annular seal 3270 and the distal annular seal 3266. A distal elastomeric disc 3255 may be positioned distal to the distal annular seal 3266. A proximal elastomeric disc 3275 may be positioned proximal to the proximal annular seal 3270.

Optionally, a seal housing made of a front seal container 3240 and an optional seal container cap 3278 (see FIGS. 26B and 26C), may contain the seal components in a subassembly. The subassembly may be inserted over the drive shaft 3140 and into a motor housing 3164. Alternatively, the seal components may be assembled in the motor housing by inserting the components separately and sequentially over the drive shaft 3140 into a cavity in the motor housing. The seal components may then be covered with a rear (proximal) seal cap 3278 that may be attached (e.g., welded, friction fit, form fit, glued) to the motor housing.

Both the distal elastomeric disc 3255 and the middle elastomeric disc 3260 may be made from an elastomeric, biocompatible material such as PTFE, an elastic polyurethane, or a compound material such as PTFE and Polyimide. As shown in FIG. 26B, one or more of the discs 3255, 3260 may have an inner diameter (ID) 3256, 3261 that is less than the outer diameter (OD) of the drive shaft 3140, which optionally may include an impeller back extension 3154, that the inner diameter contacts. For example, the ID 3256, 3261 may be in a range of 80% to 95% (e.g., about 87%) that of the OD 3141. In one implementation, the ID 3256, 3261 is 0.52 mm+/−0.02 mm and the OD 3141 is 0.60 mm+/−0.01 mm. This dimensional difference creates high interference between the elastomeric discs 3255, 3260 and drive shaft to maintain a seal. For example, an ideal interference may be in a range of 0.070 mm to 0.080 mm The elastomeric discs 3255, 3260 may both have a thickness in a range of 80 μm to 140 μm (e.g., about 100 μm).

The properties of the elastomeric discs 3255, 3260 such as high interference, material durometer (e.g., in a range of 70 to 85 Shore), and thickness, may allow for the disc to deform when inserted over the drive shaft. For example, the disc may compress outward such that the disc ID may stretch, or the plane of the disc may curve particularly in a region close to the ID. The deformation of the disc may provide a contact pressure with the drive shaft 3140 even as the disc material wears over time. Furthermore, the high interference provides an amount of material that may be worn down before contact pressure is reduced to zero, which may prolong the functional duration of the disc 3255, 3260 to act as a blood barrier. Furthermore, the high interference may compensate for small tolerances of eccentricity of the drive shaft within the disc.

The properties of the discs 3255, 3260 may allow them to act as a fluid barrier, at least for a portion of the intended duration that the MCS device is in use, while minimizing friction or decrease in torque transmission. Additionally, the distal elastomeric disc 3255 may function as a first barrier to blood at least for a portion of duration of use. The middle elastomeric disc 3260, may function as an additional barrier to blood if it manages to pass the more distal barriers. Also, the disc 3260 may act as a divider between the distal annular seal cavity 3176a and proximal annular seal cavity 3176b help to keep grease that is contained in these cavities next to each annular seal, which in turn prolongs the functional duration of the annular seals. Optionally, the grease or lubricant dispensed in the distal seal cavity 3176a may be the same or different than that dispensed in the proximal seal cavity 3176b. In some embodiments, the proximal disc 3276 may have the same or similar features as the distal and middle discs 3255, 3260.

Other than their relative position and orientation, the distal seal 3266 and proximal seal 3270 may have similar properties to one another or to other seals 3156 disclosed in relation to other implementations. For example, both the distal and proximal seals may have a seal holder 3265, 3274, an annular seal with a contact lip 3267, 3271, a seal cavity 3176a, 3176b, partially defined by the seal holder and annular seal, and/or a garter spring 3269, 3273 held in the respective seal cavity 3176a, 3176b. The seals 3266, 3270 may have the same inner diameter and lip dimensions. Optionally the seals 3266, 3270 may have different outer diameters primarily so they are easily distinguishable from one another during manufacturing.

Alternative to a garter spring 3269, 3273 the seals may contain a different component that applies radially inward force such as an O-ring or not have a separate component that applies the force, wherein properties of an elastomeric annular seal with a contact lip self-applies a radially inward contact force.

The distal and proximal annular seals 3266, 3270, may be made from a biocompatible elastomeric material such as PTFE, an elastic polyurethane, or a compound material such as PTFE and Polyimide, which optionally may have one or more additives to enhance durability. Grease may be contained in one or both seal cavities 3176a, 3176b, and optionally a third grease reservoir held between the proximal seal and proximal disc 3275, and may be the same grease or different greases. In one implementation a first grease is deposited in the distal seal cavity, which may have a higher viscosity and grease consistency (e.g., NLGL Class 4 or higher) than a third grease (e.g., NLGL Class 2) deposited in the proximal seal cavity or a second grease held in the third grease reservoir held between the proximal seal and proximal disc. In another implementation grease is deposited in the distal seal cavity (e.g., NLGL Class 4 or higher) and an oil is deposited in the proximal seal cavity.

Optionally, the distal seal 3266 may have a leading edge 3231 on its distal face, which in addition to the contacting lip 3267 is a surface of the distal seal that contacts rotating parts such as the drive shaft 3140. The leading edge 3231 is a portion of the distal annular seal 3266 with an inner diameter that is less than the inner diameter of a portion of the contacting lip 3267 located proximally of the leading edge 3231. The leading edge 3231 may be a portion of the distal annular seal 3266 with an inner diameter that is less than the outer diameter of the motor drive shaft 3140 that the inner diameter mates with. For example, the ID of the leading edge may be in a range of 75% to 95% (e.g., 80% to 90%, about 87%) that of the OD 3141. In one implementation the ID is 0.52 mm and the OD 3141 is 0.60 mm. By making a flush connection to the rotating shaft 3140 on the distal face of the seal, the leading edge may function to reduce the occurrence of blood getting actively drawn underneath the contacting lip 3267, which may contribute to increasing the longevity of the seal. The distal annular seal 3266 may be made as shown with a groove between the leading edge 3231 and contact lip 3267. The leading edge 3231 may be formed in part by an adjacent groove or recess formed in the inner surface of the lip 3267. Alternatively, the leading edge 3231 may have a smooth transition to the contact lip 3267.

The orientation of the proximal seal 3270, wherein the contact lip 3271 and seal cavity 3176b are directed distally, may facilitate the overall sealing function in a number of ways: for example, lubricating grease is held in the cavities 3176b and 3176a between the distal seal 3266 and proximal seal 3270 which coats the contact surface between the contact lips 3267, 3271 and the drive shaft 3140 to reduce wear, minimize reduction of torque transmission or heat formation, and resist ingress of blood; a higher pressure on the distal side of the seal 3270 relative to the proximal side (e.g., due to compressed grease held in the seal cavity 3176b or in the event that blood manages to pass through the more distal blood barriers) may support the contact pressure of the contact lip 3271. The axial length of a portion of the contact lip 3271 that contacts the shaft may be in a range of 0.3 to 0.8 mm (e.g., about 0.5 mm).

Optionally, the device may have the proximal disc 3275 positioned proximal to the proximal seal 3270 as shown in FIG. 26A. The proximal disc may function as another barrier to prevent blood from entering drive shaft bearings 3162 or the motor compartment. Furthermore, the proximal disc may help to account for small tolerances in eccentricity of the drive shaft. The proximal disc 3275 may be made from a biocompatible elastomeric material such as PTFE or an elastic polyurethane or a compound and have a generally disc shape with a center hole having an inner diameter 3276 through which the drive shaft 3140 passes and makes contact. The ID 3276 may be in a range of 80% to 97% (e.g., about 93%) that of the OD 3141. In one implementation the ID is 0.56 mm and the OD 3141 is 0.6 mm, which may be greater than the ID of the distal disc 3255 or middle disc 3260 to have less impact on torque transmission losses. Optionally, the proximal disc 3275 may have a greater thickness than the distal or middle discs 3255, 3260 as shown in FIG. 26A, which together with the elastomeric properties of the disc may provide an axial compression of the sealing components when the proximal disc is compressed between a front seal container 3240 and an edge on the motor housing 3164. For example, the thickness of the proximal, middle and distal discs may be in a range of 0.10 mm to 0.15 mm. The proximal disc 3275 may be axially compressed due to dimensions of the stack up of seal components in the axial direction and the space within the housing that compresses the stack. In some embodiments, the proximal disc 3275 may be non-flat, e.g. spherical, such as a Belleville washer shape, to provide compression.

FIGS. 26B and 26C show the device of FIG. 26A but having a relatively thinner the proximal disc 3275, as well as the addition of a seal container cap 3278. In this implementation all of the sealing components are contained within a seal container, for example as a subassembly. The seal container may include a front seal container 3240 and the seal container cap 3278, which may be both made from a metal such as stainless steel or titanium and connected securely for example, with a friction fit, form fit, threading, or weld.

The front seal container 3240 functions to contain the seal components with or without the seal container cap 3278 and facilitate manufacturing. The front seal container has a flat, rigid distal surface 3241 that provides a surface for mechanically pressing the seal components into the motor housing 3164 while protecting the softer, more fragile seal components. The flat, rigid surface 3241 also ensures the axial gap 3174 between the surface 3241 and impeller is consistent so blood in the axial gap is expelled, and the back face of the rotating impeller does not contact the seal components inadvertently. The surface 3241 has a central hole 3242, which has an inner diameter that is larger than the outer diameter of the drive shaft 3140. For example, the hole 3242 may have a diameter that is in a range of 0.080 mm to 0.150 mm (e.g., about 0.100 mm) greater than the outer diameter of rotating parts passing through the hole, which may function as a physical filter to prevent particles from escaping the container as a risk management measure. For example, the hole 3242 may be in a range of 0.68 mm to 0.75 mm (e.g., about 0.70 mm) when the drive shaft has a diameter of 0.60 mm. In other words, a radial gap between the drive shaft and the container 3240 may be in a range of 0.040 mm to 0.075 mm (e.g., about 0.050 mm). The front seal container has cylindrical side walls with an inner surface 3248 that functions to constrain the seal components ensuring there is no lateral movement, which could compromise the integrity or longevity of the seals. A proximal chamfer 3244 facilitates insertion into the motor housing during manufacturing. A distal chamfer 3243 facilitates insertion of an inlet tube 3070, or alternatively an impeller housing 3082 over the front seal container 3240. Furthermore, the front seal container 3240 may have a recessed outer surface 3245 for inserting into the motor housing 3164. An embodiment of a heart pump having a seal element 3156 as shown in FIG. 26A may have a motor housing with a length no greater 25.5 mm. With additional length added to the motor housing by the seal subassembly and an optional wiring module connected to the proximal end of the motor housing, the length of the motor housing may be extended to no more than 33 mm.

A method of manufacturing a seal subassembly may include but not be limited to inserting the seal components into the front seal container in the order and orientation described herein, dispensing grease in the seal cavities optionally sequentially or simultaneously, releasing air bubbles using a centrifuge or vacuum chamber, and closing the seal container with the seal container cap 3278. The seal subassembly may be inserted over a drive shaft 3140, optionally into a motor housing, and connected to the motor housing, for example by laser welding an intersection which may include a rabbet 3246 of the front seal container 3240 and a rabbet 3247 of the motor housing. The impeller may be connected to the drive shaft, for example with an arrangement as described herein with respect to other embodiments and figures. An impeller housing 3082 or an inlet tube 3070 having an integrated impeller housing may be connected to the motor housing and/or front seal container 3240. The device may be packaged in an airtight package with air evacuated to prevent drying of the grease dispensed in the seals.

Any embodiments of the MCS systems, and features thereof, described herein may include various additional features or modifications, such as those described, for example, in PCT Pub. No. WO 2020/089429, filed on Oct. 31, 2019, titled SYSTEM AND METHOD FOR CONTROLLING A CARDIAC ASSISTANCE SYSTEM, in U.S. patent application Ser. No. 17/290,083, filed Apr. 29, 2021, titled SYSTEM AND METHOD FOR CONTROLLING A CARDIAC ASSISTANCE SYSTEM, in PCT Pub. No. WO 2019/229221, filed on May 30, 2019, titled ELECTRONICS MODULE AND ARRANGEMENT FOR A VENTRICULAR ASSIST DEVICE, AND METHOD FOR PRODUCING A VENTRICULAR ASSIST DEVICE, in U.S. patent application Ser. No. 17/057,039, filed Nov. 19, 2020, titled ELECTRONICS MODULE AND ARRANGEMENT FOR A VENTRICULAR ASSIST DEVICE, AND METHOD FOR PRODUCING A VENTRICULAR ASSIST DEVICE, in PCT Pub. No. WO 2019/234152, filed on Jun. 6, 2019, titled DEVICE AND METHOD FOR DETERMINATION OF A CARDIAC OUTPUT FOR A CARDIAC ASSISTANCE SYSTEM, in U.S. patent application Ser. No. 15/734,841, filed Jun. 18, 2021, titled DEVICE AND METHOD FOR DETERMINATION OF A CARDIAC OUTPUT FOR A CARDIAC ASSISTANCE SYSTEM, in PCT Pub. No. 2020/0030706, filed Aug. 7, 2019, titled DEVICE AND METHOD FOR MONITORING THE STATE OF HEALTH OF A PATIENT, in U.S. application Ser. No. 17/266,056, filed Oct. 13, 2021, titled DEVICE AND METHOD FOR MONITORING THE STATE OF HEALTH OF A PATIENT, in PCT Pub. No. WO 2020/064707, filed Sep. 24, 2019, titled METHOD AND SYSTEM FOR DETERMINING A FLOW SPEED OF A FLUID FLOWING THROUGH AN IMPLANTED, VASCULAR ASSISTANCE SYSTEM, in U.S. application Ser. No. 17/274,354, filed Mar. 8, 2021, titled METHOD AND SYSTEM FOR DETERMINING A FLOW SPEED OF A FLUID FLOWING THROUGH AN IMPLANTED, VASCULAR ASSISTANCE SYSTEM, in PCT Pub. No. WO 2019/234148, filed Jun. 9, 2019, titled IMPLANTABLE VENTRICULAR ASSIST SYSTEM AND METHOD FOR OPERATING SAME, in U.S. patent application Ser. No. 15/734,342, filed Jul. 30, 2021, titled IMPLANTABLE VENTRICULAR ASSIST SYSTEM AND METHOD FOR OPERATING SAME, in PCT Pub. No. WO 2019/234149, filed Jun. 9, 2019, titled SENSOR HEAD DEVICE FOR A MINIMAL INVASIVE VENTRICULAR ASSIST DEVICE AND METHOD FOR PRODUCING SUCH A SENSOR HEAD DEVICE, in U.S. patent application Ser. No. 15/734, 036, filed Jun. 8, 2021, titled SENSOR HEAD DEVICE FOR A MINIMAL INVASIVE VENTRICULAR ASSIST DEVICE AND METHOD FOR PRODUCING SUCH A SENSOR HEAD DEVICE, in PCT Pub. No. WO 2019/ 234166, filed Jun. 6, 2019, titled METHOD FOR DETERMINING A FLOW SPEED OF A FLUID FLOWING THROUGH AN IMPLANTED, VASCULAR ASSISTANCE SYSTEM AND IMPLANTABLE, VASCULAR ASSISTANCE SYSTEM, in U.S. patent application Ser. No. 15/734,523, filed Dec. 2, 2020, titled SYSTEMS AND METHODS FOR DETERMINING A FLOW SPEED OF A FLUID FLOWING THROUGH A CARDIAC ASSIST DEVICE, in PCT Pub. No. WO 2019/234167, filed Jun. 6, 2019, titled DETERMINATION APPLIANCE AND METHOD FOR DETERMINING A VISCOSITY OF A FLUID, in U.S. patent application Ser. No. 15/734,519, filed Dec. 2, 2020, titled DETERMINATION APPLIANCE AND METHOD FOR DETERMINING A VISCOSITY OF A FLUID, in PCT Pub. No. WO 2019/234169, filed Jun. 6, 2019, titled ANALYSIS APPARATUS AND METHOD FOR ANALYZING A VISCOSITY OF A FLUID, in U.S. patent application Ser. No. 15/734,489, filed Dec. 2, 2020, titled ANALYSIS APPARATUS AND METHOD FOR ANALYZING A VISCOSITY OF A FLUID, in PCT Pub. No. WO 2019/243582, filed Jun. 21, 2019, titled METHOD AND DEVICE FOR DETECTING A WEAR CONDITION OF A VENTRICULAR ASSIST DEVICE AND FOR OPERATING SAME, AND VENTRICULAR ASSIST DEVICE, and/or in U.S. patent application Ser. No. 17/252, 498, filed Jul. 27, 2021, titled METHOD AND DEVICE FOR DETECTING A WEAR CONDITION OF A VENTRICULAR ASSIST DEVICE AND FOR OPERATING SAME, AND VENTRICULAR ASSIST DEVICE, each of which are hereby incorporated by reference herein in their entirety for all purposes and forms a part of this specification.

EXAMPLE EMBODIMENTS

The following are numbered example embodiments of various embodiments of the mechanical circulatory support systems and methods disclosed herein. Any of the below Examples 1-38, or any other examples disclosed herein, may be combined in whole or in part. Elements of the examples disclosed herein are not limiting.

Example 1: A mechanical circulatory support system, comprising an elongate flexible catheter shaft, having a proximal end and a distal end, and a circulatory support device carried by the distal end of the shaft. The circulatory support device comprising a tubular housing, having a proximal end and a distal end, an impeller within the tubular housing, and a removable guidewire guide tube. The removable guidewire guide tube is entering a first guidewire port on the distal end of the tubular housing, exiting the tubular housing via a second guidewire port on a side wall of the tubular housing distal to the impeller, entering a third guidewire port on a proximal side of the impeller, and extending proximally into the catheter shaft.

Example 2: The mechanical circulatory support system or method of any of the Examples 1-38 or any other embodiment described herein, further comprising a motor within the tubular housing and configured to rotate the impeller.

Example 3: The mechanical circulatory support system or method of any of the Examples 1-38 or any other embodiment described herein, wherein the motor is positioned distal to the third guidewire port.

Example 4: The mechanical circulatory support system or method of any of the Examples 1-38 or any other embodiment described herein, wherein the tubular housing comprises a sealed motor housing that comprises the motor.

Example 5 The mechanical circulatory support system of any of the Examples 1-38, wherein the sealed motor housing comprises: a seal comprising a distal radial shaft seal having a distal side configured to face distally toward the impeller and a radially inner lip configured to contact the shaft and to extend from the distal side in a proximal direction toward the motor.

Example 6: The mechanical circulatory support system or method of any of the Examples 1-38 or any other embodiment described herein, further comprising an annular seal surrounding a shaft, wherein the motor is configured to rotate the impeller via the shaft.

Example 7: The mechanical circulatory support system or method of any of the Examples 1-38 or any other embodiment described herein, wherein the tubular housing comprises an inlet tube having an axial length in a range from about 60 mm to about 100 mm.

Example 8: The mechanical circulatory support system or method of any of the Examples 1-38 or any other embodiment described herein, wherein the tubular housing comprises: a blood outlet in communication with the impeller; and a blood inlet spaced distally apart from the blood outlet.

Example 9: The mechanical circulatory support system or method of any of the Examples 1-38 or any other embodiment described herein, wherein the tubular housing comprises a flexible tube having a polymeric sleeve.

Example 10: The mechanical circulatory support system or method of any of the Examples 1-38 or any other embodiment described herein, further comprising a funnel on a distal end of the guide tube, wherein the funnel leads into the removable guidewire guide tube.

Example 11: The mechanical circulatory support system or method of any of the Examples 1-38 or any other embodiment described herein, further comprising a pull tab attached to the guide tube to facilitate grasping and removing the guide tube.

Example 12: The mechanical circulatory support system or method of any of the Examples 1-38 or any other embodiment described herein, wherein the guide tube is configured to split to allow for removal of the guide tube from the guidewire without having to slide the guide tube axially off an end of the guidewire.

Example 13: The mechanical circulatory support system or method of any of the Examples 1-38 or any other embodiment described herein, wherein the tubular housing comprises a nose piece that comprises the first guidewire port.

Example 14: The mechanical circulatory support system or method of any of the Examples 1-38 or any other embodiment described herein, further comprising a tubular insertion tool configured to removably axially receive the circulatory support device, with the removable guidewire guide tube extending between the circulatory support device and the tubular insertion tool.

Example 15: The mechanical circulatory support system or method of any of the Examples 1-38 or any other embodiment described herein, wherein the tubular housing comprises an inlet tube configured to attach to the sealed motor housing via form-locking or force-locking.

Example 16: A mechanical circulatory support system, comprising an elongate flexible catheter shaft having a proximal end and a distal end, and a circulatory support device carried by the distal end of the shaft. The circulatory support device comprising a tubular housing and an impeller within the tubular housing, wherein the circulatory support device comprises a guidewire path that extends through the catheter shaft and along an exterior part of the tubular housing to avoid the impeller.

Example 17: The mechanical circulatory support system or method of any of the Examples 1-38 or any other embodiment described herein, where the guidewire path extends through an interior portion of a distal end of the tubular housing.

Example 18: The mechanical circulatory support system or method of any of the Examples 1-38 or any other embodiment described herein, further comprising a first guidewire port on a distal end of the tubular housing.

Example 19: The mechanical circulatory support system or method of any of the Examples 1-38 or any other embodiment described herein, further comprising a second guidewire port on a side wall of the tubular housing distal to the impeller.

Example 20: The mechanical circulatory support system or method of any of the Examples 1-38 or any other embodiment described herein, further comprising a third guidewire port on a proximal side of the impeller.

Example 21: The mechanical circulatory support system or method of any of the Examples 1-38 or any other embodiment described herein, further comprising a removable guidewire guide tube configured to guide a guidewire therethrough.

Example 22: The mechanical circulatory support system or method of any of the Examples 1-38 or any other embodiment described herein, wherein the removable guidewire guide tube is configured to enter a first guidewire port on the distal end of the tubular housing, to exit the housing via a second guidewire port on a side wall of the tubular housing distal to the impeller, and to extend through a third guidewire port on a proximal side of the impeller to extend proximally into the catheter shaft.

Example 23: The mechanical circulatory support system or method of any of the Examples 1-38 or any other embodiment described herein, wherein the tubular housing comprises an inlet tube and a motor housing.

Example 24: The mechanical circulatory support system or method of any of the Examples 1-38 or any other embodiment described herein, wherein the tubular housing comprises an inlet tube and a nose piece on a distal end of the inlet tube, and the nose piece comprises the first guidewire port.

Example 25: The mechanical circulatory support system or method of any of the Examples 1-38 or any other embodiment described herein, further comprising an insertion tool configured to removably axially receive the circulatory support device such that the guidewire path extends between the circulatory support device and the insertion tool.

Example 26: The mechanical circulatory support system of any of Examples 1-38, wherein the motor housing comprises a sealed motor housing that comprises the motor.

Example 27: The mechanical circulatory support system of any of Examples 1-38, wherein the sealed motor housing comprises: a seal comprising a distal radial shaft seal having a distal side configured to face distally toward the impeller and a radially inner lip configured to contact the shaft and to extend from the distal side in a proximal direction toward the motor.

Example 28: A method of inserting a guidewire through a mechanical circulatory support system, the method comprising: inserting the guidewire into a distal end of a removable guide tube, wherein the guide tube enters a first guidewire port on a distal end of a tubular housing of the system, exits the tubular housing via a second guidewire port on a side wall of the tubular housing distal to an impeller of the system, enters a third guidewire port on a proximal side of the impeller, and extends proximally into a catheter shaft.

Example 29: The mechanical circulatory support system or method of any of the Examples 1-38 or any other embodiment described herein, further comprising inserting the removable guide tube through the first, second, and third guidewire ports.

Example 30: The mechanical circulatory support system or method of any of the Examples 1-38 or any other embodiment described herein, further comprising removing the removable guide tube from the system.

Example 31: The mechanical circulatory support system or method of any of the Examples 1-38 or any other embodiment described herein, wherein removing the guide tube comprises pulling and removing a pull tab from the distal end of the housing.

Example 32: The mechanical circulatory support system or method of any of the Examples 1-38 or any other embodiment described herein, wherein removing the guide tube comprises removing the guide tube from the guidewire with the guidewire partially in the patient.

Example 33: The mechanical circulatory support system or method of any of the Examples 1-38 or any other embodiment described herein, wherein removing the guide tube comprises splitting the guide tube and laterally removing the guide tube from the guidewire.

Example 34: The mechanical circulatory support system or method of any of the Examples 1-38 or any other embodiment described herein, wherein the tubular housing comprises an inlet tube that comprises the second guidewire port.

Example 35: The mechanical circulatory support system or method of any of the Examples 1-38 or any other embodiment described herein, wherein the tubular housing comprises an inlet tube and a nose piece on a distal end of the inlet tube, and the nose piece comprises the first guidewire port.

Example 36: A method of transcatheter delivery of a pump to the heart, the method comprising advancing the pump through vasculature, wherein the pump is advanced having a guidewire that extends through a first section of a catheter shaft located distal to the pump, through a tubular housing of the pump, external to an impeller and motor of the pump, and back into a second section of the catheter shaft located proximal to the pump.

Example 37: The mechanical circulatory support system or method of any of the Examples 1-38 or any other embodiment described herein, comprising starting the motor and/or rotating the impeller prior to removal of the guidewire from the pump and/or prior to placement of the pump in the heart.

Example 38: The mechanical circulatory support system or method of any of the Examples 1-38 or any other embodiment described herein, comprising leaving the guidewire in the pump during use of the pump so the guidewire and/or pump at least partially remains in the left ventricle.

In any of the above or other examples, the system may include a motor within the tubular housing and configured to rotate the impeller; the motor may be positioned distal to the third guidewire port; the tubular housing may comprise a sealed motor housing that comprises the motor; the tubular housing may an axial length in a range of 60 mm to 100 mm; the system may include a blood exit port on the tubular housing in communication with the impeller, and/or a blood intake port on the housing spaced distally apart from the blood exit port; the housing may include a flexible slotted tube covered by an outer polymeric sleeve; and/or the system may include a sealed motor housing inside of the tubular housing.

In any of the above or other examples, a mechanical circulatory support system for high risk coronary interventions may be provided; the system may include a circulatory support catheter, including a circulatory support device carried by an elongate flexible catheter shaft, an insertion tool having a tubular body and configured to axially movably receive the circulatory support device, and an access sheath, having a tubular body and configured to axially movably receive the insertion tool; the access sheath may include an access sheath hub having an insertion tool lock for engaging the insertion tool; and/or the access sheath hub may include a catheter shaft lock for locking the access sheath hub to the catheter shaft.

In any of the above or other examples, a controller configured to drive a motor of a mechanical circulatory support system may be provided, wherein the controller does not include a purging component; the purging component can include a cassette or a port; and/or the system does not require purging.

In any of the above or other examples, a controller configured to drive a motor of a mechanical circulatory support system having a housing for mounting electronic components and a handle disposed on a top portion of the housing may be provided; the controller can include a visual alarm element wrapped around the handle on the top portion of the housing; the housing may not include more than one control element; the control element can be a rotary dial; the control element may be positioned on a first end of the housing; the controller may include a cable management system, said cable management system positioned on a second end opposite the first end; and/or the controller may include a rotating securing attachment on a rear side of the housing.

Terminology

Any methods disclosed herein need not be performed in the order recited. The methods disclosed herein include certain actions taken by a practitioner; however, they can also include any third-party instruction of those actions, either expressly or by implication.

Conditional language used herein, such as, among others, "can," "could," "might," "may," "e.g.," and the like, unless specifically stated otherwise, or otherwise understood within the context as used, is generally intended to convey that certain, certain features, elements and/or steps are optional. Thus, such conditional language is not generally intended to imply that features, elements and/or steps are in any way required or that one or more implementations necessarily include logic for deciding, with or without other input or prompting, whether these features, elements and/or steps are included or are to be always performed. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain implementations require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain implementations, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Any methods disclosed herein need not be performed in the order recited. The methods disclosed herein include certain actions taken by a practitioner; however, they can also include any third-party instruction of those actions, either expressly or by implication.

The methods and tasks described herein may be performed and fully automated by a computer system. The computer system may, in some cases, include multiple distinct computers or computing devices (for example, physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (for example, solid state storage devices, disk drives, etc.). The various functions disclosed herein may be embodied in such program instructions, and/or may be implemented in application-specific circuitry (for example, ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. The computer system may be a cloud-based computing system whose processing resources are shared by multiple distinct business entities or other users.

While the above detailed description has shown, described, and pointed out novel features, it can be understood that various omissions, substitutions, and changes in the form and details of the devices or algorithms illustrated can be made without departing from the spirit of the disclosure. As can be recognized, certain portions of the description herein can be embodied within a form that does not provide all of the features and benefits set forth herein, as some features can be used or practiced separately from others. The scope of certain implementations disclosed herein is indicated by the appended claims rather than by the foregoing description. All changes which come within the meaning and range of equivalency of the claims are to be embraced within their scope.

What is claimed is:

1. A mechanical circulatory support system, comprising:
an elongate flexible catheter shaft, having a proximal end and a distal end; and
a circulatory support device carried by the distal end of the shaft, the circulatory support device comprising:
a tubular housing, having a proximal end and a distal end;
an impeller within the tubular housing; and
a removable guidewire guide tube entering a first guidewire port on the distal end of the tubular housing, the guide tube exiting the tubular housing via a second guidewire port on a side wall of the tubular housing, the guide tube entering a third guidewire port on a proximal side of the impeller, and the guide tube extending proximally into the catheter shaft.

2. The mechanical circulatory support system of claim 1, further comprising a motor within the tubular housing and configured to rotate the impeller.

3. The mechanical circulatory support system of claim 2, wherein the motor is positioned distal to the third guidewire port.

4. The mechanical circulatory support system of claim 2, wherein the tubular housing comprises a sealed motor housing that comprises the motor.

5. The mechanical circulatory support system of claim 4, wherein the tubular housing comprises an inlet tube configured to attach to the sealed motor housing via form-locking or force-locking.

6. The mechanical circulatory support system of claim 2, further comprising an annular seal surrounding a shaft, wherein the motor is configured to rotate the impeller via the shaft.

7. The mechanical circulatory support system of claim 1, wherein the tubular housing comprises an inlet tube having an axial length in a range from about 60 mm to about 100 mm.

8. The mechanical circulatory support system of claim 1, wherein the tubular housing comprises:
a blood outlet in communication with the impeller; and
a blood inlet spaced distally apart from the blood outlet.

9. The mechanical circulatory support system of claim 8, wherein the second guidewire port is proximal to the blood inlet.

10. The mechanical circulatory support system of claim 1, wherein the tubular housing comprises a flexible tube having a polymeric sleeve.

11. The mechanical circulatory support system of claim 1, further comprising a funnel on a distal end of the guide tube, wherein the funnel leads into the guide tube.

12. The mechanical circulatory support system of claim 1, further comprising a pull tab attached to the guide tube to facilitate grasping and removing the guide tube.

13. The mechanical circulatory support system of claim 1, wherein the guide tube is configured to split to allow for removal of the guide tube from the guidewire without having to slide the guide tube axially off an end of the guidewire.

14. The mechanical circulatory support system of claim 1, wherein the tubular housing comprises a nose piece that comprises the first guidewire port.

15. The mechanical circulatory support system of claim 1, further comprising a tubular insertion tool configured to removably axially receive the circulatory support device, with the guide tube extending between the circulatory support device and the tubular insertion tool.

16. The mechanical circulatory support system of claim 1, wherein the second guidewire port is distal to the impeller.

* * * * *